US008796474B1

(12) United States Patent (10) Patent No.: US 8,796,474 B1
Williams et al. (45) Date of Patent: Aug. 5, 2014

(54) MACROLIDE COMPOUNDS AND METHODS AND INTERMEDIATES USEFUL FOR THEIR PREPARATION

(75) Inventors: Lawrence J. Williams, New Brunswick, NJ (US); Hiyun Kim, New Brunswick, NJ (US); Kai Liu, New Brunswick, NJ (US); Rojita Sharma, New Brunswick, NJ (US)

(73) Assignee: Rutgers, the State University of New Jersey, New Brunswick, NJ (US)

( * ) Notice: Subject to any disclaimer, the term of this patent is extended or adjusted under 35 U.S.C. 154(b) by 0 days.

(21) Appl. No.: 13/215,986

(22) Filed: Aug. 23, 2011

Related U.S. Application Data

(60) Provisional application No. 61/376,197, filed on Aug. 23, 2010, provisional application No. 61/447,987, filed on Mar. 1, 2011.

(51) Int. Cl.
 *C07D 313/00* (2006.01)
(52) U.S. Cl.
 USPC .......................................................... 549/266
(58) Field of Classification Search
 USPC .......................................................... 549/299
 See application file for complete search history.

(56) References Cited

U.S. PATENT DOCUMENTS

| | | |
|---|---|---|
| 6,740,642 B2 | 5/2004 | Angehrn et al. |
| 6,765,016 B1 | 7/2004 | Qiu et al. |
| 6,825,172 B2 | 11/2004 | Henninger et al. |
| 6,878,691 B2 | 4/2005 | Or et al. |
| 7,135,573 B2 | 11/2006 | Kim et al. |
| 7,163,924 B2 | 1/2007 | Burger et al. |
| RE39,591 E | 4/2007 | Or et al. |
| RE39,836 E | 9/2007 | Chu et al. |
| 7,271,155 B2 | 9/2007 | Or et al. |
| 7,335,753 B2 | 2/2008 | Wang et al. |
| 2010/0113585 A1 | 5/2010 | Falkowski |

OTHER PUBLICATIONS

Ghosh et al. New Methods and strategeis towards total synthesis of (9S)-dihydroerythronolide A, Rutgers University, Dissertation, May 2008 (see IDS NPL filed May 14, 2013).*
Kai Liu, Total Synthesis of Eruthronolides, ACS Meeting, Boston MA, Aug. 23, 2010.*
Ghosh et al. New Methods and strategies towards total synthesis of (9S)-dihydroerythronolide A, Rutgers University, Dissertation, May 2008 (see IDS NPL filed May 14, 2013).*
Aebi et al., "Sesquiterpenoids. Part III. The Stereochemistry of Caryophyllene." *J. Chem. Soc.*, 3124-3129, (1953).
Aebi et al., "Sesquiterpenoids. Part V. The Stereochemistry of the Tricyclic Derivatives of Caryophyllene", *J. Chem. Soc.*, 4659-4665, (1954).
Agouridas et al., "Synthesis and Antibacterial Activity of Ketolides (6-*O*-Methyl-3-oxoerythromycin Derivatives): A New Class of Anti-bacterials Highly Potent Against Macrolide-Resistant and -Susceptible Respiratory Pathogens", *J. Med. Chem.*, 41, pp. 4080-4100, (1998).
Bertz et al., "Effect of TMSCI on the Conjugate Addition of Organocuprates to α-Enones: A New Mechanism", *J. Am. Chem. Soc.*, 117, 11023-11024, (1995).
Burger et al., "Synthesis and Antibacterial Activity of Novel $C_{12}$ Vinyl Ketolides", *J. Med. Chem.*, 49, 1730-1743, (2006).
Christoffersen, "Antibiotics—an investment worth making?", *Nature Biotechnology 24* (12), 1512-1514 (2006).
Gansäuer et al., "A Radical Tandem Reaction with Homolytic Cleavage of a Ti—O Bond", *Angew. Chem. Int. Ed.*, 42, 3687-3690, (2003).
Gansäuer et al., "A Radical Roundabout for an Unprecedented Tandem Reaction Including a Homolytic Substitution with a Titanium—Oxygen Bond", *Eur. J. Org. Chem.*, 2337-2351, (2004).
Ghosh, P., "New methods and strategies towards total synthesis of (9S)-dihydroerythronolide A", Rutgers University, Dissertation, May 2008.
Ghosh et al., "Modeling a Macrocyclic Bis[spirodiepoxide] Strategy to Erythronolide A", *Org. Lett.*, vol. 11, No. 19, 4402-4405, (2009).
Keyes et al., "Synthesis and Antibacterial Activity of 6-*O*-Arylbutynyl Ketolides with Imrpoved Activity against Some Key Erythromycin-Resistant Pathogens", *J. Med. Chem.*, 46, 1795-1798, (2003).
Kinoshita et al., "Synthetic Studies of Erythromycins. III. Total Synthesis of Erythronolide A Through (9Z)-9-Dihydroerythronolide A", *Tetrahedron Lett.*, 27 (16), 1815-1818, (1986).
Kai Liu et al., "Total Synthesis of Erythronolides", ACS Meeting, Boston MA, Aug. 23, 2010.
Magee et al., "Discovery of Azetidinyl Ketolides for the Treatment of Susceptible and Multidrug Resistant Community-Acquired Respiratory Tract Infections", *J. Med. Chem.*, 52, 7446-7457, (2009).
Mushti et al., "Total Synthesis of Antheliolide A", *J. Am. Chem. Soc.*, 128, 14050-14052, (2006).
Raja et al., "Telithromycin", *Nature Reviews Drug Discovery 3*, 733-734 (2004).
Renneberg et al., "Total Synthesis of Coraxeniolide-A", *J. Org. Chem.*, 65, 9069-9079, (2000).
Schlunzen et al., "Structural basis for the interaction of antibiotics with the peptidyl transferase centre in eubacteria", *Nature*, 413, 814-821, (2001).
Toshima et al., "Application of Highly Stereocontrolled Glycosidations Employing 2,6-Anhydro-2-thio Sugars to the Syntheses of Erythromycin A and Olivomycin A Trisaccharide", *J. Am. Chem. Soc.*, 117, 3717-3727, (1995).
Velvadapu et al., "Concise syntheses of d-desosamine, 2-thiopyrimidinyl desosamine donors, and methyl desosaminide analogues from d-glucose", *Carbohydrate Research*, vol. 343, No. 1, pp. 145-150, (2008).

(Continued)

*Primary Examiner* — Nizal Chandrakumar
(74) *Attorney, Agent, or Firm* — Viksnins Harris & Padys PLLP

(57) ABSTRACT

The present invention provides intermediate compounds and synthetic methods that can be used to prepare complex cyclic compounds including macrolides. The invention also provides cyclic compounds that have useful biological properties such as antiinfective, antiinflammatory, or antitumor properties.

4 Claims, No Drawings

(56) References Cited

OTHER PUBLICATIONS

Williams et al., "Studies for the Synthesis of Xenicane Diterpenes. A Stereocontrolled Total Synthesis of 4-Hydroxydictyolactone", *J. Am. Chem. Soc.*, 131, 9038-9045, Jun. 1, 2009 (Web).

Wuitschik et al., "Oxetanes in Drug Discovery: Structural and Synthetic Insights", *J. Med. Chem.*, V. 53, (8), p. 3227-3246, (2010).

Yat Sun Or et al., "Design, Synthesis, and Antimicrobial Activity of 6-O-Substituted Ketolides Active against Resistant Respiratory Tract Pathogens", *J. Med. Chem.*, 43, 1045-1049, (2000).

Zhenkun Ma et al., "Novel Erythromycin Derivatives with Aryl Groups Tethered to the C-6 Position are Potent Protein Synthesis Inhibitors and Active Against Multidrug-Resistant Respiratory Pathogens", *J. Med. Chem.*, 44, 4137-4156, (2001).

* cited by examiner

MACROLIDE COMPOUNDS AND METHODS AND INTERMEDIATES USEFUL FOR THEIR PREPARATION

STATEMENT OF GOVERNMENT SUPPORT

The invention described herein was made with United States Government support under Grant Number R01GM078145 awarded by The National Institutes of Health. The United States Government has certain rights in the invention.

PRIORITY OF INVENTION

This application claims priority from U.S. Provisional Application No. 61/376,197, filed 23 Aug. 2010, and from U.S. Provisional Application No. 61/447,987, filed 1 Mar. 2011. The entire content of each of these provisional applications is hereby incorporated by reference herein.

BACKGROUND OF THE INVENTION

Antiinfectives constitute a 25 billion dollar industry. Macrolides constitute one of the largest groups of antiinfectives and the erythronolide/ketolides are the single largest group among these. Such antiinfectives are the treatment of choice for respiratory tract infections, the eighth leading killer in the US.

Macrolides have a broad range of medicinal properties, especially as antiinfectives and antitumor agents. The potent and broad spectrum antibiotic erythromycin and the close relatives known as the ketolides are examples of complex macrolides. Unfortunately, many macrolides are so structurally complex that they can not be synthesized readily by known chemical methods. Instead, they are prepared semi-synthetically, i.e. fermentation processes are used to produce erythromycin and then chemical synthesis protocols that use erythromycin as a starting point are applied to produce new drug candidates. Importantly, such semi-synthetic routes—which all current routes to such candidates use—are severely limited with regard to the structural scope of macrolides that can be evaluated.

Model studies to investigate the possible use of cyclic bis-allenes as intermediates for preparing biologically active macrolides have been carried out. See Partha Ghosh ("New methods and strategies towards total synthesis of 9-S-dihydroerythronolide A," Rutgers University, Dissertation, 2008). However, it has subsequently been determined that the conversion of compound 6.1 to compound 6.28 proposed on page 66 therein was not successful. Additionally, it has also been determined that conversions of compound 6.30 to compound 6.33, compound 6.45 to compound 6.47, and compound 6.55 to compound 6.66 therein were also not successful as reported therein. The source of the failure has been traced to the instability of intermediate tetraepoxide species (e.g. compounds 6.28, 6.30, 6.45, and 6.55 therein) thought to have been observed in the reaction mixtures.

In spite of the above reports, there is currently a need for novel intermediates and methods that can be used to synthesize complex cyclic compounds such as macrolides. There is also a need for novel macrolide compounds with useful biological properties such as antiinfective, anti-inflammatory, or antitumor properties.

SUMMARY OF THE INVENTION

The present invention provides intermediate compounds and synthetic methods that can be used to prepare complex cyclic compounds including macrolides. The invention also provides cyclic compounds that have useful biological properties such as antiinfective, anti-inflammatory or antitumor properties.

The invention also provides a pharmaceutical composition comprising a compound of the invention, or a pharmaceutically acceptable salt thereof, and a pharmaceutically acceptable diluent or carrier.

The invention also provides a method for producing an antiinfective effect in a mammal, comprising administering a compound of the invention, or a pharmaceutically acceptable salt thereof, to the mammal.

The invention also provides a method for treating cancer in a mammal, comprising administering a compound of the invention, or a pharmaceutically acceptable salt thereof, to the mammal.

The invention also provides a method for producing an antiinflammatory effect in a mammal, comprising administering a compound of the invention, or a pharmaceutically acceptable salt thereof, to the mammal.

The invention provides a compound of formula I or a pharmaceutically acceptable salt thereof for use in the prophylactic or therapeutic treatment of an infection.

The invention provides a compound of formula I or a pharmaceutically acceptable salt thereof for use in the prophylactic or therapeutic treatment of inflammation.

The invention provides a compound of formula I or a pharmaceutically acceptable salt thereof for use in medical therapy (e.g. for use in treating an infection, inflammation or cancer), as well as the use of a compound of formula I or a pharmaceutically acceptable salt thereof for the manufacture of a medicament useful for the treatment of an infection, inflammation, or cancer in a mammal, such as a human.

The invention also provides a method for preparing an oxetanone, comprising converting a corresponding allene to the oxetanone.

The invention also provides processes and intermediates disclosed herein that are useful for preparing cyclic compounds (e.g. macrolides) and salts thereof.

DETAILED DESCRIPTION

The following definitions are used, unless otherwise described: halo is fluoro, chloro, bromo, or iodo. Alkyl, alkoxy, alkenyl, alkynyl, etc. denote both straight and branched groups; but reference to an individual radical such as propyl embraces only the straight chain radical, a branched chain isomer such as isopropyl being specifically referred to. Aryl denotes a phenyl radical or an ortho-fused bicyclic carbocyclic radical having about nine to ten ring atoms in which at least one ring is aromatic. Heteroaryl encompasses a radical of a monocyclic aromatic ring containing five or six ring atoms consisting of carbon and one to four heteroatoms each selected from the group consisting of non-peroxide oxygen, sulfur, and N(X) wherein X is absent or is H, O, $(C_1-C_4)$alkyl, phenyl or benzyl, as well as a radical of an ortho-fused bicyclic heterocycle of about eight to ten ring atoms comprising one to four heteroatoms each selected from the group consisting of non-peroxide oxygen, sulfur, and N(X).

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase).

Specific values listed below for radicals, substituents, and ranges, are for illustration only; they do not exclude other defined values or other values within defined ranges for the radicals and substituents Specifically, $(C_1-C_6)$alkyl can be methyl, ethyl, propyl, isopropyl, butyl, iso-butyl, sec-butyl, pentyl, 3-pentyl, or hexyl; $(C_3-C_6)$cycloalkyl can be cyclopropyl, cyclobutyl, cyclopentyl, or cyclohexyl; $(C_1-C_6)$alkoxy can be methoxy, ethoxy, propoxy, isopropoxy, butoxy, iso-butoxy, sec-butoxy, pentoxy, 3-pentoxy, or hexyloxy; $(C_2-C_6)$alkenyl can be vinyl, allyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, or 5-hexenyl; $(C_2-C_6)$alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl; $(C_1-C_6)$alkanoyl can be acetyl, propanoyl or butanoyl; $(C_1-C_6)$alkoxycarbonyl can be methoxycarbonyl, ethoxycarbonyl, propoxycarbonyl, isopropoxycarbonyl, butoxycarbonyl, pentoxycarbonyl, or hexyloxycarbonyl; $(C_2-C_6)$alkanoyloxy can be acetoxy, propanoyloxy, butanoyloxy, isobutanoyloxy, pentanoyloxy, or hexanoyloxy; aryl can be phenyl, indenyl, or naphthyl; and heteroaryl can be furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

The term saccharide includes monosaccharides, disaccharides, trisaccharides and polysaccharides. The term includes glucose, sucrose, fructose and ribose, as well as, amino sugars such as desosamine, deoxy sugars such as deoxyribose, the like and their variants. Saccharide derivatives can conveniently be prepared as described in International Patent Applications Publication Numbers WO 96/34005 and 97/03995. A saccharide can conveniently be linked to the remainder of a compound of formula Ia through carbon atom, a heteroatom, or through an alkyl or heteroalkyl linker.

The term "prodrug" as used herein refers to any compound that when administered to a biological system (e.g. a mammal such as a human) generates the drug substance, i.e. active ingredient, as a result of spontaneous chemical reaction(s), enzyme catalyzed chemical reaction(s), photolysis, and/or metabolic chemical reaction(s) or by some other process. A prodrug is thus a modified (e.g. covalently modified) analog or latent form of a therapeutically-active compound. A prodrug may also be an active metabolite or therapeutically-active compound itself. A "prodrug group" is a group that can be attached to an active compound to form a prodrug. Numerous prodrug groups that can be attached to a hydroxy group on a therapeutically active compound to form a prodrug are known.

In one embodiment of the invention the saccharide can have the following formula:

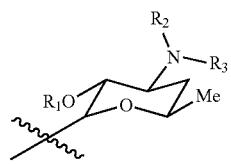

wherein $R_1$ is H, a protecting group, or a prodrug group; and $R_2$ and $R_3$ are each independently $(C_1-C_6)$alkyl, $(C_3-C_6)$cycloalkyl, or heterocycloalkyl (e.g. a cycloalkyl with one or more heteroatoms (O, N, S) in the ring; or $R_2$ and $R_3$ together with the nitrogen to which they are attached form a aziridino, azetidino, morpholino, piperazino, pyrrolidino or piperidino. See for example *Carbohydrate Research*, Volume 343, Issue 1, 14 Jan. 2008, Pages 145-150, which is hereby incorporated herein by reference.

In one embodiment of the invention the saccharide can have the following formula:

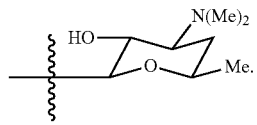

"Protecting group" refers to a moiety of a compound that masks or alters the properties of a functional group or the properties of the compound as a whole. Chemical protecting groups and strategies for protection/deprotection are well known in the art. See e.g., *Greene's Protective Groups in Organic Synthesis*, Peter G. M. Wuts and Theodora W. Greene, John Wiley & Sons, Inc., New York, 2007. Protecting groups are often utilized to mask the reactivity of certain functional groups, to assist in the efficiency of desired chemical reactions, e.g., making and breaking chemical bonds in an ordered and planned fashion. Chemically protected intermediates may themselves be biologically active or inactive. Specific protecting groups include benzyl (Bn), In cases where compounds are sufficiently basic or acidic, a salt of a compound of a compound can be useful as an intermediate for isolating or purifying the corresponding compound. Additionally, administration of a compound as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartrate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820, 508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The following Scheme and Preparative Examples illustrate the preparation of a bis-allene compound 116 that is a convenient starting material for a number of the synthetic methods of the invention, which methods allow for the preparation of a vast number of novel cyclic structures (e.g. macrolide compounds) that are inaccessible from biosynthetically derived erythromycinoids. Many of these macrolide structures should have useful biological properties (e.g. antiinfective, antiinflammatory, or anticancer properties) like other known macrolide compounds.

Scheme 1

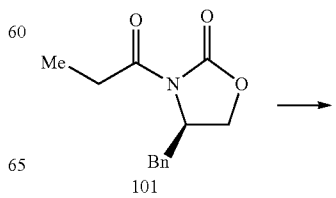

101

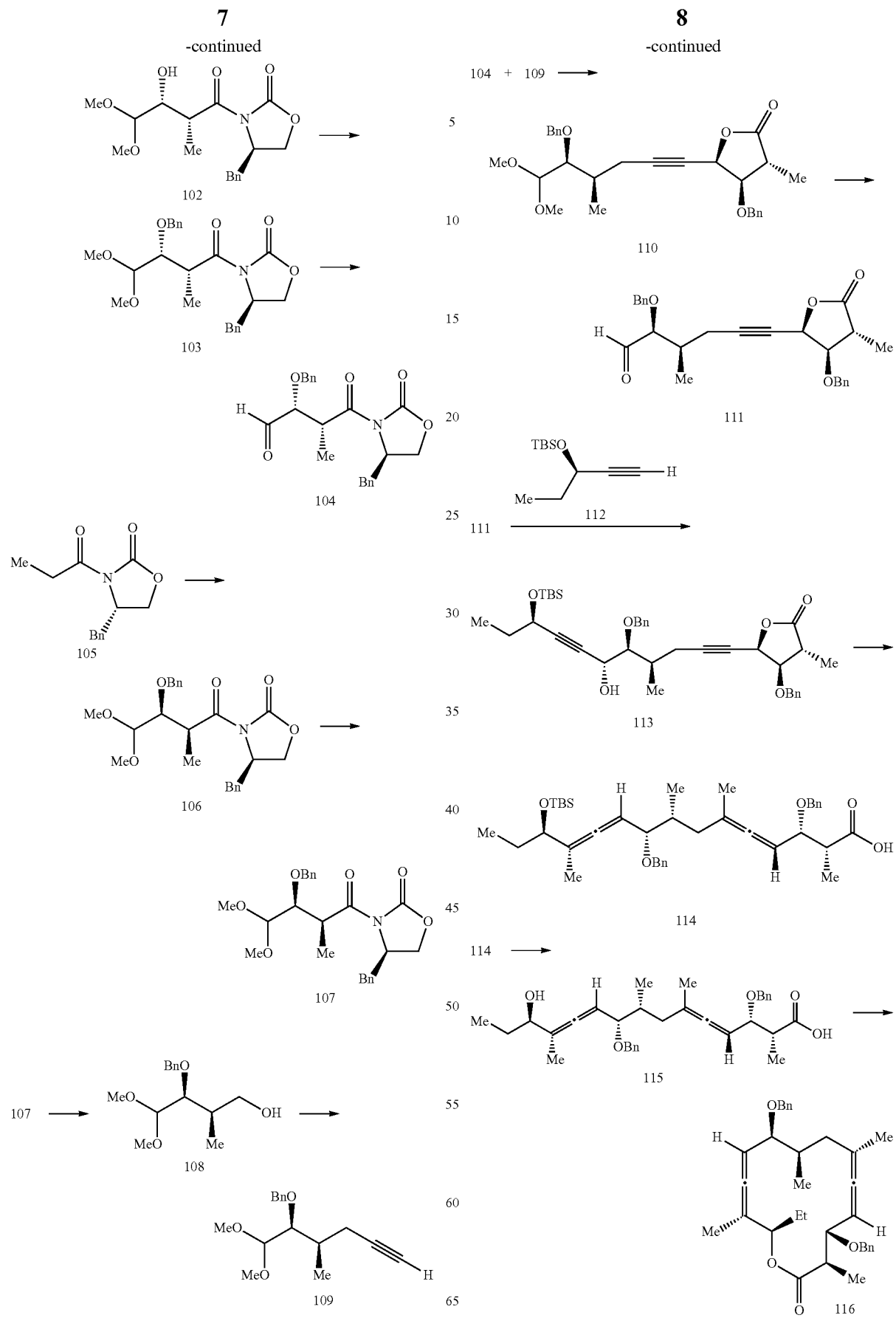

Preparative Examples

Preparative Example 1

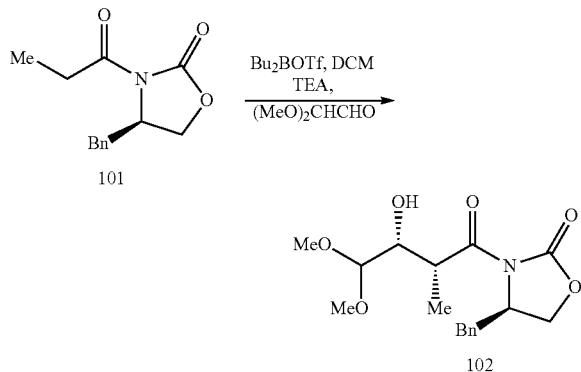

The 4(R)-benzyl propionyl oxazolidinone 101 (16 g, 68.6 mmol) was dissolved in anhydrous DCM (343 ml). To this solution was added di-nbutylboron triflate (75 ml, 75 mmol) and triethylamine (TEA) (9.72 g, 96 mmol) slowly at −78° C. The reaction mixture was then warmed to 0° C. and stirred at that temperature for 1 hour then cooled back to −78° C. A DCM solution (1.0 M) of 1,1-dimethoxy acetaldehyde (100 ml, 100 mmol) was added to the reaction mixture slowly at −78° C. then the resulting solution was slowly warmed to 0° C. over 1 hour and stirred for 1 hour at that temperature. The reaction was then quenched with 100 ml solution of methanol and phosphate buffer (1:3 ratio) at 0° C., followed by addition of 100 ml solution of 30% $H_2O_2$ and methanol (1:2 ratio). The reaction was then stirred for 10 minutes at 0° C. Diluted with 200 ml DCM, washed with cold water (2×100 ml). Organic layer was separated and dried over anhydrous $Na_2SO_4$, then concentrated down to dryness under reduced pressure. Flash column chromatography using 40% EtOAc in hexane gave aldol product 102 as white solid (20.9 g, 90% yield). $[\alpha]^{25}_D$=−51.5 (c=0.01, CHCl$_3$); IR $v_{max}$ (neat)/cm$^{-1}$ 3485, 2937, 1778, 1696, 1386; $^1$H NMR (500 MHz, CDCl$_3$) δ 7.35-7.25 (m, 3H), 7.21 (d, J=7.0 Hz, 2H), 4.72-4.65 (m, 1H), 4.33 (d, J=6.0 Hz, 1H), 4.23-4.15 (m, 2H), 4.05-3.96 (m, 1H), 3.42 (s, 3H), 3.38 (s, 3H), 3.26 (dd, J=13.5, 3.5 Hz, 1H), 2.78 (dd, J=13.5, 10 Hz, 1H), 2.68-2.60 (bs, 1H), 1.32 (d, J=7.0 Hz, 3H); $^{13}$C NMR (125 MHz, CDCl$_3$) δ 176.1, 153.2, 135.4, 129.6 (2), 129.1 (2), 127.5, 104.9, 71.4, 66.3, 55.4, 54.9, 54.4, 39.2, 38.1, 12.8; m/z (ESIMS) found: 360.2 (M+Na)$^+$. calc'd: 360.2.

Preparative Example 2

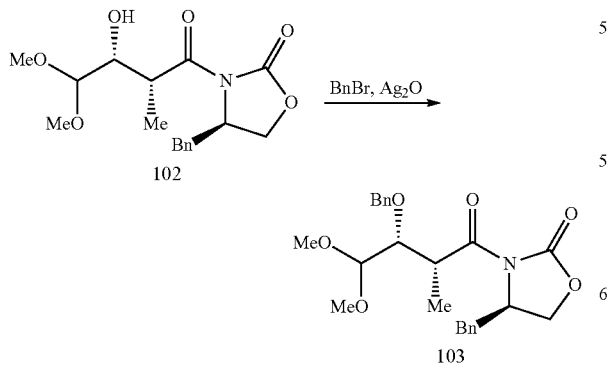

To a suspension of 4 Å powdered molecular sieve (20 g) and Ag$_2$O (35 g, 151 mmol) in anhydrous DCM (250 ml) were added a solution of aldol product 102 (17 g, 50.4 mmol) in DCM (50 ml). Stirred for 10 minutes at room temperature then BnBr (18.5 g, 108 mmol) was added. The reaction mixture was then stirred thoroughly for 2 days under argon in the darkness at room temperature, then filtered over a short column of celite. The solid residue was rinsed with DCM (3×100 ml). The organic filtrate was concentrated down to dryness under reduced pressure, flash column chromatography using 20% EtOAc in hexane gave compound 103 as colorless oil (19.5 g, 91% yield). $[\alpha]^{25}_D$=−22.0 (c=0.01, CHCl$_3$); IR $v_{max}$ (neat)/cm$^{-1}$ 2934, 1778, 1698, 1383, 1107; $^1$H NMR (500 MHz, CDCl$_3$) δ 7.39-7.23 (m, 8H), 7.19 (d, J=7.0 Hz, 2H), 4.81 (d, J=11.5 Hz, 1H), 4.64 (d, J=11.5 Hz, 1H), 4.59-4.53 (m, 1H), 4.34 (d, J=6.0 Hz, 1H), 4.14-4.03 (m, 3H), 3.84 (dd, J=7.5, 6.5 Hz, 1H), 3.43 (s, 3H), 3.34 (s, 3H), 3.24 (dd, J=13.5, 3.5 Hz, 1H), 2.75 (dd, J=13.5, 9.5 Hz, 1H), 1.31 (d, J=7.0 Hz, 3H); $^{13}$C NMR (125 MHz, CDCl$_3$) δ 175.2, 153.3, 138.6, 135.5, 129.6 (2), 129.0 (2), 128.4 (2), 128.2 (2), 127.8, 127.4, 107.0, 79.8, 74.4, 66.1, 55.5, 54.4, 55.2, 39.5, 38.1, 13.8; m/z (ESIMS) found: 450.2 (M+Na)$^+$. calc'd: 450.2.

Preparative Example 3

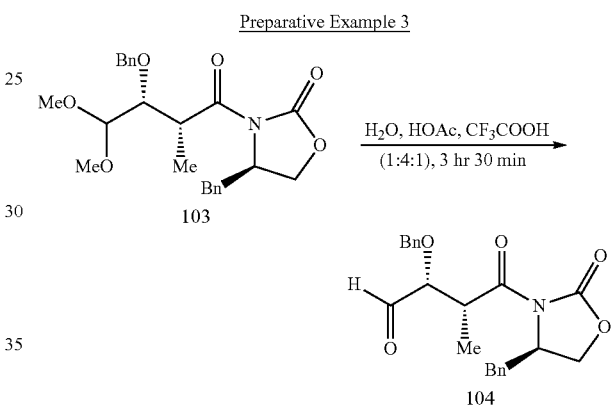

Benzyl protected aldol product 103 (1 g, 2.34 mmol) was dissolved in 10 ml water:acetic acid:trifluoroacetic acid=1:4:1 mixed solution at room temperature for 3 hrs 30 mins. The acidic solution was azeotroped with toluene (5×20 ml) and resulting crude product was taken into the next step immediately without further purification. It could also be further purified by flash column chromatography using 15% EtOAc in hexane gave 104 as colorless viscous oil (847 mg, 95% yield). IR $v_{max}$ (neat)/cm$^{-1}$ 11778, 1730, 1693, 1390, 1212; $^1$H NMR (500 MHz, CDCl$_3$) δ 9.81 (s, 1H), 7.38-7.22 (m, 8H), 7.17 (d, J=7.0 Hz, 2H), 4.75 (d, J=12.5 Hz, 1H), 4.64-4.54 (m, 1H), 4.59 (d, J=12.5 Hz, 1H), 4.32-4.24 (m, 1H), 4.16-4.06 (m, 2H), 3.92 (d, J=6.0 Hz, 1H), 3.20 (dd, J=13.5, 3.5 Hz, 1H), 2.76 (dd, J=13.5, 10 Hz, 1H), 1.33 (d, J=7.0 Hz, 3H); $^{13}$C NMR (125 MHz, CDCl$_3$) δ 202.0, 173.8, 153.1, 137.2, 135.1, 129.6 (2), 129.1 (2), 128.7 (2), 128.4, 128.3 (2), 127.5, 83.3, 73.1, 66.4, 55.4, 41.5, 37.8, 13.4; m/z (ESIMS) found: 404.2 (M+Na)$^+$. calc'd: 404.2.

Preparative Example 4

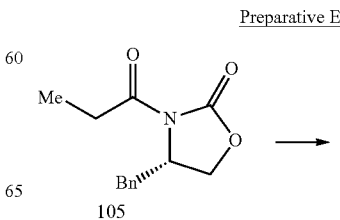

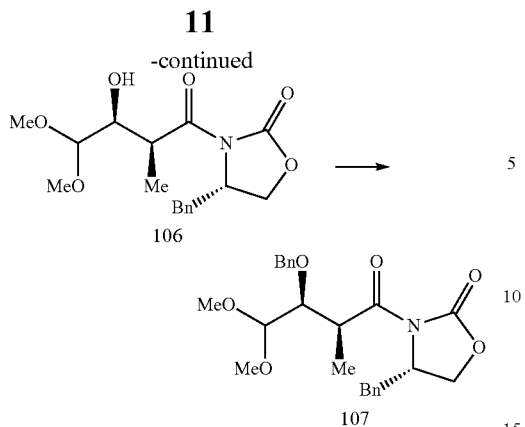

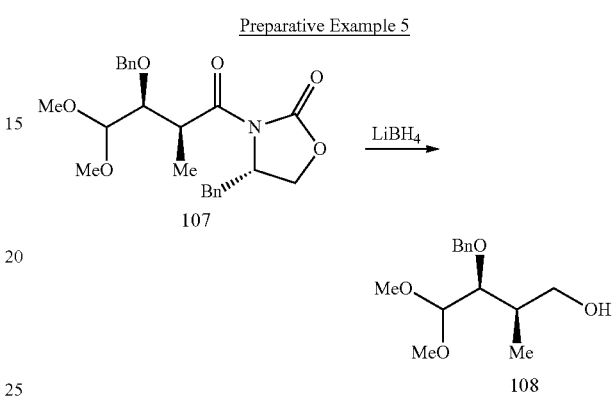

Compound 106 and 107 could be synthesized by using the same procedure used for the synthesis of compound 102 and 103, respectively.

To a solution of 4(S)-benzyl N-propionyl oxazolidinone 105 (16.0 g, 68.6 mmol) in dichloromethane (DCM) (343 mL) was added dibutylboron triflate (75.0 mL, 75.0 mmol) and triethylamine (TEA) (9.72 g, 96.0 mmol) sequentially at −78° C. The reaction mixture was then warmed to 0° C. and stirred for 1 h then cooled back to −78° C. A DCM solution (1.0 M) of 1,1-dimethoxy acetaldehyde (100 mL, 100 mmol) was added to the reaction mixture slowly at −78° C. The mixture was slowly warmed to 0° C. over 1 h and then stirred for 1 h. The reaction was then quenched with 100 mL solution of methanol and pH=7.4 phosphate buffer (1:3 ratio) at 0° C., followed by addition of 100 mL solution of 30% $H_2O_2$ and methanol (1:2 ratio). The mixture was then stirred for 10 min at 0° C. then diluted with 200 mL DCM. The organic layer was separated, washed with water (2×100 mL), dried over anhydrous $Na_2SO_4$, filtered, and then concentrated under reduced pressure to give the crude product, which was purified by flash column chromatography using 40% ethyl acetate in hexane to afford aldol product 106 as white crystalline (20.9 g, 90% yield). $[\alpha]^{25}_D$=+50.0 (c=0.01, $CHCl_3$); M.P. 67° C.; IR $\nu_{max}$ (neat)/cm$^{-1}$ 3485, 2937, 1778, 1696, 1386; $^1$H NMR (500 MHz, $CDCl_3$) δ 7.35-7.25 (m, 3H), 7.21 (d, J=7.0 Hz, 2H), 4.72-4.65 (m. 1H), 4.33 (d, J=6.0 Hz, 1H), 4.23-4.15 (m, 2H), 4.05-3.96 (m, 1H), 3.42 (s, 3H), 3.38 (s, 3H), 3.26 (dd, J=13.5, 3.5 Hz, 1H), 2.78 (dd, J=13.5, 10 Hz, 1H), 2.68-2.60 (bs, 1H), 1.32 (d, J=7.0 Hz, 3H); $^{13}$C NMR (125 MHz, $CDCl_3$) δ 176.1, 153.2, 135.4, 129.6 (2), 129.1 (2), 127.5, 104.9, 71.4, 66.3, 55.4, 54.9, 54.4, 39.2, 38.1, 12.8; MS (ESI+) calculated for $[C_{17}H_{23}NO_6+Na]^+$: 360.2. found: 360.2.

Powdered 4 Å molecular sieves (20.0 g) and $Ag_2O$ (35.0 g, 151 mmol) were combined under inert atmosphere (glove bag) and then taken up in anhydrous DCM (150 mL) followed by addition of 106 (17.0 g, 50.4 mmol) in anhydrous DCM (100 mL). After stirring for 10 min at room temperature (rt) BnBr (18.5 g, 108 mmol) was added to this heterogeneous mixture. The system was then wrapped in aluminum foil and stirred for 2 days under inert atmosphere in the dark at rt. The mixture was then filtered over celite and the solid residue was rinsed with DCM (3×100 mL). The organic filtrate was concentrated under reduced pressure to give crude product, which was purified by flash column chromatography using 20% ethyl acetate in hexane to afford 107 as a colorless oil (20.4 g, 95% yield). $[\alpha]^{25}_D$=+21.0 (c=0.01, $CHCl_3$); IR $\nu_{max}$ (neat)/cm$^{-1}$ 2934, 1778, 1698, 1383, 1107; $^1$H NMR (500 MHz, $CDCl_3$) δ 7.39-7.23 (m, 8H), 7.19 (d, J=7.0 Hz, 2H), 4.81 (d, J=11.5 Hz, 1H), 4.64 (J=11.5 Hz, 1H), 4.59-4.53 (m, 1H), 4.34 (d, J=6.0 Hz, 1H), 4.14-4.03 (m, 3H), 3.84 (dd, J=7.5, 6.5 Hz, 1H), 3.43 (s, 3H), 3.34 (s, 3H), 3.24 (dd, J=13.5, 3.5 Hz, 1H), 2.75 (dd, J=13.5, 9.5 Hz, 1H), 1.31 (d, J=7.0 Hz, 3H); $^{13}$C NMR (125 MHz, $CDCl_3$) δ 175.2, 153.3, 138.6, 135.5, 129.6 (2), 129.0 (2), 128.4 (2), 128.2 (2), 127.8, 127.4, 107.0, 79.8, 74.4, 66.1, 55.5, 55.4, 55.2, 39.5, 38.1, 13.8; MS (ESI+) calculated for $[C_{24}H_{29}NO_6+Na]^+$: 450.2. found: 450.2.

The observed optical rotation ($[\alpha]^{25}_D$) for the compound 106 and 107 are +50.0 (c=0.01, $CHCl_3$), and +21.0 (c=0.01, $CHCl_3$) respectively.

Preparative Example 5

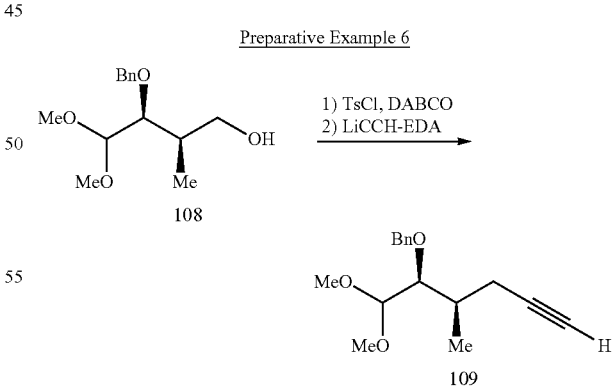

Compound 107 (17.8 g, 41.6 mmol) was dissolved in diethyl ether (200 ml), then 5 ml methanol was added. The reaction mixture was cooled to 0° C. and then added 2.5 M THF solution of $LiBH_4$ (33.2 ml, 83 mmol) slowly. Stirred at 0° C. for 2 hours then quenched with aqueous $NH_4Cl$ (50 ml), extracted with ethyl acetate (3×200 ml). Organic layer combined then dried over anhydrous $Na_2SO_4$, then concentrated down to dryness under reduced pressure. Flash column chromatography using 15% EtOAc in hexane gave 108 as colorless oil (10.3 g, 97% yield). IR $\nu_{max}$ (neat)/cm$^{-1}$ 13431, 2934, 1454, 1071; $^1$H NMR (500 MHz, $CDCl_3$) δ 7.38-7.32 (m, 4H), 7.30-7.25 (m, 2H), 4.82 (d, J=11.5 Hz, 1H), 4.58 (d, J=11.5 Hz, 1H), 4.39 (d, J=6.5 Hz, 1H), 3.59 (dd, J=6.0, 3.5 Hz, 1H), 3.59-3.46 (m, 2H), 3.49 (s, 3H), 3.41 (s, 3H), 2.02-1.96 (m, 1H), 1.90 (bs, 1H), 0.94 (d, J=7.0 Hz, 3H); $^{13}$C NMR (125 MHz, $CDCl_3$) δ 138.9, 128.5 (2), 128.2 (2), 127.8, 106.5, 79.6, 74.1, 65.8, 56.2, 54.6, 36.9, 11.4; m/z (ESIMS) found: 277.2 (M+Na)$^+$. calc'd: 277.2.

Preparative Example 6

Primary alcohol 108 (7.3 g, 28.7 mmol) was dissolved in anhydrous DCM (150 ml), then added diazabicyclo[2.2.2]octane (DABCO) (3.22 g, 28.7 mmol). Cooled to 0° C. and to that tosyl chloride (5.47 g, 28.7 mmol) was added. The reaction mixture was then warmed up to room temperature and stirred for 1 hour. The reaction was then diluted with 150 ml of DCM, washed with saturated $NH_4Cl$ solution (3×50 ml), water (50 ml). Organic layer combined and dried over anhydrous Na₂SO₄ then concentrated down to dryness to give the crude tosylate, which could be used for the next step immediately without further purification. This tosylate was then dissolved in anhydrous dimethyl sulfoxide (DMSO) (70 ml), and to that lithium acetylide-ethylenediamine (4.76 g, 52.9 mmol) solution in 30 ml DMSO was added at once. The reaction was stirred for 3 hours at room temperature, then cooled to 10° C. Quenched carefully with aqueous NH₄Cl (50 ml), diluted with ethyl acetate (300 ml), washed with water (3×100 ml) and dried over anhydrous Na₂SO₄, then concentrated down to dryness under reduced pressure. Flash column chromatography using 5% EtOAc in hexane gave 109 as colorless oil (5.38 g, 78% yield). IR $v_{max}$ (neat)/cm⁻¹ 3295, 2935, 2116, 1096; ¹H NMR (500 MHz, CDCl₃) δ 7.38-7.30 (m, 4H), 7.28-7.22 (m, 1H), 4.68 (d, J=11.5 Hz, 1H), 4.56 (d, J=11.5 Hz, 1H), 4.36 (d, J=7.0 Hz, 1H), 3.65 (dd, J=7.0, 3.0 Hz, 1H), 3.47 (s, 3H), 3.38 (s, 3H), 2.23-2.12 (m, 2H), 2.10-2.00 (m, 1H), 1.96 (t, J=7.5 Hz, 1H), 0.98 (d, J=7.0 Hz, 3H); ¹³C NMR (125 MHz, CDCl₃) δ 139.3, 128.4 (2), 127.9 (2), 127.6, 106.4, 83.7, 80.3, 74.8, 69.6, 56.0, 53.8, 34.4, 23.5, 14.0; m/z (ESIMS) found: 285.1 (M+Na)⁺. calc'd: 285.2.

Preparative Example 7

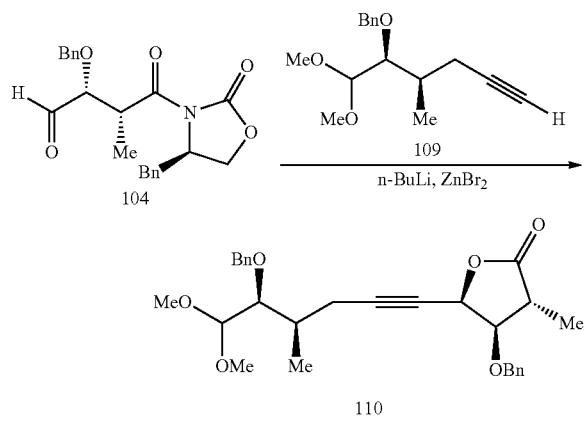

Alkyne 109 (2.04 g, 7.76 mmol) was dissolve in diethyl ether (40 ml) then cooled to −78° C. To that was added n-BuLi (3.10 ml, 7.76 mmol) slowly. The reaction mixture was stirred at −78° C. for 1 hour and added a solution of ZnBr₂ (1.75 g, 7.76 mmol) in diethyl ether (20 ml). The reaction was stirred for 10 mins then warmed to 0° C. and to that a solution of aldehyde 104 (0.8 g, 2.1 mmol) in diethyl ether (15 ml) was added drop wise over 1 hour. The reaction was then stirred for another 10 hours then quenched with aqueous NH₄Cl (50 ml) at 0° C., diluted with ethyl acetate (200 ml), washed with water (2×50 ml) and dried over Na₂SO₄. Organic layer was combined then concentrated down to dryness to give the crude product (8:1 ratio by ¹H NMR). Flash column chromatography using 10% EtOAc in hexane gave major isomer 110 as colorless oil (570 mg, 58% yield). IR $v_{max}$ (neat)/cm⁻¹ 2935, 2238, 1786, 1454; ¹H NMR (500 MHz, CDCl₃) δ 7.38-7.24 (m, 10H), 5.12 (td, J=2.0, 6.5 Hz, 1H), 4.82 (d, J=11.5 Hz, 1H), 4.72 (d, J=12.0 Hz, 1H), 4.53 (d, J=11.5 Hz, 1H), 4.51 (d, J=11.5 Hz, 1H), 3.88 (dd, J=9.5, 6.5 Hz, 1H), 3.57 (dd, J=10.0, 7.0 Hz, 1H), 3.47 (s, 3H), 3.37 (s, 3H), 2.86-2.76 (m, 1H), 2.38-2.20 (m, 2H), 2.10-2.00 (m, 1H), 1.25 (d, J=7.0 Hz, 3H), 0.99 (d, J=7.0 Hz, 3H); ¹³C NMR (125 MHz, CDCl₃) δ 176.0, 139.1, 137.1, 128.8 (2), 128.5 (2), 128.4, 128.1 (2), 127.9 (2), 127.7, 106.4, 95.0, 81.0, 80.5, 74.7, 73.9, 72.4, 70.5, 56.1, 54.1, 39.4, 34.4, 24.0, 14.0, 12.7; m/z (ESIMS) found: 489.3 (M+Na)⁺. calc'd: 489.2.

Preparative Example 8

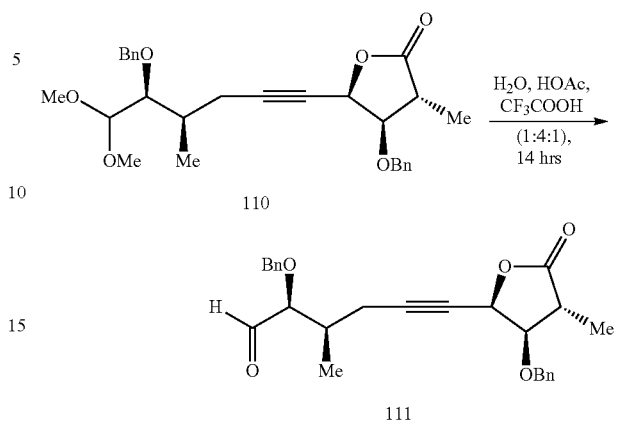

Alkyne 110 (280 mg, 0.6 mmol) was dissolved in 20 ml mixed solution of acetic acid, TFA and water (4:1:1) at room temperature and stirred for 14 hours. The solvent was azeotroped with toluene (5×100 ml) to give a crude product which could be used for the next step without further purification. It could also be further purified by flash column chromatography using 12% EtOAc in hexane gave 111 as colorless viscous oil (215 mg, 85% yield). IR $v_{max}$ (neat)/cm⁻¹ 2935, 2240, 1786, 1730, 1455; ¹H NMR (500 MHz, CDCl₃) δ 9.65 (s, 1H), 7.4-7.25 (m, 10H), 5.11 (d, J=6 Hz, 1H), 4.67 (d, J=13 Hz, 2H), 4.54 (d, J=11.5 Hz, 1H), 4.46 (d, J=12 Hz, 1H), 3.95-3.85 (m, 2H), 2.85-2.75 (m, 1H), 2.48-2.26 (m, 2H), 2.26-2.16 (m, 1H), 1.27 (d, J=7.0 Hz, 3H), 1.01 (d, J=6.5 Hz, 3H); ¹³C NMR (125 MHz, CDCl₃) δ 204.3, 175.9, 137.6, 137.1, 128.8 (2), 128.7 (2), 128.5, 128.3, 128.2 (2), 128.0 (2), 89.2, 85.1, 81.0, 74.9, 73.4, 72.4, 70.4, 39.4, 35.2, 23.1, 14.5, 12.7; m/z (ESIMS) found: 443.2 (M+Na)⁺. calc'd: 443.2.

Preparative Example 9

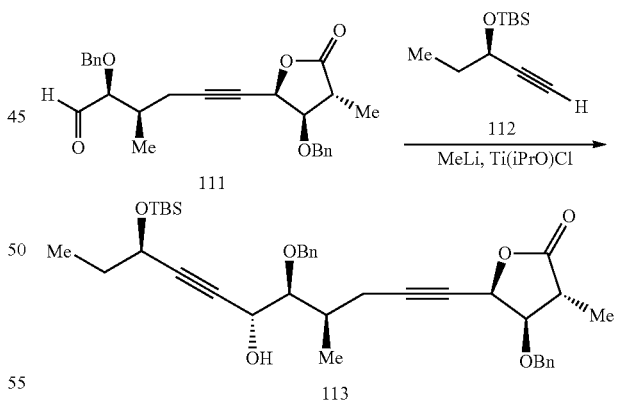

A solution of alkyne 112 (594 mg, 3.0 mmol) in THF (25 ml) was cooled to −78° C. and to that MeLi (1.4 ml, 2.25 mmol) was added slowly. The reaction mixture was stirred for 30 mins and to that a 1 M hexane solution of chlorotriisopropoxyltitanium (IV) (3.0 ml, 3.0 mmol) was added. The reaction was stirred for 1 hour and to that a solution of aldehyde 111 (315 mg, 0.749 mmol) in THF (10 ml) was added slowly at −78° C. The reaction was then warmed slowly to room temperature over 2 hours. The reaction was then diluted with ethyl acetate (200 ml), washed with water (50 ml) and dried over anhydrous Na$_2$SO$_4$. Evaporation of the organic filtrate gave crude product (6:1 ratio by $^1$H NMR) which upon further purification by flash column chromatography using 10% EtOAc in hexane gave major isomer of 113 as colorless oil (411 mg, 89% combined yield for both diastereomers). $^1$H NMR (300 MHz, CDCl$_3$) δ 7.16-7.44 (m, 10H), 5.11 (td, J=2.1 Hz, 6.0 Hz, 1H), 4.76 (d, J=12.0 Hz, 1H), 4.72 (d, J=12.0 Hz, 1H), 4.58 (d, J=12.0 Hz, 1H), 4.53 (d, J=12.0 Hz, 1H), 4.43-4.54 (m, 1H), 4.32 (t, J=6.6 Hz, 1H), 3.87 (dd, J=9.6, 6.6 Hz, 1H), 3.58 (dd, J=5.4, 5.4 Hz, 1H), 2.88-2.76 (m, 1H), 2.46-2.13 (m, 1H), 1.75-1.60 (m, 1H), 1.24 (d, J=7.2 Hz, 3H), 1.06 (d, J=6.9 Hz, 3H), 0.87 (s, 9H), 0.08 (s, 3H), 0.10 (s, 3H).

Preparative Example 10

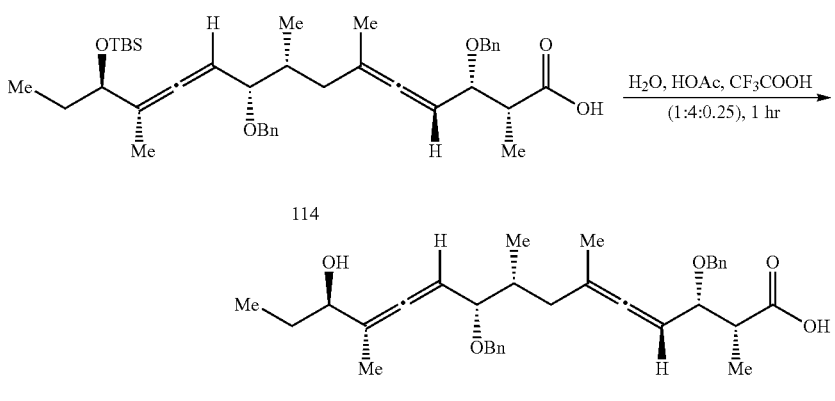

To a solution of 113 (1.2369 g, 1.999 mmol) in 25 ml diethyl ether was added TEA (303 mg, 3 mmol) and methanesulfonyl chloride (MsCl) (343 mg, 3 mmol) respectively at 0° C. The reaction mixture was warmed to rt and stirred for 1 hr 20 min at rt. The mesylate solution was added a solution of methyl cyanocuprate, prepared from CuCN (1.074 g, 11.99 mmol) and MeLi (7.49 ml, 11.99 mmol) in 59.95 ml Et$_2$O at −35° C. The reaction mixture was then warmed to rt and stirred for 1 h. The reaction was then quenched with aqueous NH$_4$Cl (50 ml), extracted in diethyl ether (3×100 ml), washed with water (100 ml), dried over anhydrous MgSO$_4$. Evaporation of solvent gave crude product 114 (1.050 g, 1.659 mmol, 83% yield) and proceeded to the next step without flash column chromatography. [α]$^{25}_D$=+47 (c=0.01, CHCl$_3$); IR ν$_{max}$ (neat)/cm$^{-1}$ 12929, 1965, 1710, 1456, 1066; $^1$H NMR (500 MHz, CDCl$_3$) δ 7.36-7.26 (m, 10H), 5.05-4.90 (m, 2H), 4.70 (d, J=11.5 Hz, 1H), 4.69 (d, J=11.5 Hz, 1H), 4.43 (d, J=11.5 Hz, 1H), 4.39 (d, J=12.0 Hz, 1H), 4.03 (dd, J=8.0 Hz, 6.0 Hz, 1H), 4.00 (t, J=6.0 Hz, 1H), 3.66 (dd, J=9.5, 5.5 Hz, 1H), 2.84-2.72 (m, 1H), 2.42-2.32 (m, 1H), 1.95-1.85 (m, 1H), 1.72 (d, J=3.0 Hz, 3H), 1.65 (d, J=3.0 Hz, 3H), 1.60-1.50 (m, 2H), 1.24 (d, J=7.0 Hz, 3H), 0.98 (d, J=6.5 Hz, 3H), 0.88 (s, 9H), 0.85 (t, J=7.5 Hz, 3H), 0.02 (s, 3H), 0.00 (s, 3H); $^{13}$C NMR (125 MHz, CDCl$_3$) δ 203.9, 202.9, 177.0, 138.9, 137.8, 128.6 (2), 128.5 (2), 128.0 (4), 127.8, 127.6, 102.5, 100.0, 89.7, 87.7, 82.2, 79.8, 75.8, 70.7, 70.2, 37.7, 36.7, 29.5, 26.1 (3), 19.0, 18.4, 15.7, 13.8, 12.9, 10.3, −4.3, −4.8; m/z (ES-IMS) found: 655.4 (M+Na)$^+$. calc'd: 655.4.

The crude Bis[allene] 114 (1.265 g, 1.999 mmol) was dissolved in 75 ml of acetic acid, water, and trifluoroacetic acid mixture (4:1:0.25 ratio) and stirred for 1 hour at rt. The solvent was azeotroped with toluene (3×50 ml) and resulting crude product upon further purification by flash column chromatography using 30% EtOAc in hexane gave 115 as colorless oil (0.881 g, 1.699 mmol, 83% yield). [α]$^{25}_D$=+45.0 (c=0.01, CHCl$_3$); IR ν$_{max}$ (neat)/cm$^{-1}$ 3388, 2933, 1965, 1710, 1454; $^1$H NMR (500 MHz, CDCl$_3$) δ 7.36-7.27 (m, 10H), 5.18-5.10 (m, 1H), 5.08-5.02 (m, 1H), 4.70 (d, J=11.5 Hz, 1H), 4.68 (d, J=12.0 Hz, 1H), 4.45 (d, J=11.5 Hz, 1H), 4.41 (d, J=12.0 Hz, 1H), 4.04 (dd, J=7.0, 7.0 Hz, 1H), 3.99 (t, J=6.5 Hz, 1H), 3.69 (dd, J=8.5, 5 Hz, 1H), 2.84-2.76 (m, 1H), 2.38-2.32 (m, 1H), 1.94-1.84 (m, 1H), 1.75 (d, J=3 Hz, 3H), 1.67 (d, J=2.5 Hz, 3H), 1.66-1.50 (m, 2H), 1.23 (d, J=7 Hz, 3H), 0.98 (d, J=6.5 Hz, 3H), 0.90 (t, J=7 Hz, 3H); $^{13}$C NMR (125 MHz, CDCl$_3$) δ 203.6, 201.7, 175.7, 138.9, 137.7, 128.7 (2), 128.5 (2), 128.1, 128.1 (2), 127.8 (2), 127.7, 103.4, 100.6, 92.5, 88.0, 82.1, 79.3, 74.2, 70.7, 70.4, 44.4, 37.6, 37.0, 27.9, 19.4, 15.4, 15.1, 13.3, 9.8; m/z (ESIMS) found: 541.3 (M+Na)$^+$. calc'd: 541.3.

Preparative Example 12

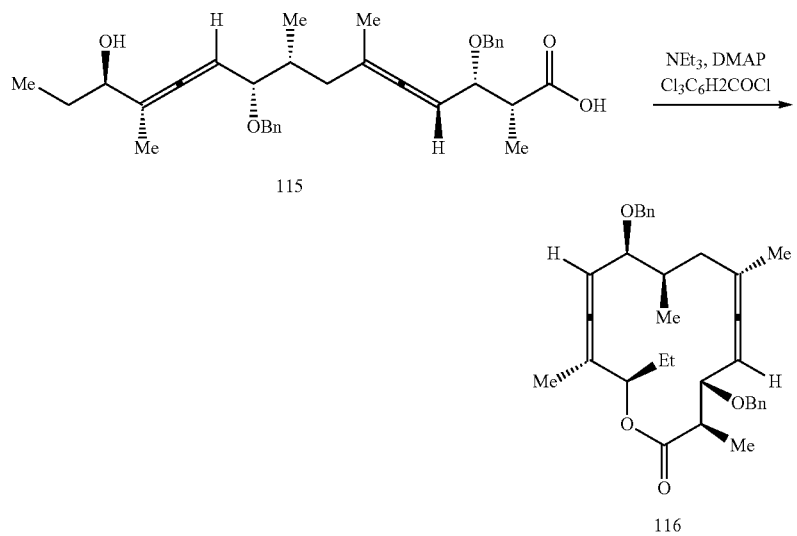

The seco acid 115 (280 mg, 0.54 mmol) was azeotroped with toluene (3×10 ml) and then dissolved in 20 ml toluene. TEA (273 mg, 2.7 mmol) and 2,4,6-trichlorobenzoyl chloride (658 mg, 2.7 mmol) was added to this solution slowly at room temperature then stirred at that temperature for 6 hours. The resulting active ester was then added dropwise over 2 hours to a solution of 4-(N,N-dimethylamino)pyridine (DMAP) (659 mg, 5.4 mmol) in toluene (150 ml) at 80° C. The resulting solution was then cooled back to room temperature and quenched with aqueous NH$_4$Cl (100 ml). The organic layer was washed with water (2×100 ml) and dried over Na$_2$SO$_4$. The organic layer was combined then concentrated down to dryness under reduced pressure. Flash column chromatography using 5% EtOAc in hexanes gave the bis-allenic macrolactone 116 (172 mg, 64% yield) as a colorless oil. $^1$H NMR (500 MHz, CDCl$_3$) δ 7.45-7.29 (m, 8H), 7.29-7.19 (m, 2H), 5.41-5.32 (m, 1H), 5.27 (t, J=6.8 Hz, 1H), 5.19-5.07 (m, 1H), 4.66 (d, J=11.7 Hz, 1H), 4.52 (dd, J=27.5, 11.7 Hz, 2H), 4.35 (d, J=11.8 Hz, 1H), 3.97 (dd, J=8.4, 4.0 Hz, 1H), 3.75 (dd, J=9.3, 5.8 Hz, 1H), 3.55-3.38 (m, 1H), 2.87-2.67 (m, 1H), 2.21 (dd, J=5.3, 2.4 Hz, 1H), 2.18 (t, J=3.9 Hz, 1H), 2.03-1.90 (m, 1H), δ 1.72 (dt, J=5.6, 2.8 Hz, 3H), 1.70-1.65 (m, 1H), 1.65-1.55 (m, 2H), 1.26 (dd, J=7.1, 4.5 Hz, 3H), 1.22 (t, J=7.0 Hz, 1H), 1.06 (d, J=6.7 Hz, 3H), 0.90 (dd, J=13.6, 5.6 Hz, 3H), 0.88-0.86 (m, 1H); $^{13}$C NMR (125 MHz, CDCl$_3$) δ 203.65, 201.41, 174.07, 139.32, 138.80, 128.51, 128.41, 127.98, 127.89, 127.71, 127.49, 102.62, 99.24, 91.99, 90.75, 81.84, 76.99, 75.69, 70.74, 68.93, 45.19, 37.91, 36.10, 25.15, 20.40, 17.89, 15.49, 14.26, 9.85; MS (ESI+) calculated for [C$_{33}$H$_{40}$O$_4$+Na]$^+$: 523.3. found: 523.3.

The invention provides synthetic intermediates and methods that can be used to prepare a wide variety of erythromycinoids (e.g. clarithromycin-, azithromycin-, and ketolide-like medicines). For example, the compounds described herein can be subjected to a variety of standard modifications that are known in the erythromycin and ketolide field (e.g. ketone formation at C3, glycosylation at C5, etherification at the C6 hydroxyl, ketone and/or imine formation at C9, and oxazolidinone formation at C11/C12) to provide compounds with useful biological properties. For example, see Constantin Agouridas et al. *J. Med. Chem.* 1998, 41, 4080-4100; Yat Sun Or et al. *J. Med. Chem.* 2000, 43, 1045-1049; Zhenkun Ma et al. *J. Med. Chem.* 2001, 44, 4137-4156; Robert F. Keyes et al. *J. Med. Chem.* 2003, 46, 1795-1798; Matthew T. Burger et al. *J. Med. Chem.* 2006, 49, 1730-1743; and Thomas V. Magee et al. *J. Med. Chem.* 2009, 52, 7446-7457

Preparative Example 13

In general oxetanones, including oxetanones of the invention, can be prepared from the corresponding allenes as illustrated in General methods A, B, and C as follows.

General Procedure for Oxetan-3-Ones Formation Via Thermal Rearrangement (Method A)

Dimethyldioxirane (DMDO) was prepared following a modified Murray procedure.[1] For a photo of the set up for this procedure see Ref 2. The DMDO in CHCl$_3$ was prepared as described.[3,4]

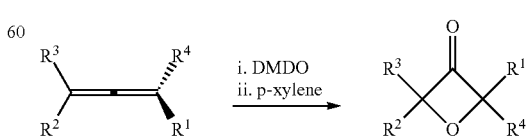

The allene was taken up in CHCl$_3$ (0.10 M) and cooled to −20° C. To this a solution of freshly prepared DMDO in CHCl$_3$ (~0.20 M, 2.0 equiv) was added dropwise. The reaction was stirred under nitrogen. Upon the complete consumption of allene, as judged by TLC (30-120 min), the volatiles were removed under vacuum and the spirodiepoxide (SDE) was azeotropically dried with toluene. The SDE was dissolved in p-xylene (0.01 M) and then transferred to a sealed tube. The SDE in p-xylene was degassed and then heated at 200° C. for 2 h. The reaction was removed from heat and allowed to cool to room temperature. The solvent was removed under reduced pressure and the crude was purified by flash column chromatography.

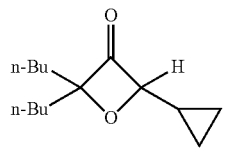

2,2-dibutyl-4-cyclopropyloxetan-3-one

To the solution of allene (52. mg, 0.270 mmol) in CHCl$_3$ (2.70 ml) at −20° C. was added a solution of freshly prepared DMDO in CHCl$_3$ (2.70 ml, 0.54 mmol) dropwise. The reaction was stirred under nitrogen at −20° C. for 45 min. Upon complete consumption of allene as judged by TLC (45 min), the volatiles were removed under vacuum and the SDE was azeotropically dried with toluene. The SDE was dissolved in p-xylene (27.0 ml) and then transferred to a sealed tube. The SDE in p-xylene was degassed and then heated at 200° C. for 2 h. The reaction was removed from heat and allowed to cool to room temperature. The solvent was removed under reduced pressure and the crude was purified by flash column chromatography (2% EtOAc/Hexane) to obtain 2,2-dibutyl-4-cyclopropyloxetan-3-one (49. mg, 81% yield) as colorless oil. IR $v_{max}$ (neat)/cm$^{-1}$ 2957, 2932, 2871, 1812, 1466, 1024, 955; $\delta_H$ (400 MHz, CDCl$_3$) 4.55 (1H, d, J=8.8 Hz), 1.83-1.65 (4H, m), 1.58-1.14 (8H, m), 0.96-0.84 (7H, m), 0.71-0.62 (2H, m), 0.49-0.36 (2H, m); $\delta_C$ (100 MHz, CDCl$_3$) 208.38, 107.76, 101.18, 34.84, 34.81, 25.72, 23.00, 22.94, 13.87, 13.84, 11.22, 2.57, 2.11; m/z (ESIMS) 225.2 (M+H)$^+$.

General Procedure for Oxetan-3-Ones Formation Via Nucleophilic Addition Followed by Nucleophilic Substitution (Method B)

Dimethyldioxirane (DMDO) was prepared following a modified Murray procedure. The DMDO was extracted out of acetone and into CHCl$_3$ by known procedure.

The allene was taken upon CHCl$_3$ (0.10 M) and cooled to −20° C. To this was added solution of freshly prepared DMDO in CHCl$_3$ (~0.20 M, 2.0 equiv) dropwise. The reaction was stirred under nitrogen. Upon the complete consumption of allene as judged by TLC (30-120 min), the volatiles were removed under vacuum and the SDE was azeotropically dried with toluene. The freshly prepared SDE was dissolved in THF (0.20 M) and cooled to 0° C. To the SDE in THF was added LiBr (1.10 equiv). The reaction was allowed to warm to room temperature. Upon the complete disappearance of the SDE as judged by TLC (4-6 h), the volatiles were removed under vacuum and the reaction mixture was dissolved in DMSO (0.05 M). The reaction mixture was cooled to 0° C. and KOH (1.2 N, 1.1 equiv) was added dropwise. Upon the completion of reaction as judged by TLC (5-10 min), the reaction was diluted with water and the organic layer was extracted in EtOAc, dried over anhydrous Na$_2$SO$_4$, filtered, concentrated and purified by flash column chromatography.

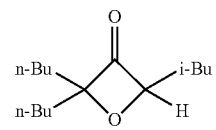

2,2-dibutyl-4-isobutyloxetan-3-one

To the solution of allene (89. mg, 0.427 mmol) in CHCl$_3$ (4.27 ml) at −20° C. was added solution of freshly prepared DMDO in CHCl$_3$ (4.25 ml, 0.85 mmol) dropwise. The reaction was stirred under nitrogen at −20° C. for 30 min. Upon complete consumption of allene as judged by TLC (30 min), the volatiles were removed under vacuum and the SDE was azeotropically dried with toluene. The freshly prepared SDE was dissolved in THF (2.13 ml) and cooled to 0° C. To the SDE in THF was added LiBr (41. mg, 0.470 mmol). The reaction was allowed to warm to rt. Upon the complete disappearance of the SDE as judged by TLC (4 h), the volatiles were removed under vacuum and the reaction mixture was dissolved in DMSO (8.54 ml). The reaction mixture was cooled to 0° C. and KOH (0.390 ml, 0.470 mmol) was added dropwise. Upon the completion of reaction as judged by TLC (10 min), the reaction was diluted with water and the organic layer was extracted in EtOAc (3×5.00 ml), dried over anhydrous Na$_2$SO$_4$, filtered, concentrated and purified by flash column chromatography (2% EtOAc/Hexane) to obtain 2,2-dibutyl-4-isobutyloxetan-3-one (98. mg, 95% yield) as colorless oil. IR $v_{max}$ (neat)/cm$^{-1}$ 2958, 2872, 1811, 1467; 6 (500 MHz, CDCl$_3$) 5.21 (1H, dd, J=8.8, 5.5 Hz), 1.88-1.42 (8H, m), 1.41-1.17 (7H, m), 0.99-0.88 (12H, m); $\delta_C$ (125 MHz, CDCl$_3$) 210.09, 108.20, 95.86, 39.93, 35.28, 35.08, 25.88, 25.80, 25.06, 22.98, 22.95, 22.18, 13.90, 18.86; m/z (ESIMS) 241.2 (M+H)$^+$.

General Procedure for Oxetan-3-Ones Formation Via Electrophilic Addition Followed by NUCLEOPHILIC substitution (Method C)

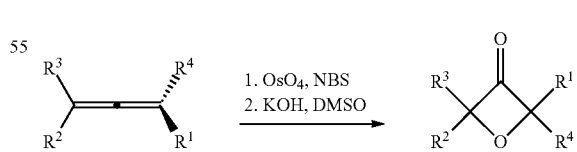

To the allene in 1:1 solution of t-BuOH and pH 7.4 buffer (0.15 M) was added NMO (2.0 equiv) and OsO$_4$ (2.0 equiv) at rt. NBS (2.0 equiv) was dissolved in 1:1:1 solution of t-BuOH, water and acetone (0.15 M with respect to allene) and added to the reaction mixture via syringe pump over 5 h at rt. After the complete consumption of allene as judged by TLC, the reaction was quenched by a saturated solution of sodium sulfite. The reaction was diluted by water and the organic layer was extracted in EtOAc, dried over anhydrous Na₂SO₄, filtered, concentrated and purified by flash column chromatography. The haloketone was dissolved in DMSO (0.05 M) and cooled to 0° C. To the reaction at 0° C. was added KOH (1.2 N, 1.1 equiv) dropwise. Upon the completion of reaction as judged by TLC (5-10 min), the reaction was diluted with water and the organic layer was extracted in EtOAc, dried over anhydrous Na₂SO₄, filtered, concentrated and purified by flash column chromatography.

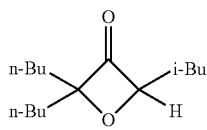

2,2-dibutyl-4-isobutyloxetan-3-one

To the solution of allene (48. mg, 0.230 mmol) in 1:1 solution of t-BuOH and pH 7.4 buffer (3.0 ml) at rt was added NMO (60. mg, 0.460 mmol) and 4 wt % OsO₄ in water (0.300 ml, 0.046 mmol). NBS (77. mg, 0.460 mmol) was dissolved in 1:1:1 solution of t-BuOH, water and acetone (3.00 ml) and added to the reaction mixture via syringe pump over 5 h at rt. After the complete consumption of allene as judged by TLC (5 h), the reaction was quenched by a saturated solution of sodium sulfite (3.00 ml). The reaction was diluted by water and the organic layer was extracted in EtOAc (3×10.0 ml), dried over anhydrous Na₂SO₄, filtered, concentrated and purified by flash column chromatography (4% EtOAc/Hexane) to obtain 4-bromo-6-butyl-6-hydroxy-2-methyldecan-5-one (63. mg, 85% yield) as colorless oil. The 4-bromo-6-butyl-6-hydroxy-2-methyldecan-5-one (63. mg, 0.196 mmol) was dissolved in DMSO (3.92 ml) and cooled to 0° C. To the reaction at 0° C. was added KOH (0.180 ml, 0.216 mmol) dropwise. Upon the completion of reaction as judged by TLC (10 min), the reaction was diluted with water and the organic layer was extracted in EtOAc (3×5.00 ml), dried over anhydrous Na₂SO₄, filtered, concentrated and purified by flash column chromatography (2% EtOAc/Hexane) to obtain 2,2-dibutyl-4-isobutyloxetan-3-one (45. mg, 95% yield) as colorless oil.

In one embodiment the invention provides a method for preparing a macrocyclic ring of formula 2 having an alpha-hydroxy ketone:

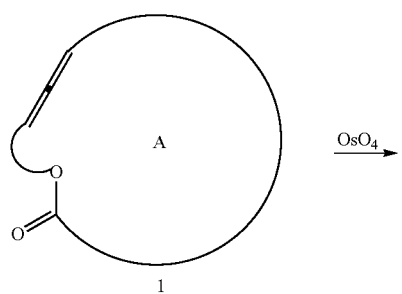

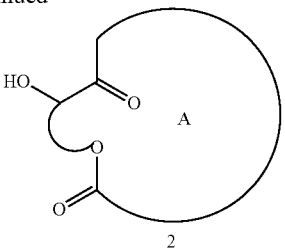

comprising treating a cyclic allene of formula 1 with osmium tetroxide to provide the corresponding macrocyclic ring of formula 2, wherein ring A is a ring comprising 7-19 carbon atoms, which ring is optionally substituted with one or more groups independently selected from halo, hydroxy, carboxy, cyano, $(C_1-C_6)$alkyl, $(C_2-C_6)$alkenyl, $(C_2-C_6)$alkynyl, $(C_1-C_6)$alkoxy, $(C_3-C_6)$cycloalkyl, aryl, aryl$(C_1-C_6)$alkyl, heteroaryl, heteroaryl$(C_1-C_6)$alkyl, aryl$(C_1-C_6)$alkanoyl, heteroaryl$(C_1-C_6)$alkanoyl, and $OR^c$; wherein each $(C_1-C_6)$alkyl, $(C_2-C_6)$alkenyl, $(C_2-C_6)$alkynyl, $(C_1-C_6)$alkoxy, $(C_3-C_6)$cycloalkyl, and $(C_1-C_6)$alkanoyl is optionally substituted with one or more groups independently selected from halo, hydroxy, cyano, nitro, $(C_1-C_6)$alkyl, $(C_1-C_6)$alkoxy, $(C_3-C_6)$cycloalkyl, oxo, carboxy, aryl, heteroaryl, aryloxy, heteroaryloxy, $=N-OR^d$, and $-NR^aR^b$; and wherein each aryl, and heteroaryl is optionally substituted with one or more groups independently selected from halo, hydroxy, cyano, nitro, $(C_1-C_6)$alkyl, $(C_1-C_6)$alkoxy, $(C_3-C_6)$cycloalkyl, carboxy, aryl, heteroaryl, aryloxy, heteroaryloxy, and $-NR^aR^b$; and each $R^a$ and $R^b$ is independently selected from H, $(C_1-C_6)$alkyl, $(C_3-C_6)$cycloalkyl, $(C_3-C_6)$cycloalkyl$(C_1-C_6)$alkyl, aryl, heteroaryl, aryl$(C_1-C_6)$ alkyl and heteroaryl$(C_1-C_6)$ alkyl; or $R^a$ and $R^b$ together with the nitrogen to which they are attached form a aziridino, azetidino, morpholino, piperazino, pyrrolidino or piperidino;

each $R^c$ is independently a saccharide or a hydroxy protecting group; and each $R^d$ is independently selected from H, $(C_1-C_6)$alkyl, $(C_3-C_6)$cycloalkyl, $(C_3-C_6)$cycloalkyl$(C_1-C_6)$alkyl, aryl, heteroaryl, aryl$(C_1-C_6)$ alkyl heteroaryl$(C_1-C_6)$ alkyl and a saccharide.

In one embodiment the invention provides a method for preparing a macrocyclic ring of formula 4 having an alpha-hydroxy ketone:

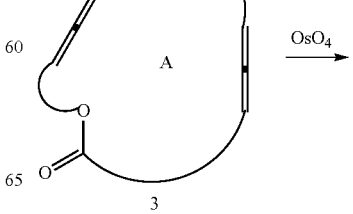

23

-continued

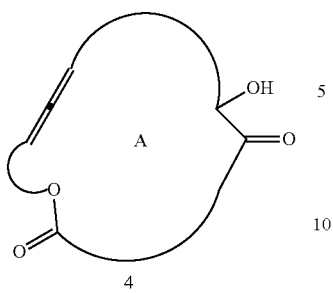

4 comprising treating a cyclic bis-allene of formula 3 with osmium tetroxide to provide the corresponding macrocyclic ring of formula 4, wherein ring A is a ring comprising 7-19 carbon atoms, which ring is optionally substituted with one or more groups independently selected from halo, hydroxy, carboxy, cyano, $(C_1-C_6)$alkyl, $(C_2-C_6)$alkenyl, $(C_2-C_6)$alkynyl, $(C_1-C_6)$alkoxy, $(C_3-C_6)$cycloalkyl, aryl, aryl$(C_1-C_6)$alkyl, heteroaryl, heteroaryl$(C_1-C_6)$alkyl, aryl$(C_1-C_6)$alkanoyl, heteroaryl$(C_1-C_6)$alkanoyl, and $OR^c$; wherein each $(C_1-C_6)$alkyl, $(C_2-C_6)$alkenyl, $(C_2-C_6)$alkynyl, $(C_1-C_6)$alkoxy, $(C_3-C_6)$cycloalkyl, and $(C_1-C_6)$alkanoyl is optionally substituted with one or more groups independently selected from halo, hydroxy, cyano, nitro, $(C_1-C_6)$alkyl, $(C_1-C_6)$alkoxy, $(C_3-C_6)$cycloalkyl, oxo, carboxy, aryl, heteroaryl, aryloxy, heteroaryloxy, and —$NR^aR^b$; and wherein each aryl, and heteroaryl is optionally substituted with one or more groups independently selected from halo, hydroxy, cyano, nitro, $(C_1-C_6)$alkyl, $(C_1-C_6)$alkoxy, $(C_3-C_6)$cycloalkyl, carboxy, aryl, heteroaryl, aryloxy, heteroaryloxy, and —$NR^aR^b$;

each $R^a$ and $R^b$ is independently selected from H, $(C_1-C_6)$alkyl, $(C_3-C_6)$cycloalkyl, $(C_3-C_6)$cycloalkyl$(C_1-C_6)$alkyl, aryl, heteroaryl, aryl$(C_1-C_6)$ alkyl and heteroaryl$(C_1-C_6)$ alkyl; or $R^g$ and $R^h$ together with the nitrogen to which they are attached form a aziridino, azetidino, morpholino, piperazino, pyrrolidino or piperidino; and each $R^c$ is independently a saccharide or a hydroxy protecting group.

In one embodiment the invention provides a method for reducing the alpha-hydroxy ketone of formula 4 to provide the corresponding diol.

In one embodiment the invention provides a method for preparing a macrocyclic ring of formula 6 having two alpha-hydroxy ketones:

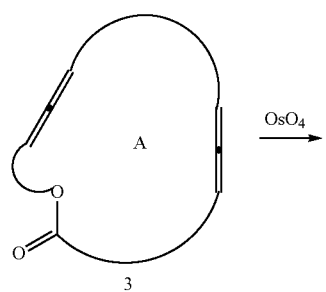

3

24

-continued

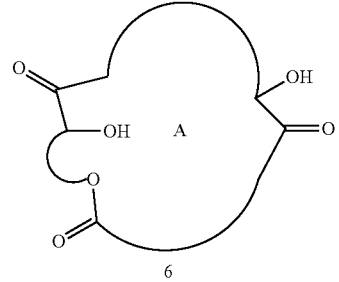

6 comprising treating a cyclic bis-allene of formula 3 with osmium tetroxide to provide the corresponding macrocyclic ring of formula 6, wherein ring A is a ring comprising 7-19 carbon atoms, which ring is optionally substituted with one or more groups independently selected from halo, hydroxy, carboxy, cyano, $(C_1-C_6)$alkyl, $(C_2-C_6)$alkenyl, $(C_2-C_6)$alkynyl, $(C_1-C_6)$alkoxy, $(C_3-C_6)$cycloalkyl, aryl, aryl$(C_1-C_6)$alkyl, heteroaryl, heteroaryl$(C_1-C_6)$alkyl, aryl$(C_1-C_6)$alkanoyl, heteroaryl$(C_1-C_6)$alkanoyl, and $OR^c$; wherein each $(C_1-C_6)$alkyl, $(C_2-C_6)$alkenyl, $(C_2-C_6)$alkynyl, $(C_1-C_6)$alkoxy, $(C_3-C_6)$cycloalkyl, and $(C_1-C_6)$alkanoyl is optionally substituted with one or more groups independently selected from halo, hydroxy, cyano, nitro, $(C_1-C_6)$alkyl, $(C_1-C_6)$alkoxy, $(C_3-C_6)$cycloalkyl, oxo, carboxy, aryl, heteroaryl, aryloxy, heteroaryloxy, and —$NR^aR^b$; and wherein each aryl, and heteroaryl is optionally substituted with one or more groups independently selected from halo, hydroxy, cyano, nitro, $(C_1-C_6)$alkyl, $(C_1-C_6)$alkoxy, $(C_3-C_6)$cycloalkyl, carboxy, aryl, heteroaryl, aryloxy, heteroaryloxy, and —$NR^aR^b$;

each $R^a$ and $R^b$ is independently selected from H, $(C_1-C_6)$alkyl, $(C_3-C_6)$cycloalkyl, $(C_3-C_6)$cycloalkyl$(C_1-C_6)$alkyl, aryl, heteroaryl, aryl$(C_1-C_6)$ alkyl and heteroaryl$(C_1-C_6)$ alkyl; or $R^g$ and $R^h$ together with the nitrogen to which they are attached form a aziridino, azetidino, morpholino, piperazino, pyrrolidino or piperidino; and each $R^c$ is independently a saccharide or a hydroxy protecting group.

In one embodiment the invention provides a method for preparing a compound of formula 8c:

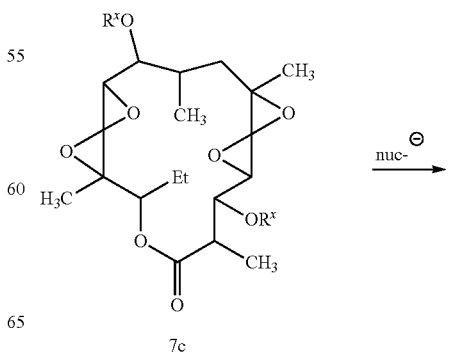

7c

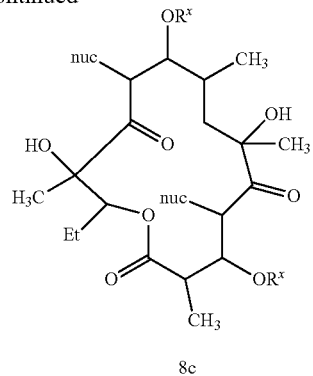

8c wherein each $R^x$ is independently a suitable protecting group comprising treating a compound of formula 7c with a nucleophile (nuc-) to provide the compound of formula 8c. This conversion can be carried out by treatment with any standard nucleophilic reagent under standard conditions. The nucleophilic addition can be carried out at any suitable temperature (e.g. a temperature in the range of about −80° C. to about 60° C. in the presence of a suitable solvent (e.g. a halocarbon solvent such as chloroform, dichloromethane, carbon tetrachloride, trifluoroethanol, or hexane, acetone, t-butanol, water, acetonitrile, dimethylformamide (DMF), dimethylsulfoxide (DMSO), diethylketone (DEK), methyl ethyl ketone (MEK), dimethoxyethane, 1,4-dioxane, or a mixture thereof). In one embodiment of the invention the nucleophilic addition can be carried out by treating the tetraepoxide with LiBr at −5° C. as illustrated in Example 1.

In one embodiment the invention provides a method for preparing a compound of formula 9c:

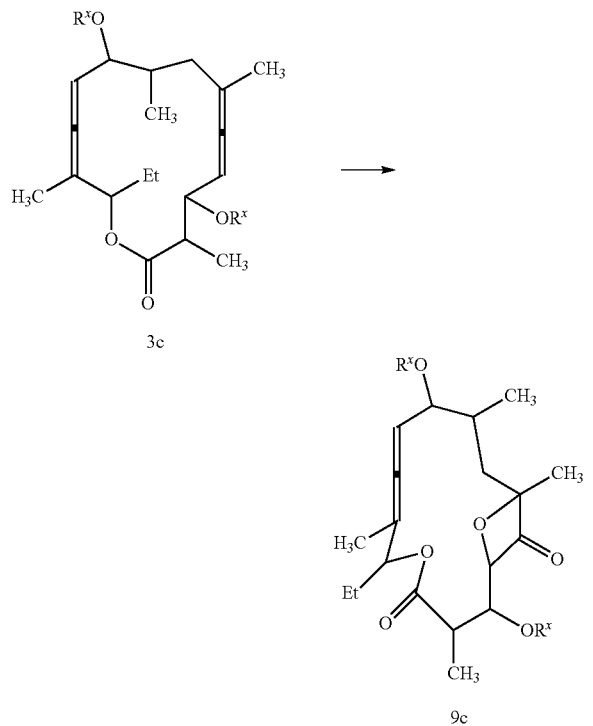

wherein each Rx is independently a suitable protecting group comprising converting a compound of formula 3c to the compound of formula 9c. This conversion can conveniently be carried out using the methods described in Preparative Example 13. For example, this conversion can conveniently be carried out by treatment of the compound of formula 3c with a suitable oxidizing agent (e.g. an epoxidizing agent such as DMDO, methylethyl dioxirane (MEDO), diethyl dioxirane (DEDO), methyl(trifluoromethyl)dioxirane (TFDO), Oxone, Tetraphenylphosphonium Monoperoxysulfate (TPPP), Shi's fructose derived catalyst, Jacobsen's (salen) manganese (III) catalyst, isoquiniline-, biphenyl-, binaphthyl-derived imminium salts, followed by treatment with a nucleophilic source of $CH_3''$. The oxidation can be carried out at any suitable temperature (e.g. a temperature in the range of about −80° C. to about 60° C. Due to the stability of the resulting tetraepoxide, this epoxidation is typically carried out at a temperature in the range of from about −80° C. to about −15° C. The conversion can also be carried out in the presence of a suitable solvent (e.g. a halocarbon solvent such as chloroform, dichloromethane, carbon tetrachloride, trifluoroethanol, or hexane, acetone, t-butanol, water, acetonitrile, dimethylformamide (DMF), dimethylsulfoxide (DMSO), diethylketone (DEK), methyl ethyl ketone (MEK), dimethoxyethane, 1,4-dioxane, or a mixture thereof). In one embodiment of the invention this conversion can be carried out by treating the compound of formula 3c with DMDO at −40.0° C. in chloroform to provide the corresponding tetraepoxide as illustrated in Example 6. The tetraepoxide can subsequently be treated with a nucleophile (e.g. a methyl cuprate) under any suitable conditions. The nucleophilic addition can be carried out at any suitable temperature (e.g. a temperature in the range of about −80° C. to about 60° C.). in the presence of a suitable solvent (e.g. a halocarbon solvent such as chloroform, dichloromethane, carbon tetrachloride, trifluoroethanol, or hexane, acetone, t-butanol, water, acetonitrile, dimethylformamide (DMF), dimethylsulfoxide (DMSO), diethylketone (DEK), methyl ethyl ketone (MEK), 1,2-dimethoxyethane (DME), 1,4-dioxane, or a mixture thereof). In one embodiment of the invention the nucleophilic addition can be carried out by treating the tetraepoxide with MeCu(CN)Li at −15.0° C. as illustrated in Example 6.

In one embodiment the invention provides a method for preparing a compound of formula 8c:

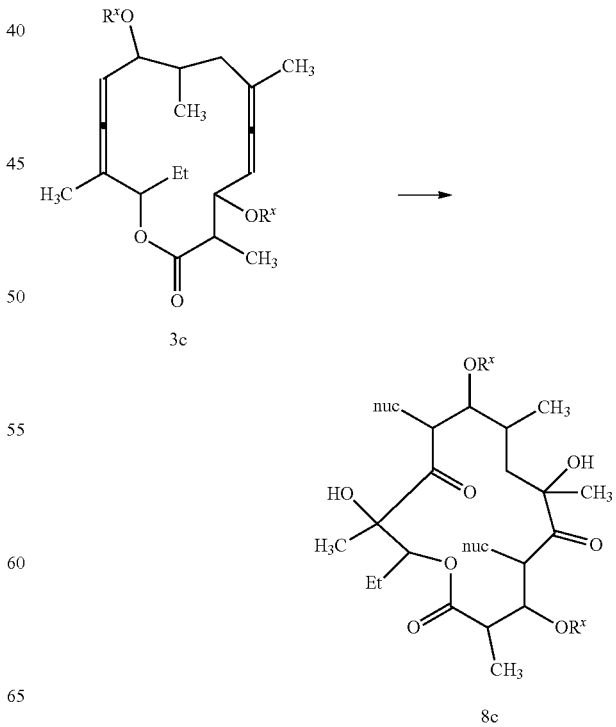

wherein each R[x] is independently a suitable protecting group comprising converting a compound of formula 3c to the compound of formula 8c. This conversion can be carried out by treatment of the compound of formula 3c with a suitable oxidizing agent (e.g. an epoxidizing agent such as DMDO, methylethyl dioxirane (MEDO), diethyl dioxirane (DEDO), methyl(trifluoromethyl)dioxirane (TFDO), Oxone, Tetraphenylphosphonium Monoperoxysulfate (TPPP), Shi's fructose derived catalyst, Jacobsen's (salen) manganese (III) catalyst, isoquiniline-, biphenyl-, binaphthyl-derived imminium salts, followed by treatment with a nucleophile agent. The oxidation can be carried out at any suitable temperature (e.g. a temperature in the range of about −80° C. to about 60° C.). Due to the instability of the resulting tetraepoxide, this epoxidation is typically carried out at a temperature in the range of from about −80° C. to about −30° C. The conversion can also be carried out in the presence of a suitable solvent (e.g. a halocarbon solvent such as chloroform, dichloromethane, carbon tetrachloride, trifluoroethanol, or hexane, acetone, t-butanol, water, acetonitrile, dimethylformamide (DMF), dimethylsulfoxide (DMSO), diethylketone (DEK), methyl ethyl ketone (MEK), dimethoxyethane, 1,4-dioxane, or a mixture thereof). In one embodiment of the invention this conversion can be carried out by treating the compound of formula 117 with DMDO at −40° C. in chloroform to provide the corresponding tetraepoxide as illustrated in Example 1. The tetraepoxide can subsequently be treated with a nucleophile under any suitable conditions. The nucleophilic addition can be carried out at any suitable temperature (e.g. a temperature in the range of about −80° C. to about 60° C. in the presence of a suitable solvent (e.g. a halocarbon solvent such as chloroform, dichloromethane, carbon tetrachloride, trifluoroethanol, or hexane, acetone, t-butanol, water, acetonitrile, dimethylformamide (DMF), dimethylsulfoxide (DMSO), diethylketone (DEK), methyl ethyl ketone (MEK), dimethoxyethane, 1,4-dioxane, or a mixture thereof). In one embodiment of the invention the nucleophilic addition can be carried out by treating the tetraepoxide with LiBr at −5.0° C. as illustrated in Example 1.

In one embodiment the invention provides a method comprising converting the compound of formula 10c:

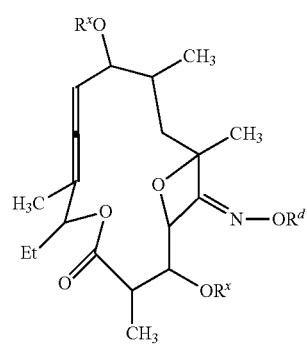

10c wherein each R[x] is independently a suitable protecting group to a corresponding compound of formula 11c:

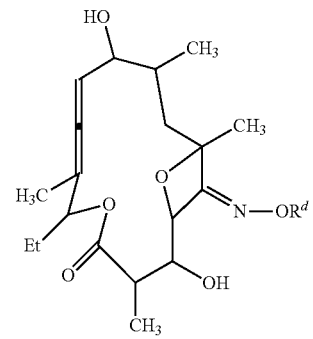

11c wherein each R[d] is independently a H, a saccharide, or a hydroxy protecting group. This conversion can be carried out by treatment of the compound of formula 10c wherein R[x] is benzyl with H₂/Pd—C or H₂/Pd(OH)₂ or Rd/Al₂O₃ or Na/NH₃ or Me₃SiI or SnCl₄. The conversion can be carried out at any suitable temperature (e.g. a temperature in the range of about −80° C. to about 60° C.). The conversion can also be carried out in the presence of a suitable solvent (e.g. a halocarbon solvent such as chloroform, dichloromethane, methanol, ethanol, acetic acid, tetrahydrofurna, diethyl ether, hexane, toluene, or a mixture thereof).

In one embodiment the invention provides a method comprising converting the compound of formula 11c to a corresponding compound of formula 12c:

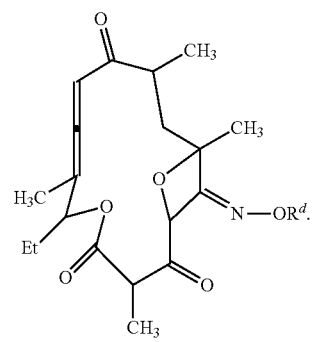

12c wherein each R[d] is independently a H, a saccharide, or a hydroxy protecting group. This oxidation can be carried out by treatment of the compound of formula 11c with a suitable oxidizing agent (e.g. pyridinium chlorochromate (PCC), Swern, Dess-Martin Periodinate (DMP), or Tetrapropylammonium Perruthenate (TPAP)) at any suitable temperature (e.g. a temperature in the range of about −80° C. to about room temperature. The conversion can also be carried out in the presence of a suitable solvent (e.g. a halocarbon solvent such as dichloromethane or DMSO, or a mixture thereof).

In one embodiment the invention provides a method comprising converting a compound of formula 12c:

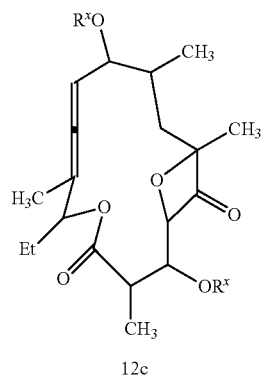

12c

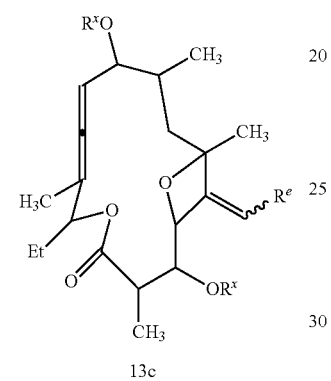

13c wherein each Rx is independently a suitable protecting group to a corresponding compound of formula 13c, wherein each $R^e$ is independently halo, nitro, carboxy, cyano, $(C_1-C_6)$alkyl, $(C_2-C_6)$alkenyl, $(C_2-C_6)$alkynyl, $(C_3-C_6)$cycloalkyl, $(C_1-C_6)$alkanoyl, $(C_1-C_6)$alkoxycarbonyl, $-SO_2R^f$, and $(C_3-C_6)$cycloalkylcarbonyl; wherein each $(C_1-C_6)$alkyl, $(C_2-C_6)$alkenyl, $(C_2-C_6)$alkynyl, $(C_3-C_6)$cycloalkyl, $(C_1-C_6)$alkanoyl, $(C_1-C_6)$alkoxycarbonyl, $-SO_2R^f$, and $(C_3-C_6)$cycloalkylcarbonyl is optionally substituted with one or more groups independently selected from halo, hydroxy, cyano, nitro, $(C_1-C_6)$alkyl, $(C_1-C_6)$alkoxy, $(C_3-C_6)$cycloalkyl, oxo, carboxy, $R^g$, and $-NR^aR^b$;

each $R^a$ and $R^b$ is independently selected from H, $(C_1-C_6)$alkyl, $(C_3-C_6)$cycloalkyl, $(C_3-C_6)$cycloalkyl$(C_1-C_6)$alkyl, aryl, heteroaryl, aryl$(C_1-C_6)$ alkyl and heteroaryl$(C_1-C_6)$ alkyl; or $R^g$ and $R^h$ together with the nitrogen to which they are attached form a aziridino, azetidino, morpholino, piperazino, pyrrolidino or piperidino;

each $R^f$ is independently $(C_1-C_6)$alkyl, $(C_2-C_6)$alkenyl, $(C_2-C_6)$alkynyl, and $(C_3-C_6)$cycloalkyl; and each $R^g$ is independently aryl or heteroaryl, which aryl or heteroaryl is optionally substituted with one or more groups independently selected from halo, nitro, carboxy, cyano, $(C_1-C_6)$alkyl, $(C_2-C_6)$alkenyl, $(C_2-C_6)$alkynyl, $(C_3-C_6)$cycloalkyl, $(C_1-C_6)$alkanoyl, and $(C_1-C_6)$alkoxycarbonyl. This conversion can be carried out by treatment of the compound of formula 12c with phosphonium ylide of nitro, carboxy, cyano, $(C_1-C_6)$alkyl, $(C_2-C_6)$alkenyl, $(C_2-C_6)$alkynyl, $(C_3-C_6)$cycloalkyl, $(C_1-C_6)$alkanoyl, $(C_1-C_6)$alkoxycarbonyl, $-SO_2R^f$, and $(C_3-C_6)$cycloalkylcarbonyl at any suitable temperature (e.g. a temperature in the range of about $-80°$ C. to about room temperature. The conversion can also be carried out in the presence of a suitable solvent (e.g. THF, $Et_2O$, DME, methyl t-buty ether (MTBE), or toluene or a mixture thereof). For example see E. Carreira, *J. Med. Chem.*, 010, v53, p 3227; and Oxetanes as Promising Modules in Drug Discovery, ACIE, v45, p 7736.

In one embodiment the invention provides a method comprising reducing a compound of formula 3c:

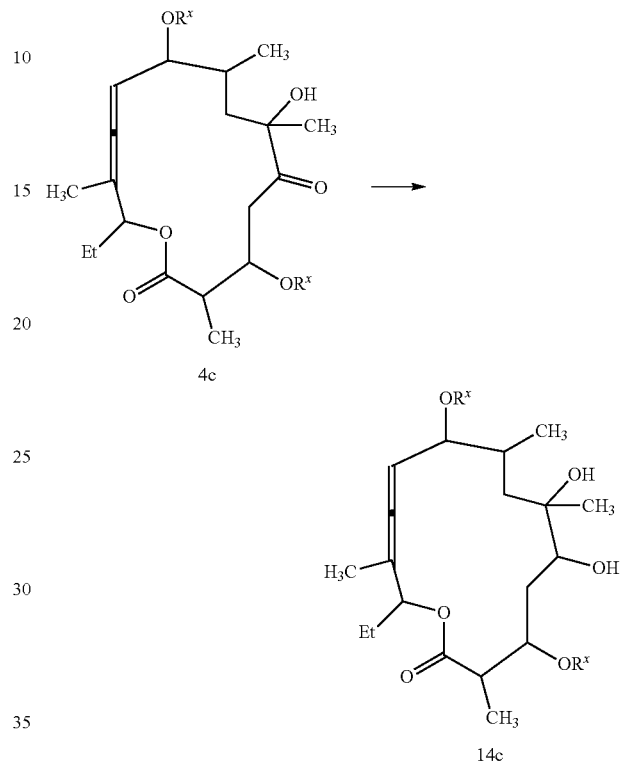

wherein each $R^x$ is independently a suitable protecting group to provide a compound of formula 14c. This reduction can be carried out by treatment of the compound of formula 4c with a suitable reducing agent (e.g. $NaBH_4$, or $Zn(BH_4)_2$, $NaBH(OiPr)_3$, or $Me_4NBH(OAc)_3$) at any suitable temperature (e.g. a temperature in the range of about $-80°$ C. to about room temperature. The conversion can also be carried out in the presence of a suitable solvent (e.g. an ether such as diethylether, tetrahydrofuran, ethanol, or dichloromethane or a mixture thereof). The reduction can be carried out using conditions similar to those described in Example 10 below.

In one embodiment the invention provides a method comprising converting a compound of formula 23c:

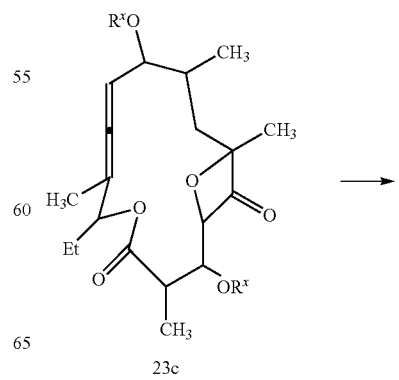

23c

-continued

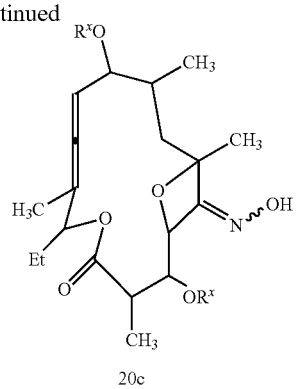
20c wherein each $R^x$ is independently a suitable protecting group to a compound of formula 20c. This conversion can be carried out by treatment of the compound of formula 23c with hydroxylamine-hydrochloride (1:1) in the presence of a suitable base (e.g. KOH, TEA, pyridine, or AcONa) at any suitable temperature (e.g. a temperature in the range of about −20° C. to about 50° C. The conversion can also be carried out in the presence of a suitable solvent (e.g. an alcohol such as ethanol, methanol, or water, or a mixture thereof). This conversion can conveniently be carried out by treating a compound of formula 23c with ammonium hydroxide in the presence of potassium hydroxide in ethanol at room temperature.

In one embodiment the invention provides a method for preparing a compound of formula 24c:

methylethyl dioxirane (MEDO), diethyl dioxirane (DEDO), methyl(trifluoromethyl)dioxirane (TFDO), oxone, tetraphenylphosphonium monoperoxysulfate (TPPP), Shi's fructose derived catalyst, Jacobsen's (salen) manganese (III) catalyst, isoquiniline-, biphenyl-, or binaphthyl-derived imminium salts, followed by treatment with MeLi or BuLi. The oxidation can be carried out at any suitable temperature (e.g. a temperature in the range of about −80° C. to about room temperature. Due to the stability of the resulting tetraepoxide, this epoxidation is typically carried out at a temperature in the range of from about −80° C. to about −30° C. The conversion can also be carried out in the presence of a suitable solvent (e.g. a halocarbon solvent such as chloroform, dichloromethane, carbon tetrachloride, trifluoroethanol, or hexane, acetone, t-butanol, water, acetonitrile, dimethylformamide (DMF), dimethylsulfoxide (DMSO), diethylketone (DEK), methyl ethyl ketone (MEK), 1,2-dimethoxyethane (DME), or 1,4-dioxane, or a mixture thereof). In one embodiment of the invention this conversion can be carried out by treating the compound of formula 116 with DMDO at −40° C. in chloroform to provide the corresponding tetraepoxide as illustrated in Example 8. The tetraepoxide can subsequently be treated with MeLi under any suitable conditions. The treatment with MeLi can be carried out at any suitable temperature (e.g. a temperature in the range of about −80° C. to about −20° C.). in the presence of a suitable solvent (e.g. a halocarbon solvent such as chloroform, dichloromethane, carbon tetrachloride, trifluoroethanol, or hexane, acetone, t-butanol, water, acetonitrile, dimethylformamide (DMF), dimethylsulfoxide (DMSO), diethylketone (DEK), methyl ethyl ketone (MEK), 1,2-dimethoxyethane (DME), or 1,4-dioxane or a mixture thereof). In one embodiment of the invention the MeLi treatment can be carried out as illustrated in Example 8.

In one embodiment the invention provides a method for preparing a compound of formula 25c:

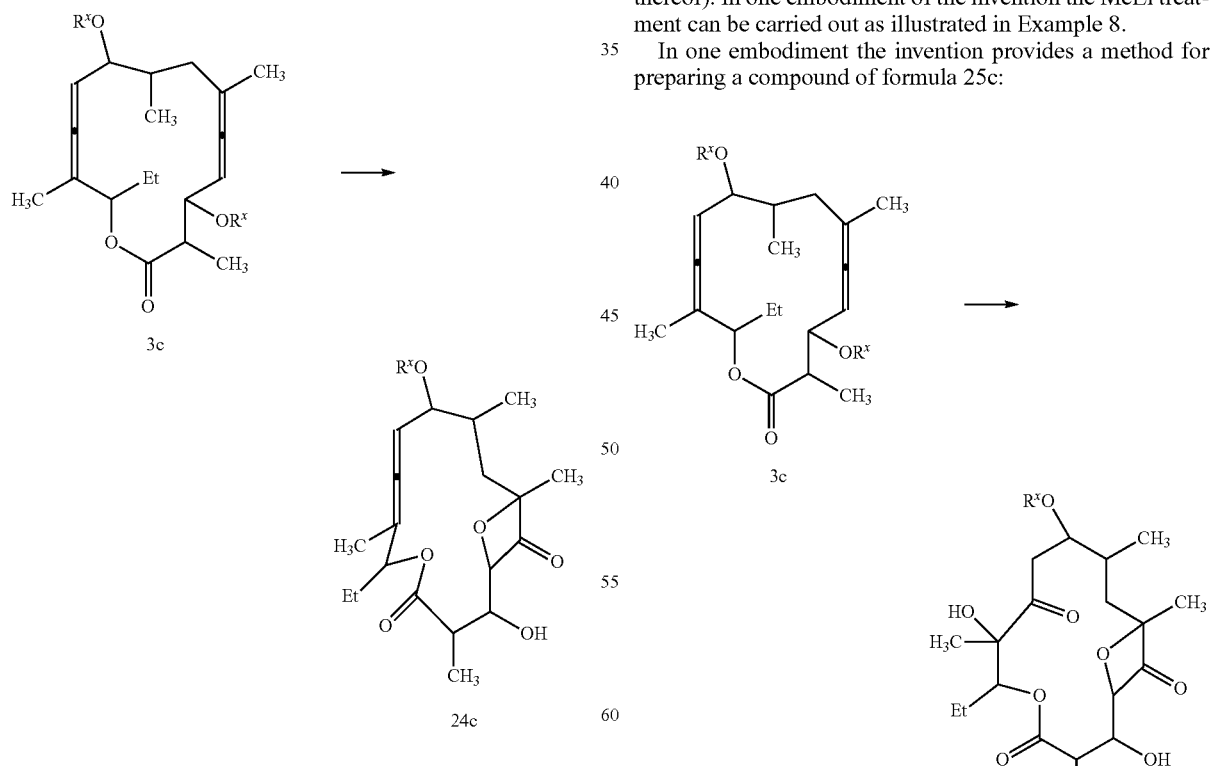

wherein each $R^x$ is independently a suitable protecting group comprising converting a compound of formula 3c to the compound of formula 24c. This conversion can be carried out by treatment of the compound of formula 3c with a suitable oxidizing agent (e.g. an epoxidizing agent such as DMDO, wherein each $R^x$ is independently a suitable protecting group comprising converting a compound of formula 3c to the compound of formula 25c. This conversion can conveniently be carried out using one of the methods described in Preparative Example 13. For example, this conversion can be carried out by treatment of the compound of formula 3c with a suitable oxidizing agent (e.g. an epoxidizing agent such as DMDO, methylethyl dioxirane (MEDO), diethyl dioxirane (DEDO), methyl(trifluoromethyl)dioxirane (TFDO), oxone, tetraphenylphosphonium monoperoxysulfate (TPPP), Shi's fructose derived catalyst, Jacobsen's (salen) manganese (III) catalyst, isoquiniline-, biphenyl-, or binaphthyl-derived imminium salts followed by treatment with a Lewis acid (e.g. a lithium salt, such as lithium perchlorate or lithium bromide, a copper salt, MeLi or BuLi). The oxidation can be carried out at any suitable temperature (e.g. a temperature in the range of about −80° C. to about 60° C. Due to the stability of the resulting tetraepoxide, this epoxidation is typically carried out at a temperature in the range of from about −80° C. to about −30° C. The conversion can also be carried out in the presence of a suitable solvent (e.g. a halocarbon solvent such as chloroform, dichloromethane, carbon tetrachloride, trifluoroethanol, or hexane, acetone, t-butanol, water, acetonitrile, dimethylformamide (DMF), dimethylsulfoxide (DMSO), diethylketone (DEK), methyl ethyl ketone (MEK), 1,2-dimethoxyethane (DME), or 1,4-dioxane or a mixture thereof). In one embodiment of the invention this conversion can be carried out by treating the compound of formula 3c with DMDO at −40° C. in chloroform to provide the corresponding tetraepoxide. The tetraepoxide can subsequently be treated with a suitable Lewis acid (e.g. MeLi) under any suitable conditions. The treatment with the Lewis acid (e.g. MeLi) can be carried out at any suitable temperature (e.g. a temperature in the range of about −80° C. to about −20° C.). In the presence of a suitable solvent (e.g. a halocarbon solvent such as chloroform, dichloromethane, carbon tetrachloride, trifluoroethanol, or hexane, acetone, t-butanol, water, acetonitrile, dimethylformamide (DMF), dimethylsulfoxide (DMSO), diethylketone (DEK), methyl ethyl ketone (MEK), 1,2-dimethoxyethane (DME), or 1,4-dioxane, or a mixture thereof).

In one embodiment the invention provides a method for preparing a compound of formula 26c:

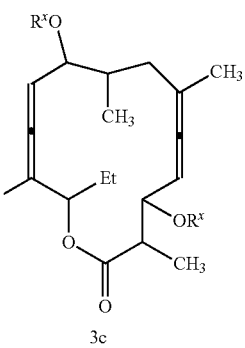

9c

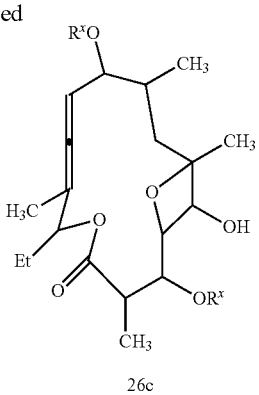

26c wherein each $R^x$ is independently a suitable protecting group comprising reducing a compound of formula 9c to provide the compound of formula 26c. This reduction can be carried out by treatment of the compound of formula 9c with a suitable reducing agent (e.g. $NaBH_4$, or $Zn(BH_4)_2$, $NaBH(OiPr)_3$, or $Me_4NBH(OAc)_3$) at any suitable temperature (e.g. a temperature in the range of about −80° C. to about 50° C.). The conversion can also be carried out in the presence of a suitable solvent (e.g. an ether such as diethylether, tetrahydrofuran, ethanol, or dichloromethane or a mixture thereof). The reduction can be carried out using conditions similar to those described in Example 10 below.

In one embodiment the invention provides a method for preparing a compound of formula 27c:

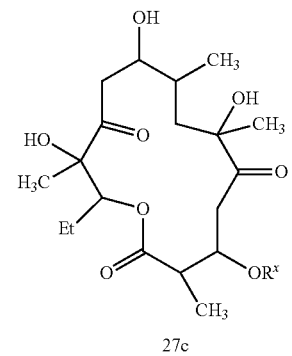

3c

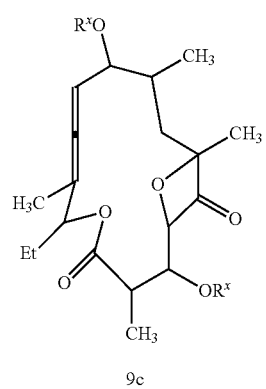

27c wherein each $R^x$ is independently a suitable protecting group comprising converting a compound of formula 3c to the compound of formula 27c. This conversion can be carried out by treatment of the compound of formula 3c with a suitable oxidizing agent (e.g. osmium tetroxide. The oxidation can be carried out at any suitable temperature (e.g. a temperature in the range of about −20° C. to about room temperature in the presence of a suitable solvent (e.g. a polar solvent such as tert-butanol, or water, or a mixture thereof). In one embodiment of the invention this conversion can be carried out by treating the compound of formula 3c with osmium tetroxide at room temperature in a mixture of tert-butanol and water as illustrated in Example 9.

In one embodiment the invention provides a method for preparing a compound of formula 28c:

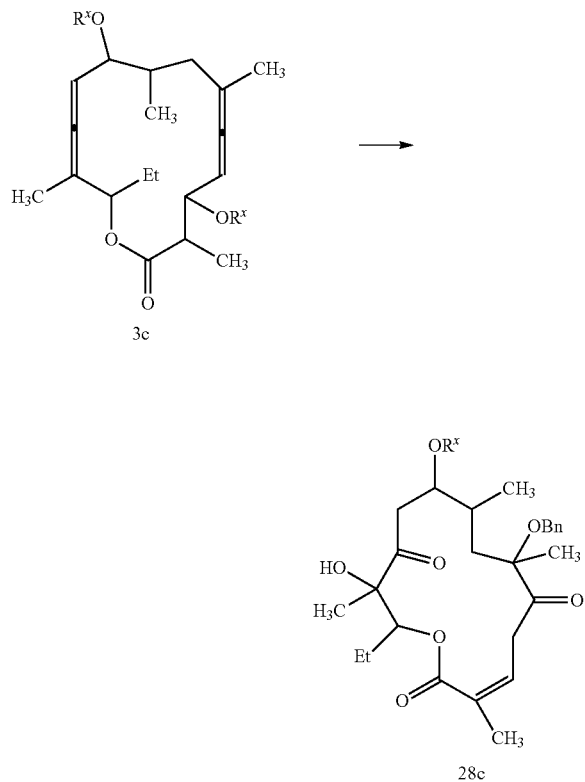

wherein each R$^x$ is independently a suitable protecting group comprising converting a compound of formula 3c to the compound of formula 28c. This conversion can be carried out by treatment of the compound of formula 3c with a suitable oxidizing agent (e.g. metachloroperbenzoic acid. The oxidation can be carried out at any suitable temperature (e.g. a temperature in the range of about −50° C. to about 20° C. in the presence of a suitable solvent (e.g. an ether such as chloroform, dichloromethane, carbon tetrachloride, trifluoroethanol, or hexane, acetone, t-butanol, water, acetonitrile, dimethylformamide (DMF), dimethylsulfoxide (DMSO), diethylketone (DEK), methyl ethyl ketone (MEK), 1,2-dimethoxyethane (DME), or 1,4-dioxane). In one embodiment of the invention this conversion can be carried out by treating the compound of formula 3c with Na$_2$HPO$_4$ and mCPBA sequentially at about −50° C.; increasing the temperature to about −10° C.; and adding methanol to provide the compound of formula 28c as illustrated in claim 5.

In one embodiment the invention provides a method for preparing a compound of formula 29c:

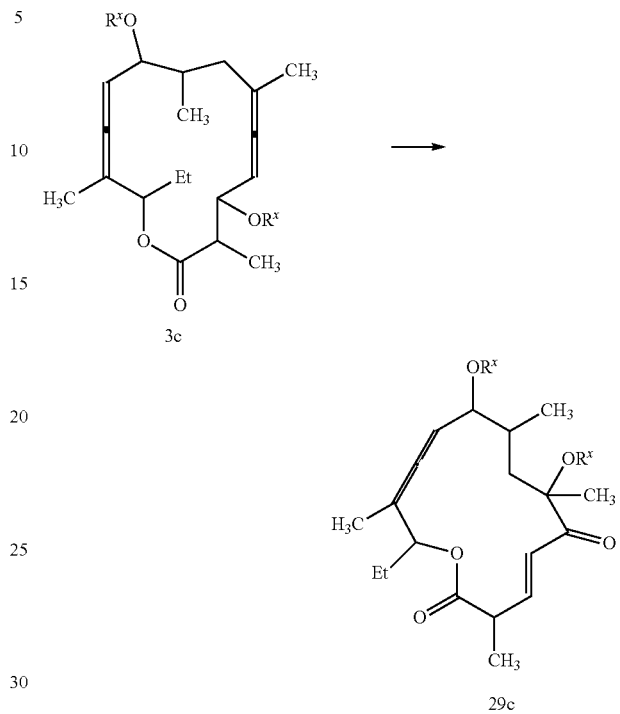

wherein each R$^x$ is independently a suitable protecting group comprising converting a compound of formula 3c to the compound of formula 29c. This conversion can be carried out by treatment of the compound of formula 3c with a suitable oxidizing agent (e.g. DMDO, methylethyl dioxirane (MEDO), diethyl dioxirane (DEDO), methyl(trifluoromethyl)dioxirane (TFDO), oxone, tetraphenylphosphonium Monoperoxysulfate (TPPP), Shi's fructose derived catalyst, Jacobsen's (salen) manganese (III) catalyst, isoquiniline-, biphenyl-, or binaphthyl-derived imminium salts. The oxidation can be carried out at any suitable temperature (e.g. a temperature in the range of about −80° C. to about 60° C. in the presence of a suitable solvent (e.g. an alcohol such as methanol, ethanol, or tert-butanol, or a mixture thereof. In one embodiment of the invention this conversion can be carried out by treating the compound of formula 3c with DMDO at about −50° C. in methanol as illustrated in Example 7.

In one embodiment the invention provides a method for preparing a compound of formula 119 or 120:

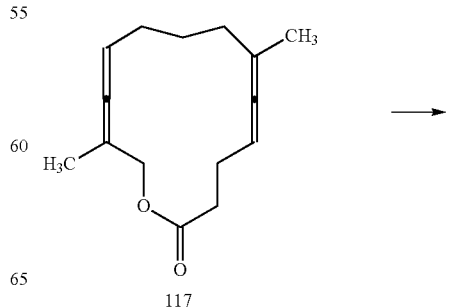

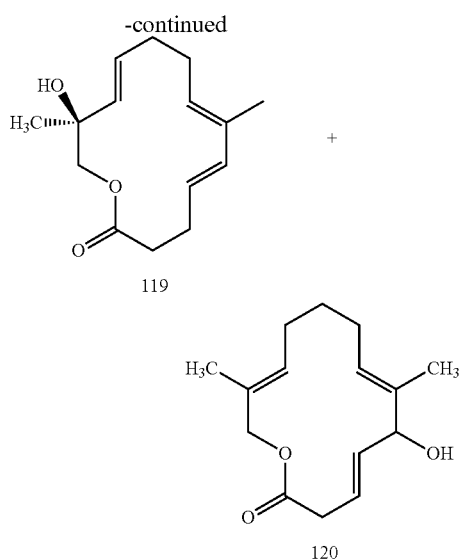

119

120 comprising converting a compound of formula 117 to the compound of formula 119 or formula 120. This conversion can be carried out by treatment of the compound of formula 117 with a suitable acid (e.g. mercuric sulfate). The conversion can be carried out at any suitable temperature (e.g. a temperature in the range of about 0° C. to about 100° C.) in the presence of a suitable solvent (e.g. an aqueous solvent such as tetrahydrofuran. In one embodiment of the invention this conversion can be carried out by treating the compound of formula 117 with sulfuric acid in water at about 70° C. to about 100° C. as illustrated in Example 2.

In one embodiment the invention provides a method for preparing a compound of formula 121:

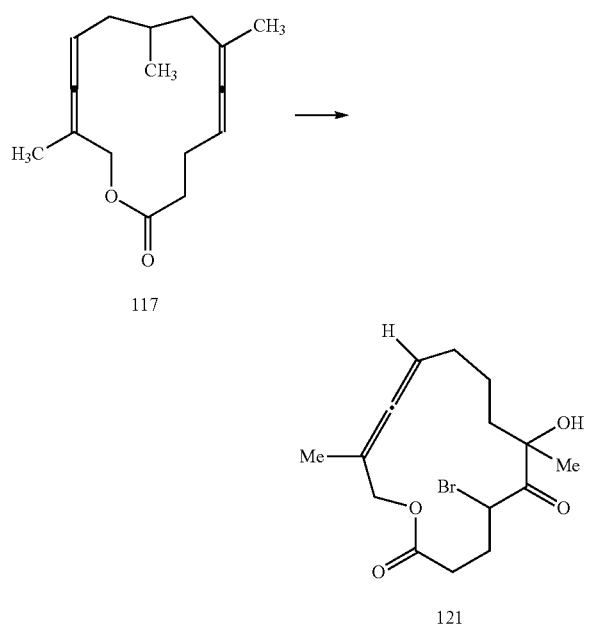

117

121 comprising converting a compound of formula 117 to the compound of formula 121. This conversion can be carried out by treatment of the compound of formula 117 with a suitable oxidizing agent (e.g. an epoxidizing agent such as DMDO, methylethyl dioxirane (MEDO), diethyl dioxirane (DEDO), methyl(trifluoromethyl)dioxirane (TFDO), oxone, tetraphenylphosphonium monoperoxysulfate (TPPP), Shi's fructose derived catalyst, Jacobsen's (salen) manganese (III) catalyst, isoquiniline-, biphenyl-, or binaphthyl-derived imminium salts, followed by treatment with LiBr or nBu$_4$NBr. The oxidation can be carried out at any suitable temperature (e.g. a temperature in the range of about −80° C. to about room temperature. The conversion can also be carried out in the presence of a suitable solvent (e.g. a halocarbon solvent such as chloroform, dichloromethane, carbon tetrachloride, trifluoroethanol, or hexane, acetone, t-butanol, water, acetonitrile, dimethylformamide (DMF), dimethylsulfoxide (DMSO), diethylketone (DEK), methyl ethyl ketone (MEK), 1,2-dimethoxyethane (DME), or 1,4-dioxane, or a mixture thereof). In one embodiment of the invention this conversion can be carried out by treating the compound of formula 117 with DMDO at about −40° C. in chloroform followed by warming to about −5° C. and treatment with LiBr to provide the compound of formula 121 as illustrated in Example 3.

In one embodiment the invention provides a method for preparing a compound of formula 31c:

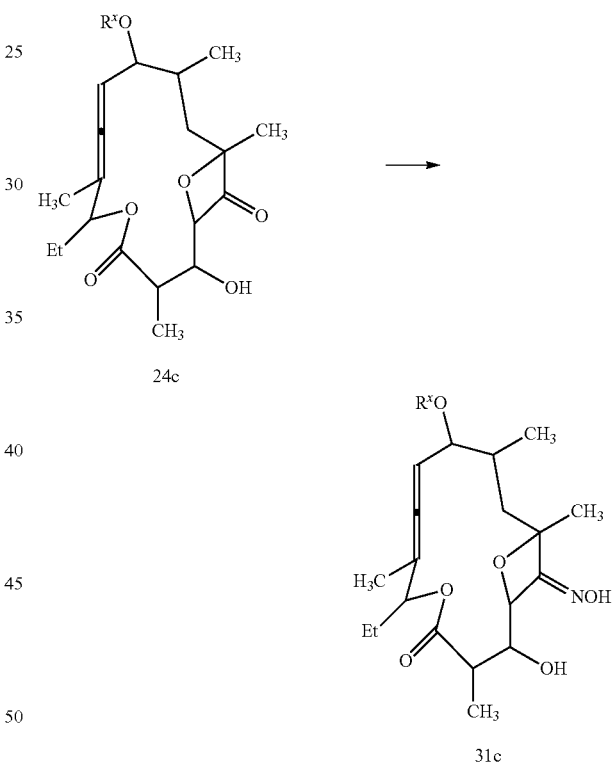

24c

31c wherein R$^x$ is a suitable protecting group comprising converting a compound of formula 24c to the compound of formula 31c. This conversion can be carried out by treatment of the compound of formula 24c with hydroxylamine-hydrochloride (1:1) in the presence of a suitable base (e.g. KOH, TEA, Pyridine, or AcONa) at any suitable temperature (e.g. a temperature in the range of about −20° C. to about 50° C. The conversion can also be carried out in the presence of a suitable solvent (e.g. an alcohol such as ethanol, methanol, or water, or a mixture thereof). This conversion can conveniently be carried out by treating a compound of formula 24c with ammonium hydroxide in the presence of potassium hydroxide in ethanol at room temperature as described in Example 11 below.

In one embodiment the invention provides a method for preparing a compound of formula 51 or formula 52:

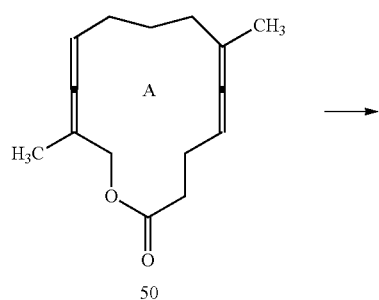

50

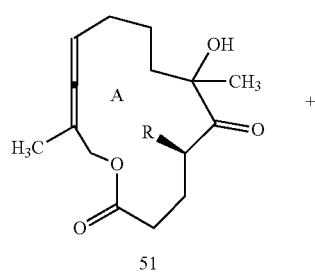

51

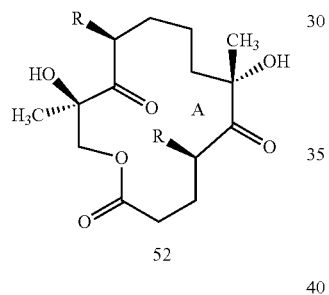

52 comprising treating a cyclic bis-allene of formula 50 with osmium tetroxide followed by an electrophilic cource of R to provide the corresponding compound of formula 51, or 52 wherein ring A is optionally substituted with one or more groups independently selected from halo, hydroxy, carboxy, cyano, $(C_1-C_6)$alkyl, $(C_2-C_6)$alkenyl, $(C_2-C_6)$alkynyl, $(C_1-C_6)$alkoxy, $(C_3-C_6)$cycloalkyl, aryl, aryl$(C_1-C_6)$alkyl, heteroaryl, heteroaryl$(C_1-C_6)$alkyl, aryl$(C_1-C_6)$alkanoyl, heteroaryl$(C_1-C_6)$alkanoyl, and $OR^c$; wherein each $(C_1-C_6)$ alkyl, $(C_2-C_6)$alkenyl, $(C_2-C_6)$alkynyl, $(C_1-C_6)$alkoxy, $(C_3-C_6)$cycloalkyl, and $(C_1-C_6)$alkanoyl is optionally substituted with one or more groups independently selected from halo, hydroxy, cyano, nitro, $(C_1-C_6)$alkyl, $(C_1-C_6)$alkoxy, $(C_3-C_6)$cycloalkyl, oxo, carboxy, aryl, heteroaryl, aryloxy, heteroaryloxy, and —$NR^aR^b$; and wherein each aryl, and heteroaryl is optionally substituted with one or more groups independently selected from halo, hydroxy, cyano, nitro, $(C_1-C_6)$alkyl, $(C_1-C_6)$alkoxy, $(C_3-C_6)$cycloalkyl, carboxy, aryl, heteroaryl, aryloxy, heteroaryloxy, and —$NR^aR^b$; and each $R^a$ and $R^b$ is independently selected from H, $(C_1-C_6)$ alkyl, $(C_3-C_6)$cycloalkyl, $(C_3-C_6)$cycloalkyl$(C_1-C_6)$alkyl, aryl, heteroaryl, aryl$(C_1-C_6)$ alkyl and heteroaryl$(C_1-C_6)$ alkyl; or $R^g$ and $R^h$ together with the nitrogen to which they are attached form a aziridino, azetidino, morpholino, piperazino, pyrrolidino or piperidino. This conversion can be carried out by treatment of the compound of formula 3c with osmium tetroxide at any suitable temperature (e.g. a temperature in the range of about −20° C. to about room temperature in the presence of a suitable solvent (e.g. a polar solvent such as tert-butanol, or water, or a mixture thereof). Any suitable source of electrophilic R can be used. For example, when R is chloro, N-chlorosuccinimide is a suitable source of R. In one embodiment of the invention the compound of formula 50 is a compound of formula 3c:

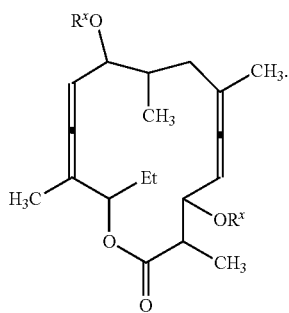

3c wherein each $R^x$ is independently a suitable protecting group. In another embodiment of the invention the compound of formula 50 is a compound of formula 3d:

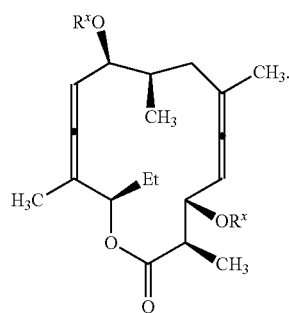

3d wherein each $R^x$ is independently a suitable protecting group.

In one embodiment the invention provides a compound of formula II

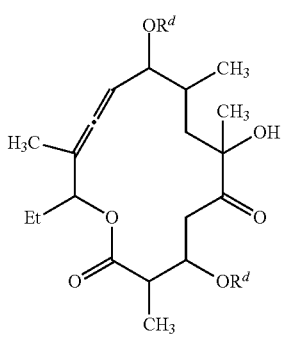

II wherein each $R^d$ is independently a H, saccharide, or a hydroxy protecting group; or a salt thereof.

In one embodiment the invention provides a compound of formula 8c:

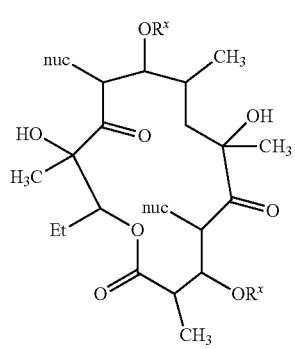

8c wherein each $R^x$ is independently a suitable protecting group wherein each nuc is independently selected from $(C_1-C_6)$ alkyl and halo (e.g. bromo).

In one embodiment the invention provides a compound of formula 8d:

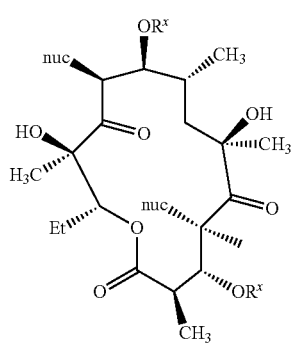

8d wherein each $R^x$ is independently a suitable protecting group.

In one embodiment the invention provides a compound of formula 23c:

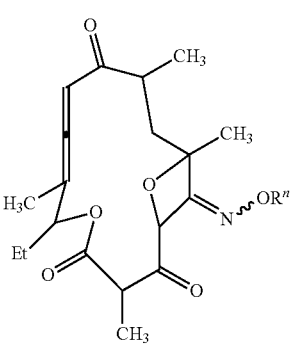

23c wherein $R^n$ is H, $(C_1-C_6)$alkyl, or a saccharide.

In one embodiment the invention provides a compound of formula:

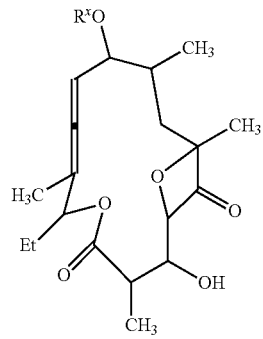

24c

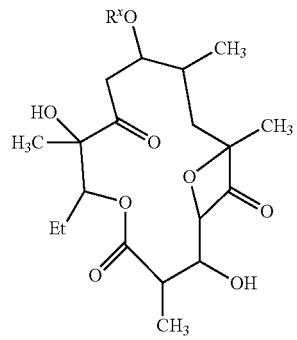

25c

26c

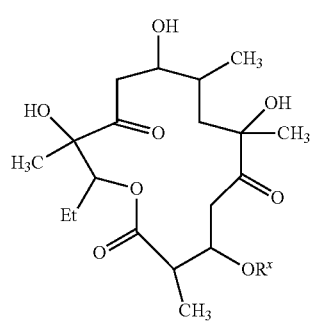

27c

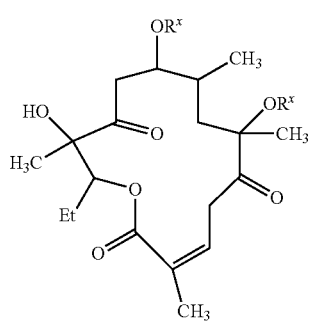
28c
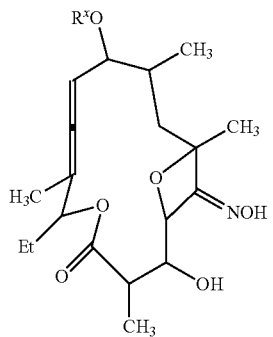
29c
or
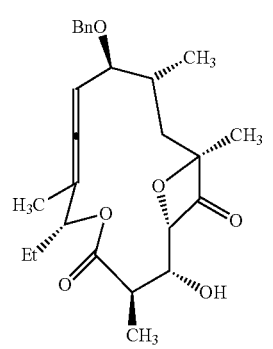
31c
wherein each $R^x$ is independently a suitable protecting group.
In one embodiment the invention provides a compound of formula:
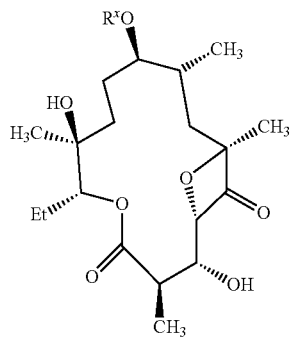
25d
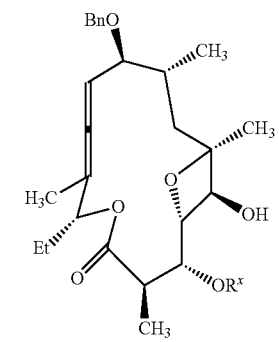
26d
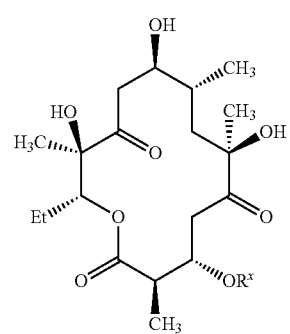
27d
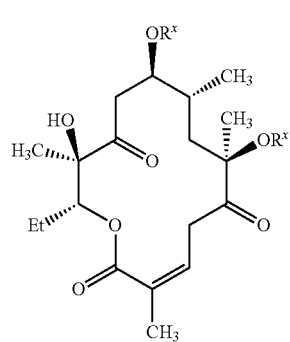
28d

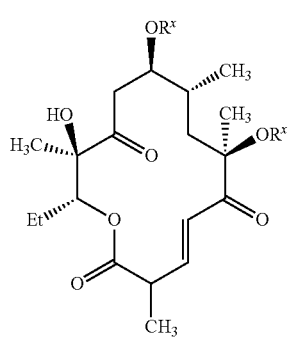
29d
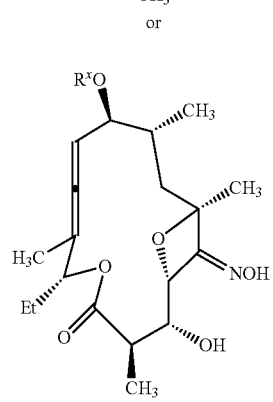
31d
wherein each $R^x$ is independently a suitable protecting group.
In one embodiment the invention provides a compound of formula 118, 119, 120, 121, 122, 123, 124, 125, 126, 127, 128, 129, 130, or 131:
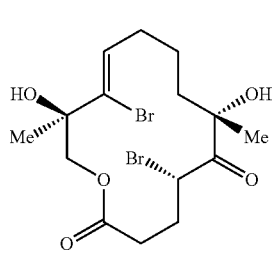
118
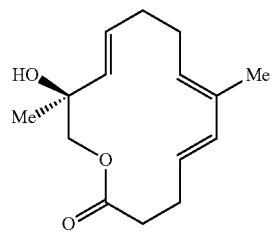
119
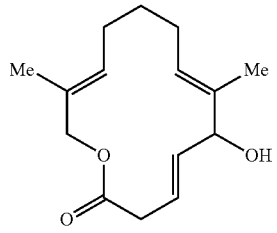
120
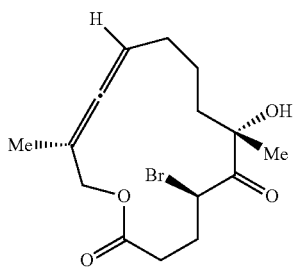
121
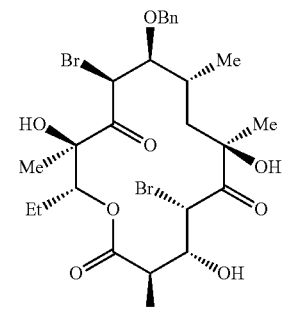
122
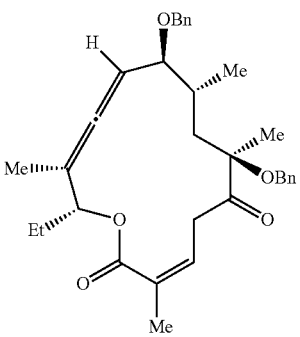
123
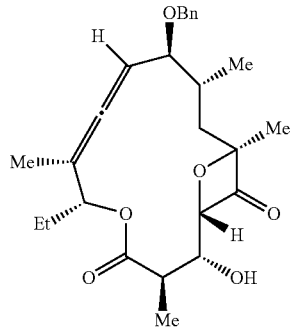
124
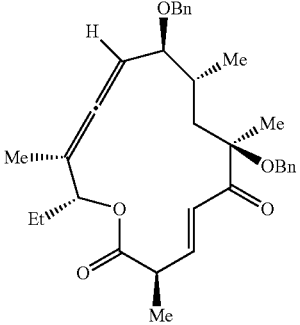
125

126

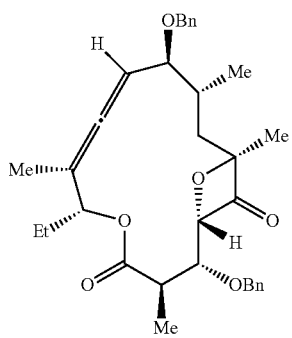

127

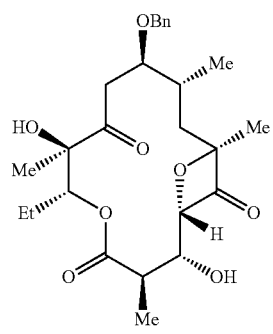

128

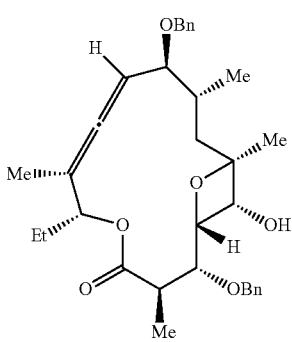

129

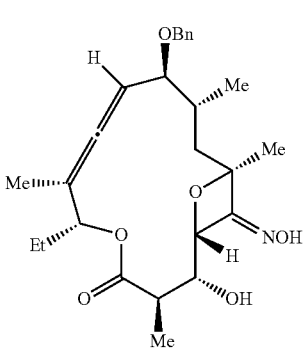

130

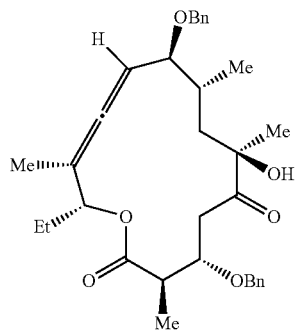

or

131

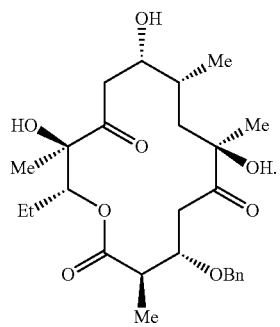

In one embodiment of the invention $R^x$ is a protecting group that comprises aryl, alkyl, or silyl functionality. In another embodiment $R^x$ is selected from benzyl, para-methoxybenzyl, 2,6-dimethoxybenzyl, methyl, 2,2,2-trifluoroethyl, tert-butyldimethylsilyl, tert-butyldiphenylsilyl, and triethylsilyl.

In one embodiment of the invention $R^x$ is benzyl.

In one embodiment the invention provides a compound of formula 214, 215, 216, 217, 218, 220, 221, or 222:

214

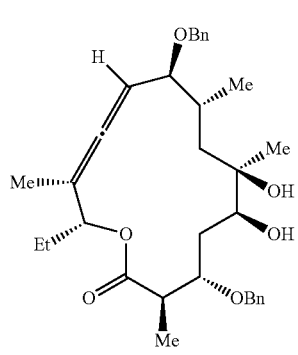

215
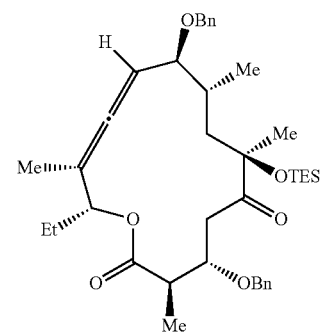
216
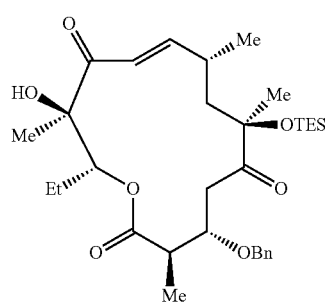
217
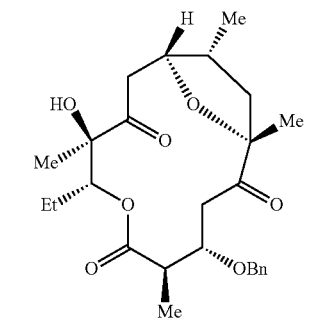
218
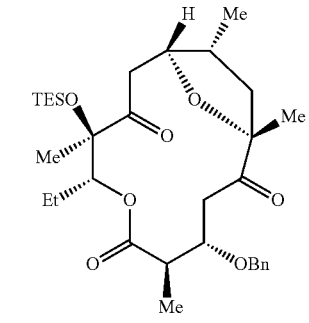
220
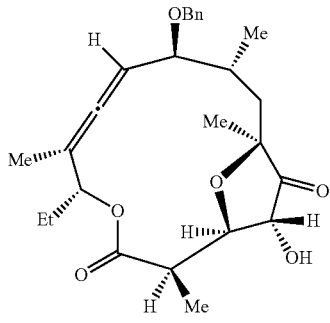
221
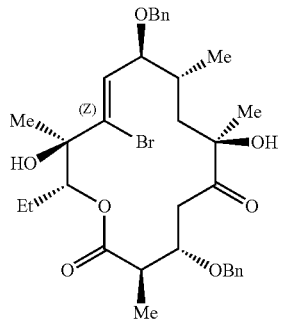
or
222
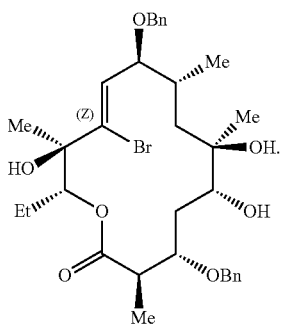
In one embodiment the invention provides a compound of formula 214, 215, 216, 217, 218, 220, 221, 222, 228-248, 250, 251, or 252:
214
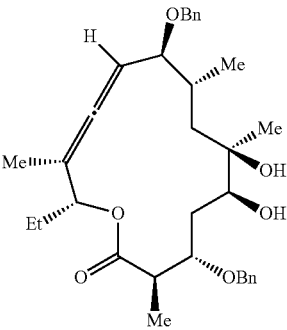
215
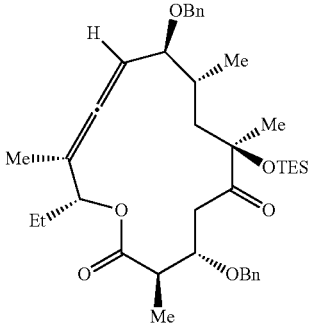

216
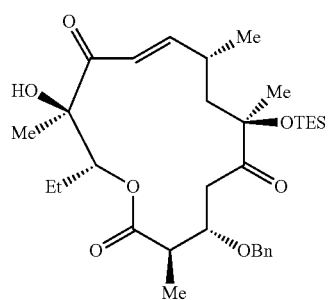
217
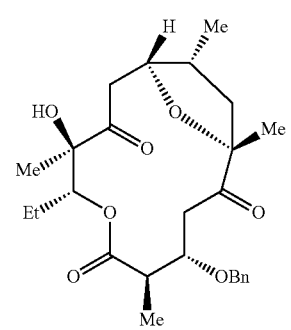
218
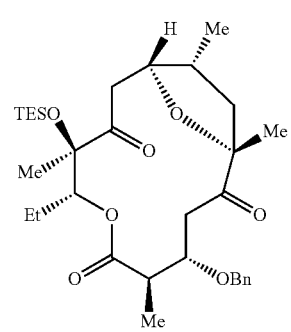
220
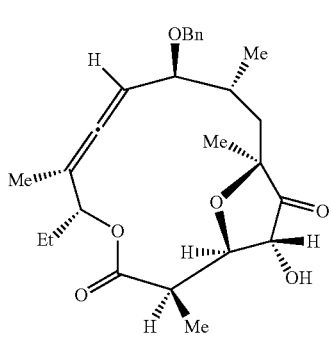
221
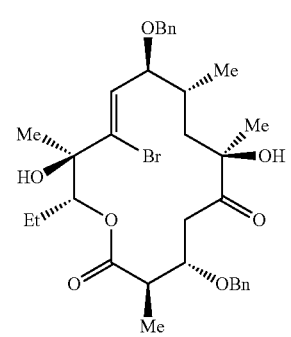
222
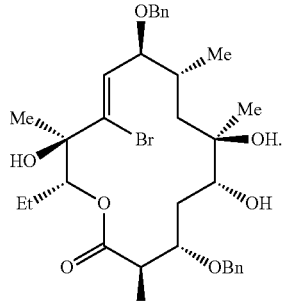
228
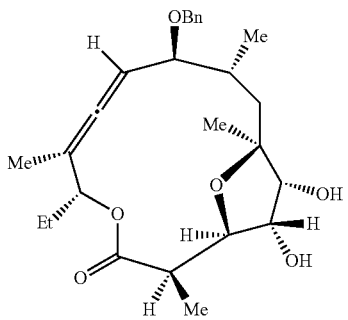
229
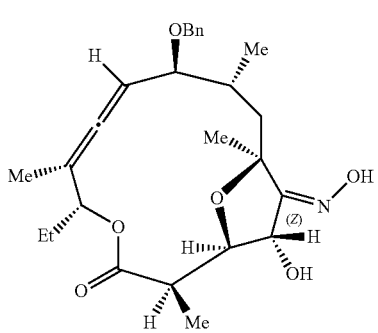
230
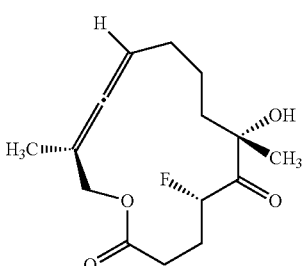
231
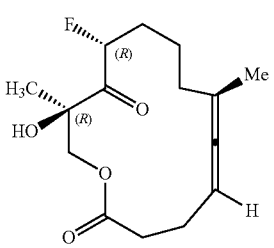

232
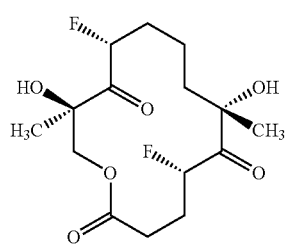
233
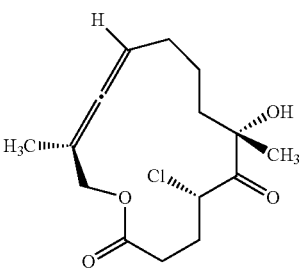
234
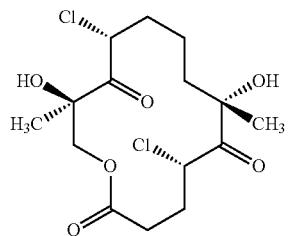
235
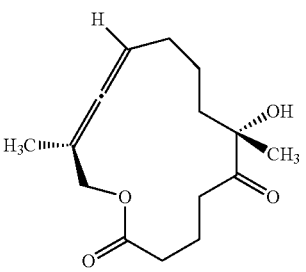
236
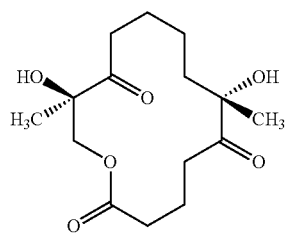
237
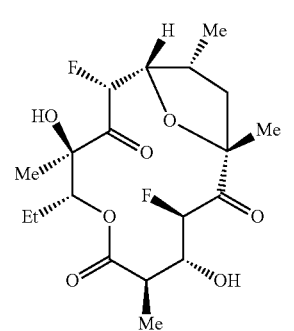
238
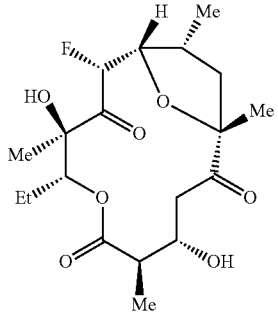
239
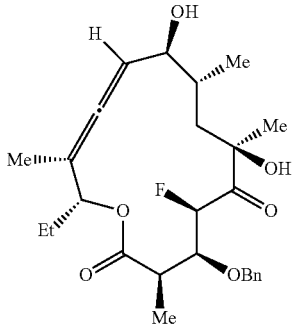
240
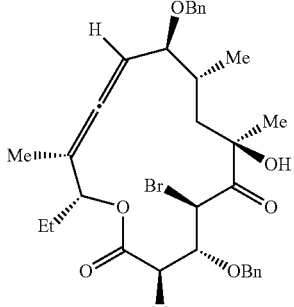
241
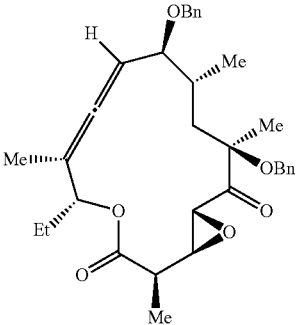
242
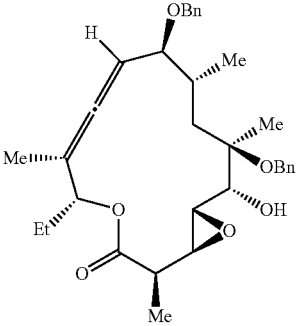

243
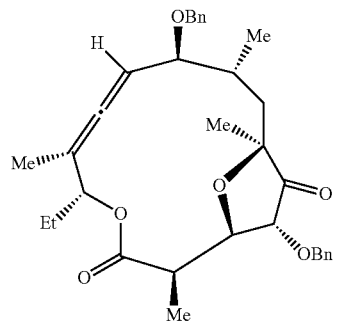
244
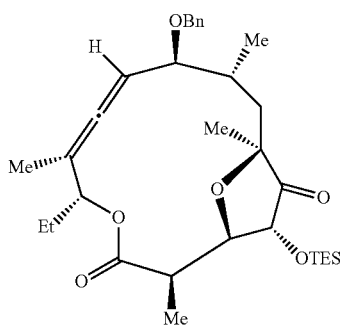
245
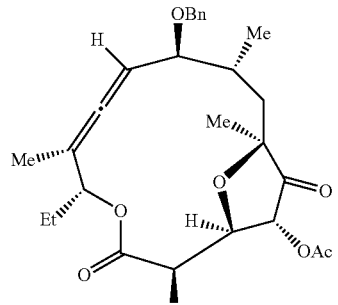
246
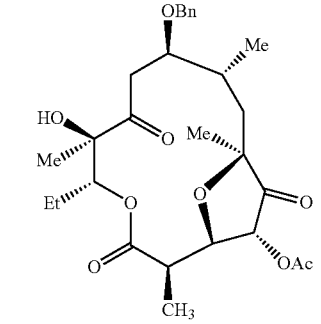
247
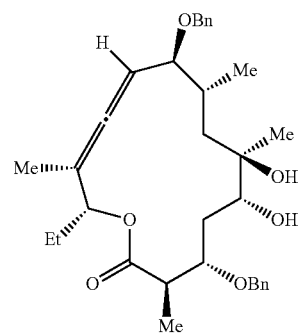
248
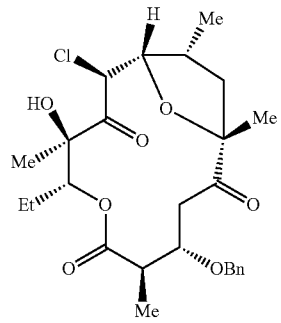
250
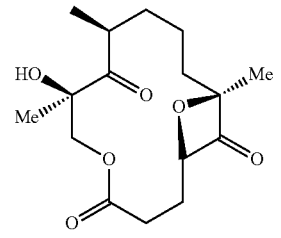
251
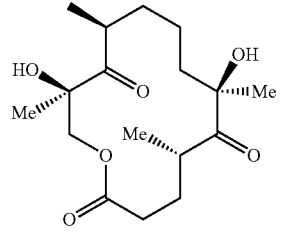
or
252
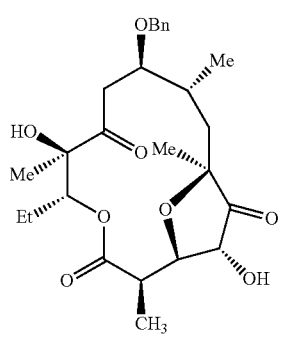
or a salt thereof.
In one embodiment the invention provides a compound of formula 220c:
220c
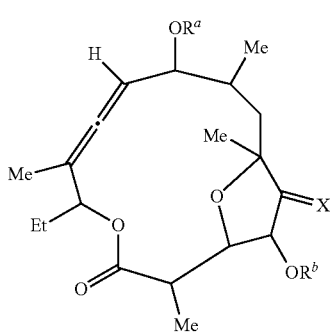

wherein:
R$^a$ is H, a saccharide, or a hydroxy protecting group;
R$^b$ is H, a saccharide, or a hydroxy protecting group;
X is O or N—OR$^c$; and
R$^c$ is H, a saccharide, or a hydroxy protecting group;
or a salt thereof.

In one embodiment the invention provides a compound of formula 220d:

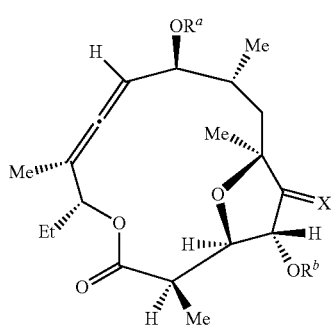

220d wherein:
R$^a$ is H, a saccharide, or a hydroxy protecting group;
R$^b$ is H, a saccharide, or a hydroxy protecting group;
X is O or N—R$^c$; and
R$^c$ is H, a saccharide, or a hydroxy protecting group;
or a salt thereof.

In one embodiment the invention provides a compound of formula 217c:

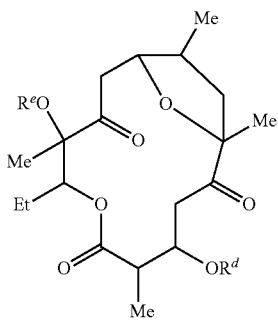

217c wherein:
R$^d$ is H, a saccharide, or a hydroxy protecting group; and
R$^e$ is H, a saccharide, or a hydroxy protecting group;
or a salt thereof.

In one embodiment the invention provides a compound of formula 217d:

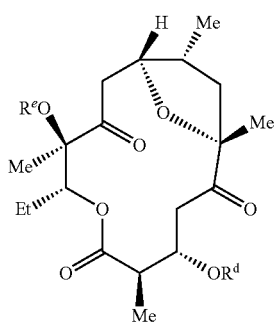

217d wherein:
R$^d$ is H, a saccharide, or a hydroxy protecting group; and
R$^e$ is H, a saccharide, or a hydroxy protecting group;
or a salt thereof.

In one embodiment the invention provides a method comprising converting compound of formula:

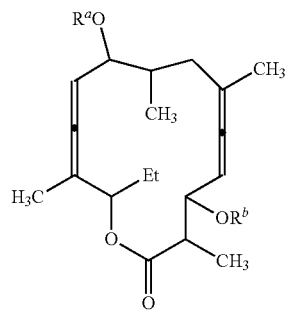

wherein R$^a$ is a hydroxy protecting group; and R$^b$ is a hydroxy protecting group;
to a corresponding compound of formula 220c:

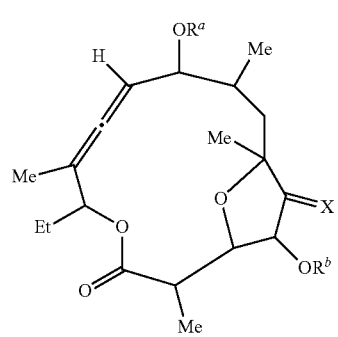

220c wherein X is O. For example, the conversion can be carried out by epoxidizing and treating the resulting epoxide with a methyl cuprate. In one embodiment the compound of formula 220c is a compound of formula 220d:

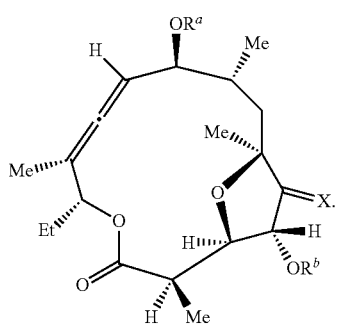

220d

In one embodiment the invention the compound of formula 220d wherein X is O is converted to a compound of formula 220d wherein X is N—OR$^c$; and R$^c$ is H, a saccharide, or a hydroxy protecting group.

In one embodiment the invention provides a method comprising, converting a compound of formula:

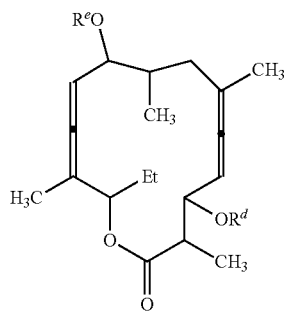

wherein $R^d$ is a hydroxy protecting group, and $R^e$ is a hydroxy protecting group;
to a corresponding compound of formula 217c:

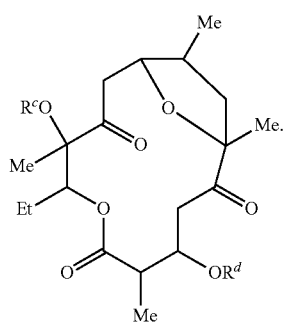

217c

In one embodiment the invention the compound is converted to the compound of formula 217c by treating with osmium tetroxide. In one embodiment the invention the compound of formula 217c is a compound of formula 217d:

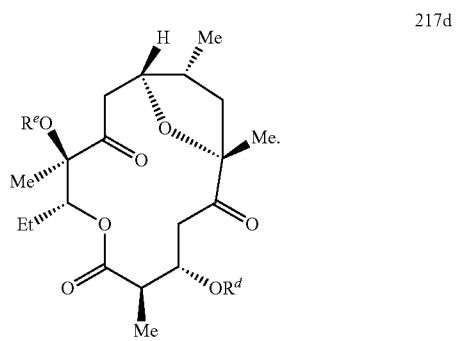

217d

Compound 116 can be converted to the biologically active natural product 9S-dihydroerythronolide A as illustrated below. 9S-Dihydroerythronolide A can subsequently be converted to erythronolide A and erythromycin as described by Kinoshita, M., et al., *Tetrahedron Lett.* 1986, 27, 1815; and Toshima, K., et al., *J. Am. Chem. Soc.* 1995, 117, 3717.

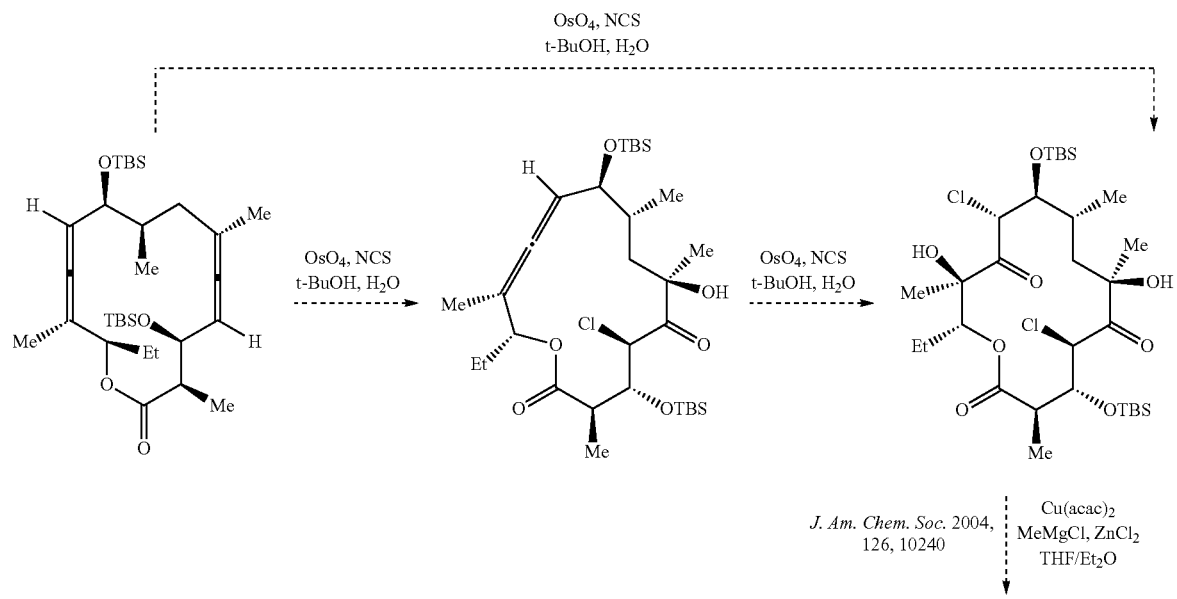

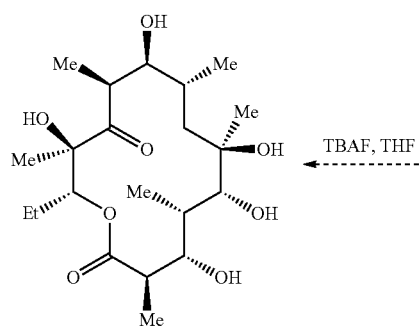

9S-dihydroerythronolide A

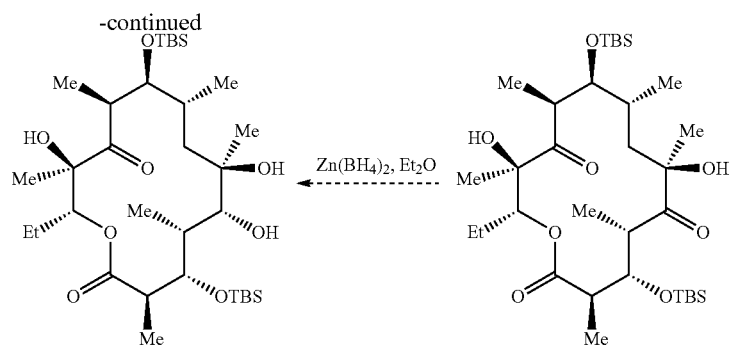

*Tetrahedron Lett.* 1986, 27, 1815

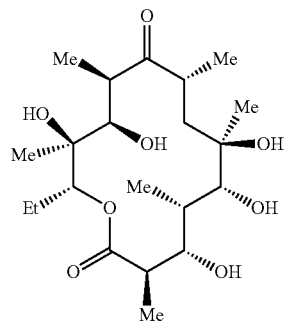

erythronolide A

*J. Am. Chem. Soc.* 1995, 117, 3717

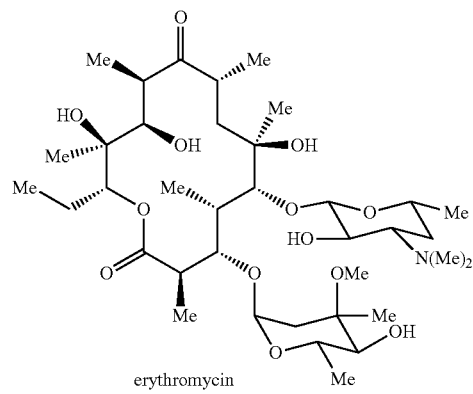

erythromycin

The antiinfective properties of a compound can be determined using pharmacological models which are well known to the art; for example, see Constantin Agouridas et al. *J. Med. Chem.* 1998, 41, 4080-4100; and Thomas V. Magee et al. *J. Med. Chem.* 2009, 52, 7446-7457.

The antitumor properties of a compound can be determined using pharmacological models such as a general MTT cytotoxicity assay with a standard panel of cancer cell lines (e.g. P388, MCF7, etc.), as well as pathway-specific assays using engineered cell lines, for example, the apoptosis-specific assay described by Andrianasolo, E. H., et al., *J. Nat. Prod.*, 2007, 70, 1551-1557.

The antiinflammatory properties of a compound can be determined using pharmacological models which are well known to the art; for example, see Constantin Agouridas et al. *J. Med. Chem.* 1998, 41, 4080-4100; and Thomas V. Magee et al. *J. Med. Chem.* 2009, 52, 7446-7457.

The invention will now be illustrated by the following non-limiting Examples.

EXAMPLES

General Experimental

All commercial available starting materials, reagents and solvents were purchased from suppliers (Aldrich, Acros, Strem, TCI America and Ochem, etc.) and used without further purification. Anhydrous solvent such as tetrahydrofurn (THF), diethyl ether, dichloromethane (DCM), toluene were purchased from Sigma-Aldrich then passed over a solvent purification system containing alumina based columns and dried by activated 4 Å molecular sieves for 1 hour before use. Anhydrous THF was further distilled from calcium hydride before use. All the glassware used for reaction were flame-dried under vacuum. All the reactions were conducted under the atmosphere of high purity argon gas. The progress of all reactions were monitored by silica gel thin layer chromatography (TLC, mesh size 60 Å with fluorescent indicator, Dynamic Absorbents Inc.), visualized under UV and/or stained using different stains (such as anisaldehyde, vanillin, cerium ammonium molybdate, $KMnO_4$. Crude products were purified by flash column chromatography (FCC) on 120-400 mesh silica gel if necessary. Proton nuclear magnetic resonance spectra ($^1H$ NMR) were obtained from either a Varian-300 instrument (300 MHz), Varian-400 instrument (400 MHz), Varian-500 instrument (500 MHz) or Inova-600 instrument (600 MHz). Chemical shifts are reported in ppm with tetramethylsilane (TMS) being the internal standard. Data is reported as follows: chemical shift (multiplicity (s=singlet, d=doublet, t=triplet, q=quartet, br=broad, m=multiplet), coupling constants (Hz) and integration). Carbon nuclear magnetic resonance spectra ($^{13}$C NMR) were obtained from either a Varian-400 instrument (100 MHz), Varian-500 instrument (125 MHz) or Inova-600 instrument (150 MHz). Chemical shifts are reported in ppm with tetramethylsilane (TMS) being the internal standard. Optical rotations were recorded at 25° C. using the sodium D line (589 nm). Mass spectra were recorded on a Finnigan LCQ-DUO mass spectrometer or Finnigan high resolution mass spectrometer. Infrared (FTIR) spectra were recorded on ATI Mattson Genesis Series FT-Infrared spectrophotometer.

EXAMPLES

Example 1

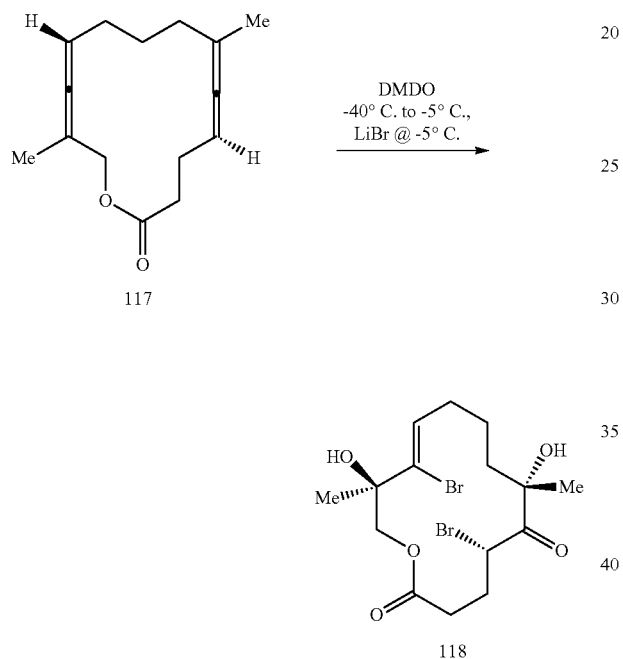

To a solution of bis[allene]macrolactone 117 (47 mg, 0.202 mmol) in CDCl$_3$ (1 ml) was added a solution of dimethyldioxirane (DMDO) in CDCl$_3$ (2.023 ml, 0.607 mmol) dropwise at −40° C. The reaction was stirred under nitrogen and let to warm to −5° C. over 1 h 30 min. To the reaction mixture was added LiBr (3 eq, 52.8 mg, 0.607 mmol) at −5° C. TLC showed the unreacted SDE. To the reaction mixture was added LiBr (7 eq, 123.2 mg, 1.416 mmol). After the complete consumption of SDE, the reaction was then quenched with aqueous NH$_4$Cl and extracted with DCM. The combined organic phase was dried over anhydrous Na$_2$SO$_4$. Evaporation of solvent and FCC purification using 20% EtOAc in hexanes gave 118 as colorless oil (50 mg, 55.6% yield). $^1$H NMR (600 MHz, CDCl$_3$) δ 6.04 (dd, J=9.0, 6.6 Hz, 1H), 5.05 (d, $^2$J=13.3 Hz, 1H), 4.64 (dd, J=9.1, 5.7 Hz, 1H), 4.18 (d, $^2$J=13.3 Hz, 1H), 2.70 (dddd, J=17.6, 9.5, 2.5 Hz, 1H), 2.41 (m, 1H), 2.37 (m, 1H), 2.35 (m, 1H), 2.31 (m, 1H), 2.175-2.210 (m, 1H), 2.03 (s, 3H), 1.925-1.850 (m, 1H), 1.675 (m, 1H), 1.625 (m, 1H), 1.57 (s, 3H), 0.975-0.900 (m, 1H); $^{13}$C NMR (150 MHz, CDCl$_3$) δ 208.0548, 169.8770, 132.0986, 131.7404, 78.8850, 69.7074, 64.5327, 42.0690, 36.5558, 31.3084, 30.5838, 28.6575, 28.5799, 26.9656, 22.0335; m/z (HRMS) found: 422.980587, 424.97849, 426.97648 (M−H$_2$O)$^+$. calc'd: 439.98.

Example 2

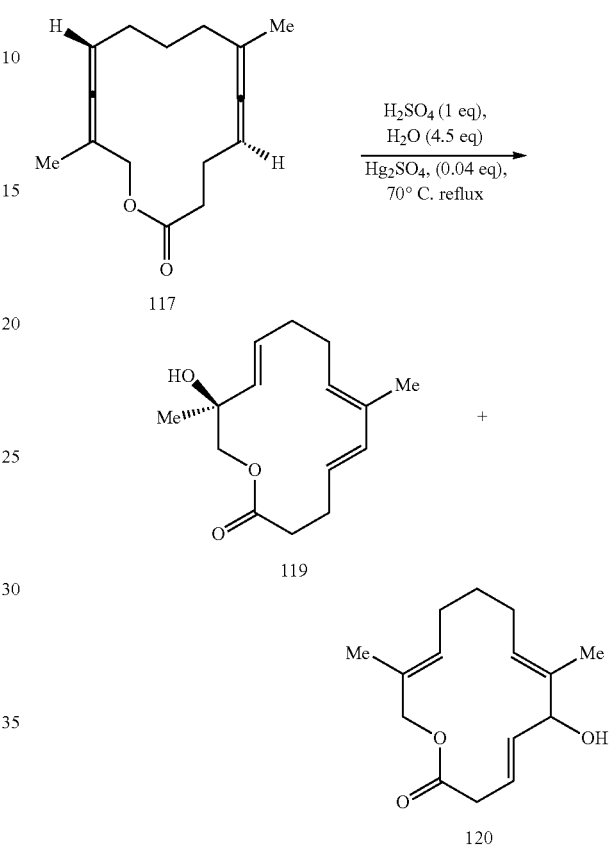

To a solution of bis[allene]macrolactone 117 (36.6 mg, 0.158 mmol) in THF (2 ml) was added sulfuric acid (15.45 mg, 0.158 mmol), water (12.85 mg, 0.714 mmol), mercuric sulfate (1.870 mg, 6.30 µmol) sequentially. The reaction mixture was heated under reflux at 70° C. for 5 hrs. After the complete consumption of bis[allene]macrolactone, the reaction was cooled down to rt and diluted with water. The organic phase was extracted with EtOAc and dried over anhydrous Na$_2$SO$_4$. Evaporation of solvent and flash column chromatography purification using 20% EtOAc in hexanes gave a mixture of 119 (15.9 mg, 40.3%) and 120 (14.4 mg, 36.5%) as colorless oil.

Compound 119: $^1$H NMR (600 MHz, CDCl$_3$) δ 6.39 (d, J=15.9 Hz, 1H), 5.78-5.67 (m, 1H), 5.65-5.54 (m, 1H), 5.48 (d, J=15.7 Hz, 1H), 5.34 (t, J=8.07 Hz, 1H), 4.13 (dd, J=42.4, 11.2 Hz, 2H), 2.64-2.58 (m, 2H), 2.55-2.44 (m, 2H), 2.32-2.18 (m, 2H), 2.15-2.07 (m, 2H), 1.81 (s, 3H), 1.22 (s, 3H; $^{13}$C NMR (150 MHz, CDCl$_3$) δ 173.4518, 134.0190, 133.2787, 129.3698, 127.6153, 127.4709, 126.9800, 72.2176, 70.7591, 32.3294, 31.7668, 27.6211, 26.9622, 25.5889, 20.3401; m/z (HRMS) found: 273.14535 (M+Na)$^+$. calc'd: 273.14612.

Compound 120: $^1$H NMR (600 MHz, CDCl$_3$) δ 5.37 (s, 1H), 5.24 (t, J=8.07 Hz, 1H), 5.22-5.16 (m, 1H), 4.79 (s, 1H), 4.52 (m, 2H), 2.60-2.51 (m, 2H), 2.40-2.32 (m, 2H), 2.07-2.05 (m, 1H), 1.99-1.87 (m, 1H), 1.76-1.74 (m, 2H), 1.73 (s, 3H), 1.53-1.46 (m, 2H), 1.26 (s, 3H); $^{13}$C NMR (150 MHz, CDCl$_3$) δ 177.45, 136.44, 128.34, 123.80, 123.57, 122.80, 86.76, 77.98, 77.82, 39.67, 36.03, 29.59, 23.40, 16.95, 12.52.

Example 3

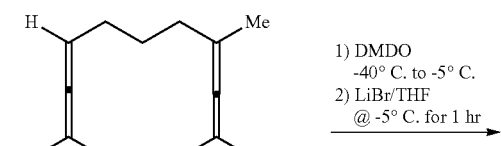

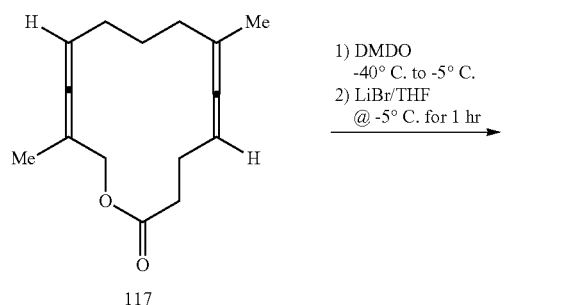

To a solution of bis[allene]macrolactone 117 (26.6 mg, 0.114 mmol) in CHCl$_3$ (1 ml) was added a solution of DMDO in CDCl$_3$ (1.145 ml, 0.343 mmol) dropwise at −40° C. The reaction was stirred under nitrogen and let to warm to −5° C. over 1 hr 30 min. After the consumption of 117, excess DMDO was removed under reduced pressure and the crude mixture was azeotroped with toluene. To the crude mixture was added a solution of LiBr (39.8 mg, 0.458 mmol) in THF (1 ml) via syringe pump for 1 hr at −5° C. After the consumption of SDE, the reaction mixture was quenched with aqueous NH$_4$Cl and extracted with DCM. The combined organic phase was dried over anhydrous Na$_2$SO$_4$. Evaporation of solvent and flash column chromatography purification using 15% EtOAc in hexanes gave 121 (24.2 mg, 61.2%) of as white solid. The product was recrystallized in 20% EtOAc in hexane. $^1$H NMR (300 MHz, CDCl$_3$) δ 5.27-5.17 (m, 1H), 4.94 (dd, J=12.4, 2.9 Hz, 1H), 4.70 (t, J=7.0 Hz, 1H), 4.11 (dd, J=12.5, 1.8 Hz, 1H), 3.72 (s, 1H), 2.69-2.54 (m, 1H), 2.52-2.30 (m, 3H), 2.06-1.97 (m, 2H), 1.73 (d, J=2.93 Hz, 3H), 1.59-1.57 (m, 2H), 1.55 (s, 3H), 1.39-1.24 (m, 1H), 0.96-0.80 (m, 1H); $^{13}$C NMR (101 MHz, CDCl$_3$) δ 208.96, 203.23, 171.72, 95.87, 92.01, 79.18, 65.87, 41.79, 37.91, 31.80, 29.79, 28.43, 26.85, 22.79, 17.61; m/z (HRMS) found: 369.05189, 369.04988 (M+Na)$^+$. calc'd: 368.229.

Example 4

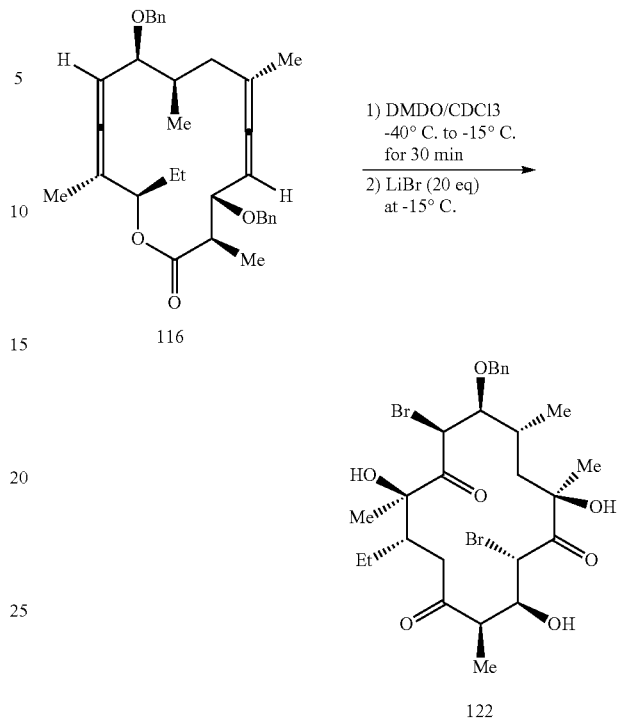

To a solution of bis[allene]macrolactone 116 (15 mg, 0.030 mmol) in CDCl$_3$ (1 ml) was added a solution of DMDO in CDCl$_3$ (0.399 ml, 0.180 mmol) dropwise at −40° C. The reaction was stirred under nitrogen and let to warm to −15° C. over 30 min. To the reaction mixture was added LiBr (53.2 mg, 0.599 mmol) at −15° C. After the complete consumption of SDE, the reaction was diluted with water and extracted with DCM. The combined organic phase was dried over anhydrous Na$_2$SO$_4$. Evaporation of solvent and flash column chromatography purification using 15% EtOAc in hexanes gave 122 as colorless oil (2 mg, 10.5% yield). $^1$H NMR (600 MHz, CDCl$_3$) δ 7.42-7.33 (m, 10H), 6.00 (d, J=8.51 Hz, 1H), 5.17 (dd, J=2.64, 10.56 Hz, 2H), 4.55 (d, J=7.92 Hz, 1H), 3.86 (d, J=9.39 Hz, 1H), 3.83 (dd, J=3.82, 9.69 Hz, 1H), 3.17 (t, J=6.45 Hz, 1H), 1.50 (s, 3H), 1.36 (d, J=7.34 Hz, 3H), 1.21 (s, 3H), 1.05 (d, J=6.75 Hz, 3H), 0.99-0.91 (m, 3H).

Example 5

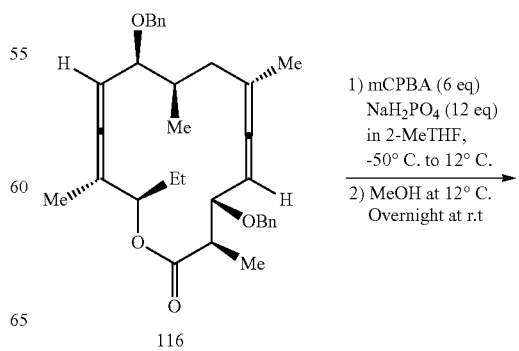

-continued

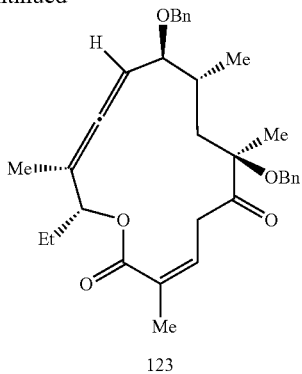

123

To a solution of bis[allene]macrolactone 116 (15 mg, 0.030 mmol) in 2-methyl THF (3 ml) was added Na$_2$HPO$_4$ (51 mg, 0.360 mmol) and mCPBA (31 mg, 0.180 mmol) sequentially at −50° C. The temperature was slowly increased to 11.6° C. over 5 hr 30 min. To the reaction mixture was methanol (4 ml) and stirred overnight. The reaction was quenched with aqueous NaHCO$_3$ and extracted with EtOAc. The combined organic phase was dried over anhydrous Na$_2$SO$_4$. Evaporation of solvent and flash column chromatography purification using 15% EtOAc in hexanes gave 123 as colorless oil (7 mg, 45.2% yield).

$^1$H NMR (600 MHz, CDCl$_3$) δ 7.43-7.29 (m, 10H), 7.10 (t, J=9.98, 1H), 5.36-5.29 (m, 1H), 5.08-4.98 (m, 1H), 4.62 (d, J=11.44 Hz, 1H), 4.39-4.18 (m, 3H), 3.78-3.67 (m, 2H), 3.30-3.18 (m, 2H), 1.91 (s, 3H), 1.87-1.79 (m, 3), 1.77 (d, J=2.94 Hz, 3H), 1.66-1.61 (m, 1H), 1.28 (s, 3H), 1.02 (d, J=6.75, 3H), 0.88 (t, J=7.04 Hz, 3H); m/z (ESIMS) found: 539.1 (M+Na)$^+$. calc'd: 539.6.

Example 6

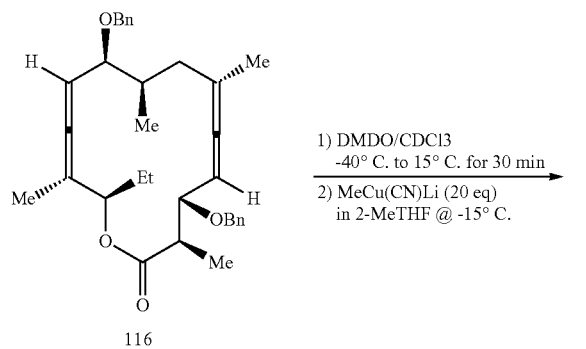

116

1) DMDO/CDCl3
   −40° C. to 15° C. for 30 min
2) MeCu(CN)Li (20 eq)
   in 2-MeTHF @ −15° C.

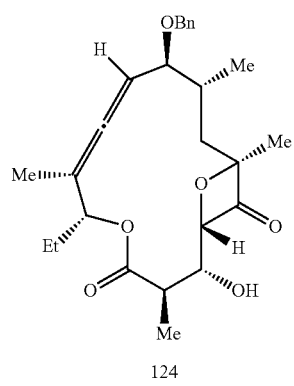

124

To a solution of bis[allene]macrolactone 116 (17.7 mg, 0.035 mmol) in CDCl$_3$ (0.5 ml) was added a solution of DMDO (0.558 ml, 0.212 mmol) dropwise at −40° C. The temperature was increased to −15° C. over 30 min. Lower order methyl cyanocuprate was prepared by addition MeLi (0.442 ml, 0.707 mmol) to a slurry of CuCN (63.3 mg, 0.707 mmol) in 2-methyl THF (5.99 ml) at −78° C. and then warming to −14.6° C. To a solution of methyl cyanocuprate was added a solution of SDE slowly. The reaction was warmed to −1.8° C. over 1 hr 30 min. The reaction was then quenched with a solution of NH$_4$OH and NH$_4$Cl (1:4 ratio) and extracted with diethyl ether. The combined organic phase was dried over anhydrous Na$_2$SO$_4$. Evaporation of solvent and flash column chromatography purification using 15% EtOAc in hexanes gave 124 (10 mg, 63.9% yield) as colorless oil. $^1$H NMR (600 MHz, CDCl$_3$) δ 7.44-7.31 (m, 5H), 5.60 (dd, J=8.1, 6.3 Hz, 1H), 5.39-5.06 (m, 2H), 4.63 (d, J=12.1 Hz, 1H), 4.40 (d, J=12.1 Hz, 1H), 3.92 (dd, J=8.7, 4.4 Hz, 1H), 3.85 (dd, J=8.0, 2.6 Hz, 1H), 3.06 (dd, J=7.4, 4.4 Hz, 1H), 2.56 (d, J=2.9 Hz, 1H), 1.87 (dd, J=14.9, 5.8 Hz, 1H), 1.80 (d, J=2.64 Hz, 3H), 1.70 (m, 1H), 1.65 (dd, J=8.9, 5.0 Hz, 2H), 1.35 (d, J=7.63 Hz, 3H), 1.14 (s, 3H), 0.93 (t, J=7.63 Hz, 3H), 0.88 (d, J=7.04 Hz, 3H); $^{13}$C NMR (150 MHz, CDCl$_3$) δ 218.94, 206.57, 171.03, 138.57, 128.51, 128.06, 127.71, 99.02, 90.72, 83.35, 82.28, 79.71, 76.66, 76.62, 75.92, 72.53, 70.23, 40.46, 40.20, 34.02, 24.28, 22.83, 14.47, 13.78, 13.58, 10.00.

Example 7

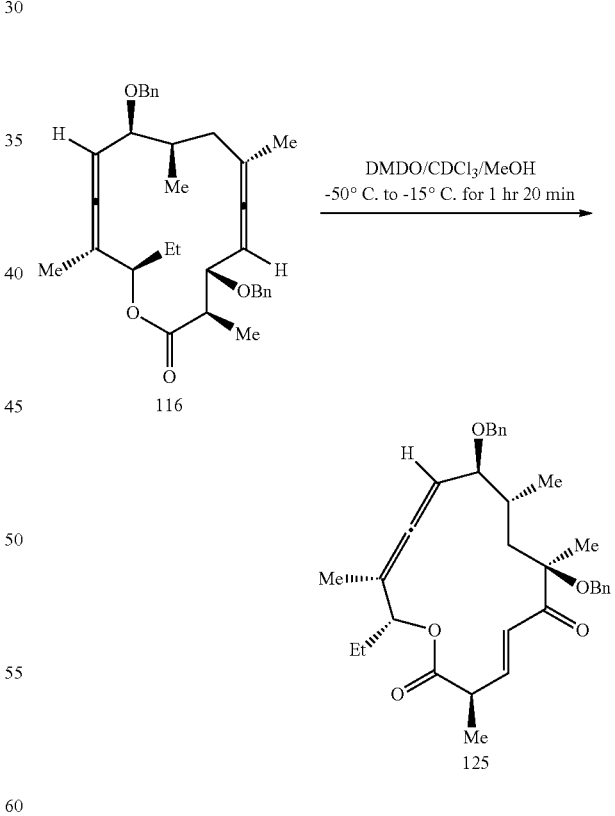

To a solution of bis[allene]macrolactone 116 (12 mg, 0.024 mmol) in methanol (3 ml) was added a solution of DMDO (0.378 ml, 0.38 ml) dropwise at −50° C. The reaction was stirred under nitrogen and let to warm to −15° C. over 1 hr 42 min. Evaporation of solvent and flash column chromatography purification using 5% EtOAc in hexanes gave 125 (10 mg, 81%) of as colorless oil. $^1$H NMR (600 MHz, CDCl$_3$) δ

7.36-7.27 (m, 10H), 7.05 (d, J=15.65 Hz, 1H), 6.73 (dd, J=8.31, 15.89 Hz, 1H), 4.71 (t, J=10.02 Hz, 1H), 4.64-4.60 (m, 1H), 4.57 (d, J=11.01 Hz, 1H), 4.56 (d, J=11.98 Hz, 1H), 4.26 (d, J=11.49 Hz, 1H), 4.24 (d, J=11.74 Hz, 1H), 3.30 (dt, J=14.67, 6.84 Hz, 1H), 3.24 (t, J=9.78 Hz, 1H), 1.95 (d, J=14.18 Hz, 1H), 1.82 (d, J=2.94 Hz, 3H), 1.78-1.68 (m, 2H), 1.48 (d, J=14.43 Hz, 1H), 1.44 (s, 3H), 1.42-1.41 (m, 1H), 1.32 (d, J=6.84 Hz, 3H), 1.09 (d, J=6.60 Hz, 3H), 0.99 (t, J=7.34 Hz, 3H); $^{13}$C NMR (150 MHz, CDCl$_3$) δ 202.5921, 202.0975, 171.8700, 145.2928, 138.5663, 138.4472, 128.4243, 128.3196, 128.2871, 128.2221, 127.7708, 127.7239, 127.5289, 127.3953, 127.3628, 127.1787, 127.0306, 101.1286, 93.9328, 84.8703, 82.9676, 75.8476, 69.7638, 66.3121, 42.2948, 41.4174, 33.5428, 26.4336, 19.9672, 18.0102, 17.3748, 14.5766, 9.6735; MS (ESI+) calculated for [C$_{33}$H$_{40}$O$_5$+Na]$^+$: 539.3. found: 539.3. [α]$^{25}_D$=3.3° (c=0.005, CHCl$_3$).

Example 8

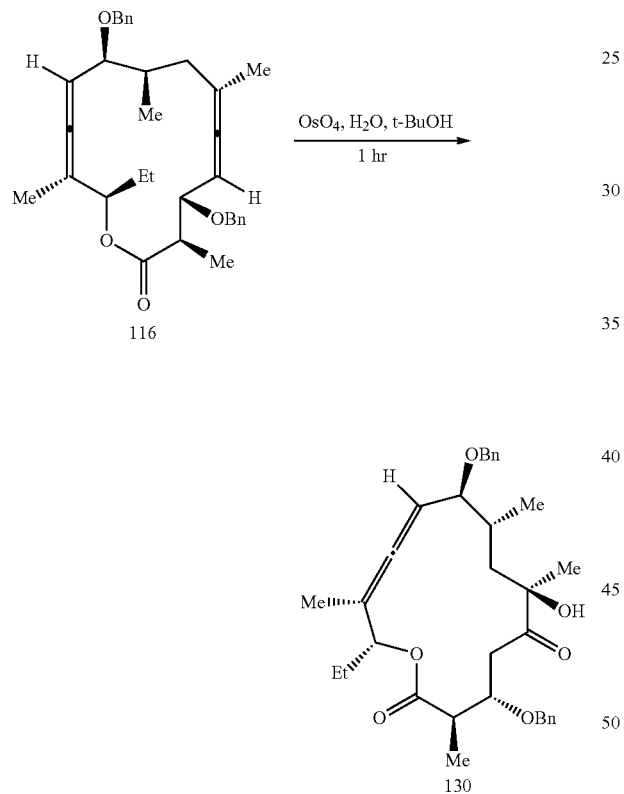

The macrolactone 116 (26 mg, 0.052 mmol) was dissolved in the mixture of t-BuOH and water (2 ml, 1:1 ratio). To the solution was added OsO$_4$ 4% wt. water solution (495 ml, 0.078 mmol) at rt then stirred for 45 mins then quenched by 20 ml saturated sodium sulfite solution, extracted with diethyl ether (2×20 ml). Organic layer was concentrated to dryness under reduced pressure. Flash column chromatography using 10% ethyl acetate in hexane gives the macrolactone 130 as a light yellowish oil (23 mg, 0.043 mmol, 83% yield): IR ν$_{max}$ (neat)/cm$^{-1}$ 13475, 2930, 2872, 1966, 1739, 1496, 1455, 1370; $^1$H NMR (500 MHz, CDCl$_3$) δ 7.26-7.38 (m, 10H), 5.15 (m, 1H), 4.94 (m, 1H), 4.74 (d, J=11.6 Hz, 1H), 4.60 (d, J=12.2 Hz, 1H), 4.56 (d, J=11.6 Hz, 1H), 4.34 (d, J=12.2 Hz, 1H), 4.15 (m, 1H), 3.44 (dd, J=6.8, 8.1 Hz, 1H), 2.96 (dd, J=6.9, 17.7 Hz, 1H), 2.93 (dd, J=3.8, 17.7 Hz, 1H), 2.58 (m, 1H), 1.9 (dd, J=6.6, 15.1 Hz, 1H), 1.79 (d, J=2.9 Hz, 1H), 1.73 (m, 1H), 1.69 (m, 2H), 1.54 (dd, J=3.2, 15.1 Hz, 1H), 1.32 (s, 3H), 1.30 (d, J=6.8 Hz, 3H), 1.05 (d, J=6.8 Hz, 3H), 0.90 (t, J=7.4 Hz, 3H). $^{13}$C NMR (126 MHz, CDCl$_3$) δ 212.1, 204.0, 173.8, 138.6, 138.4, 128.6, 128.5, 128.1, 127.9, 127.7, 126.1, 99.8, 96.7, 82.3, 78.9, 76.5, 76.0, 73.8, 70.0, 45.6, 43.0, 42.6, 34.2, 27.4, 25.3, 18.6, 15.5, 13.7, 9.6; MS (ESI+) calculated for [C$_{33}$H$_{42}$O$_6$+Na]$^+$: 557.3. found: 557.3.

Example 9

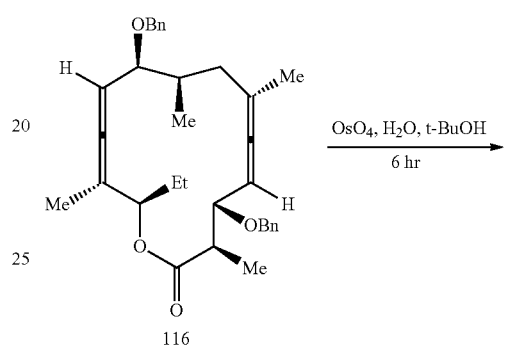

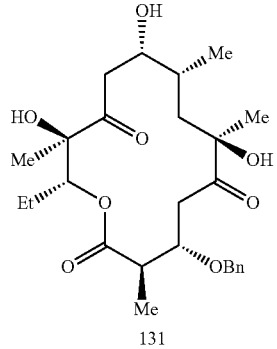

The macrolactone 116 (10 mg, 0.02 mmol) was dissolved in a 1:1 mixture solution of t-BuOH and water (1 ml), to that was added 0.28 ml OsO$_4$ solution (4% wt. in water) at room temperature. Stirred for 4 hours then quenched with 15 ml saturated sodium sulfite solution for 15 mins then extracted with diethyl ether (2×20 ml). The organic layer was combined and dried over Na$_2$SO$_4$ then concentrated to dryness under reduced pressure. Flash column chromatography using 20% ethyl acetate and hexane gives macrolactone 131 as a colorless oil. (4 mg, 0.0084 mmol, 41.8% yield). $^1$H NMR (500 MHz, CDCl$_3$) δ 7.44-7.28 (m, 2H), 4.89 (dd, J=9.0, 3.4 Hz, 1H), 4.64 (dd, J=10.3, 7.0 Hz, 1H), 4.58 (s, 1H), 3.86 (dd, J=11.7, 6.8 Hz, 1H), 3.48 (dd, J=14.0, 7.0 Hz, 1H), 3.38 (dd, J=14.4, 7.2 Hz, 1H), 3.09 (dd, J=18.7, 10.6 Hz, 1H), 2.98-2.82 (m, 1H), 2.51-2.36 (m, 1H), 2.31 (d, J=3.8 Hz, 1H), 1.98 (ddd, J=14.5, 7.5, 3.5 Hz, 1H), 1.91 (dd, J=12.8, 8.9 Hz, 1H), 1.80 (dd, J=12.9, 7.4 Hz, 1H), 1.65-1.49 (m, 5H), 1.41 (d, J=22.4 Hz, 6H), 1.28 (t, J=12.3 Hz, 4H), 1.21 (dd, J=7.1, 4.4 Hz, 2H), 0.94 (dd, J=15.1, 7.6 Hz, 1H), 0.91-0.71 (m, 4H), 0.68 (d, J=7.0 Hz, 1H).

Example 10

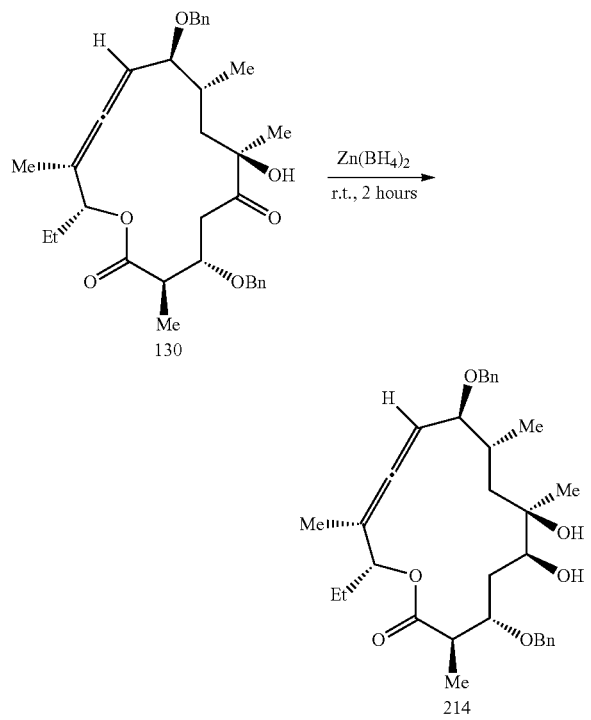

The macrolactone 130 (26 mg, 0.049 mmol) was dissolved in 2 ml diethyl ether, then cooled to 0° C. To that was added 0.2 M zinc borohydride solution in diethyl ether (0.25 ml, 0.05 mmol). Stirred for 80 mins, slowly warmed up to rt then quenched with saturated NH$_4$Cl solution. Additional ether (5 ml) was added then the water layer was removed by pipette. Organic layer concentrated to dryness under reduced pressure. Flash column chromatography using 25% ethyl acetate in hexane gives the macrolactone 214 (23.1 mg, 87% yield). $^1$H NMR (400 MHz, CDCl$_3$) δ 7.45-7.27 (m, 8H), 7.21 (d, J=6.9 Hz, 2H), 5.38 (s, 1H), 5.26-5.15 (m, 1H), 4.74 (d, J=12.3 Hz, 1H), 4.71-4.61 (m, 1H), 4.59 (s, 1H), 4.42 (d, J=12.3 Hz, 1H), 4.18 (d, J=3.4 Hz, 2H), 3.99-3.86 (m, 1H), 3.74-3.65 (m, 1H), 3.65-3.54 (m, 1H), 3.34-3.23 (m, 1H), 3.02-2.92 (m, 1H), 2.90 (s, 1H), 2.83-2.67 (m, 2H), 2.13-1.93 (m, 2H), 1.84 (d, J=4.3 Hz, 1H), 1.74 (d, J=2.9 Hz, 2H), 1.72-1.66 (m, 1H), 1.33-1.18 (m, 3H), 1.16 (s, 1H), 1.10-1.02 (m, 2H), 1.00 (d, J=6.8 Hz, 3H), 0.90 (dd, J=14.2, 6.8 Hz, 3H).

Example 11

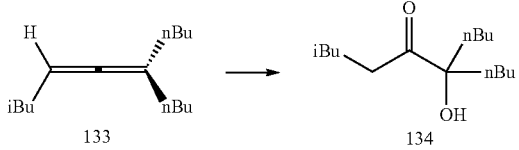

This Example provides three different osmium tetroxide catalyzed dihydroxylation procedures that can be used in the methods of the invention.

Procedure A:

The allene 133 (100 mg, 0.48 mmol) was dissolved in 1:1 mixture of water and t-BuOH (1 ml). To this solution was added osmium tetraoxide 4% wt. solution in water (0.153 ml, 0.024 mmol), N-methylmorpholine N-oxide (67.5 mg, 0.576 mmol) and acetic acid (86 mg, 1.440 mmol) at rt. Stirred for 12 hours then quenched with saturated sodium sulfite solution, diluted with 20 ml diethyl ether, washed with water (2×10 ml). Organic layer dried over Na$_2$SO$_4$ then concentrated under reduced pressure. Flash column chromatography using 5% ethyl acetate in hexane gives the known compound 134 as colorless oil (82 mg, 71% yield). IR vmax (neat)/cm-1 3481.7, 1703.9, 1467.5; δH (400 MHz, CDCl$_3$) 3.903 (1H, s), 2.442 (2H, t, J=7.6 Hz), 1.76-1.65 (4H, m), 1.60-1.46 (4H, m), 1.44-1.23 (7H, m), 0.912 (6H, d, J=6.4 Hz), 0.873 (6H, t, J=7.2 Hz); δc (100 MHz, CDCl$_3$) 214.8, 81.6, 38.7, 33.8, 32.3, 27.6, 25.4, 22.9, 22.3, 13.9; m/z (ESIMS) 243.0 (M+H)+.

Procedure B:

The allene 133 (100 mg, 0.48 mmol) was dissolved in 2.5 ml DCM. To this solution was added the phenylboronic acid (70.2 mg, 0.576 mmol), N-methylmorpholine N-oxide (67.5 mg, 0.576 mmol) and acetic acid (115 mg, 1.920 mmol) at rt. Stirred for 6 hours then quenched with saturated sodium sulfite solution, diluted with 20 ml diethyl ether, washed with water (2×10 ml). Organic layer dried over Na$_2$SO$_4$ then concentrated under reduced pressure. Flash column chromatography using 5% ethyl acetate in hexane gives the known compound 134 as a colorless oil (82 mg, 71% yield). Spectrum result was the same as procedure A.

Procedure C:

The allene 133 (100 mg, 0.48 mmol) was dissolved in 1:1 mixture of water and t-BuOH (8 ml). To this solution was added potassium ferricyanide (474 mg, 1.440 mmol), potassium carbonate (199 mg, 1.440 mmol), DABCO (13.46 mg, 0.120 mmol) and OsO$_4$ 4% wt. solution in water (305 mg, 0.048 mmol). Stirred for 24 hours then quenched with saturated sodium sulfite solution, diluted with 20 ml diethyl ether, washed with water (2×10 ml). Organic layer dried over Na$_2$SO$_4$ then concentrated under reduced pressure. Flash column chromatography using 5% ethyl acetate in hexane gives the known compound 134 as colorless oil (75 mg, 64.5% yield). Spectrum characterization result was the same as procedure A and B.

Example 12

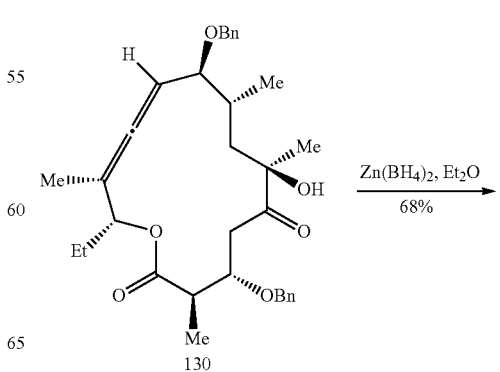

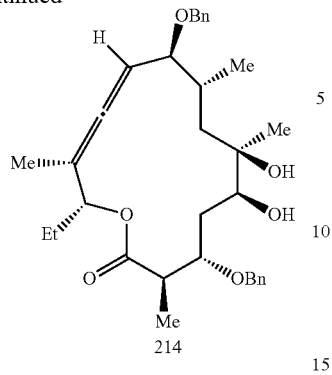

214

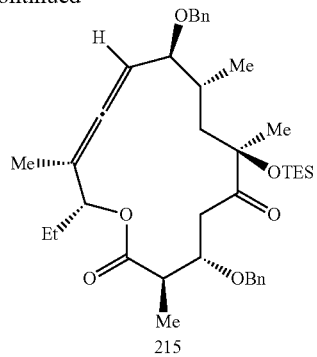

215

The hydroxyl ketone 130 (8.0 mg, 0.015 mmol, Example 12) was dissolved in 1 mL anhydrous diethyl ether, cooled to 0° C., then a 0.1 M solution of zinc borohydride (1 mL, 0.1 mmol) was added, stirred for 30 min then quenched with saturated NH$_4$Cl aqueous solution and extracted with ethyl acetate. The organic layer was dried over Na$_2$SO$_4$, filtered, and then concentrated under reduced pressure to give a crude product which was purified by flash column chromatography using 20% ethyl acetate in hexane to afford 214 as a colorless oil (5.4 mg, 0.010 mmol, 68% yield) as product: IR $v_{max}$ (neat)/cm$^{-1}$ 13454, 2968, 2933, 2875, 1729, 1455, 1371, 1182, 1067; $^1$H NMR (600 MHz, CDCl$_3$) δ 7.37-7.27 (m, 10H), 5.38 (m, 1H), 5.21 (m, 1H), 4.74 (d, J=12.3 Hz, 1H), 4.60 (d, J=11.1, 1H), 4.59 (d, J=11.1, 1H), 4.42 (d, J=12.3 Hz, 1H), 3.92 (m, 1H), 3.69 (dd, J=7.5, 5.5 Hz, 1H), 3.59 (m, 1H), 2.89 (s, 1H), 2.76 (dq, J=7.2, 6.9 Hz, 1H), 2.06 (m, 1H), 1.99 (dd, J=14.8, 5.3 Hz, 1H), 1.86 (dd, J=15.0, 3.4 Hz, 1H), 1.83 (dd, J=15.0, 7.1 Hz, 1H), 1.74 (d, J=3.0 Hz, 3H), 1.72 (m, 2H), 1.24 (d, J=6.9 Hz, 3H), 1.16 (s, 3H), 1.07 (dd, J=14.8, 3.8 Hz, 1H), 1.00 (d, J=6.9 Hz, 3H), 0.91 (t, J=7.3 Hz, 3H); $^{13}$C NMR (150 MHz, CDCl$_3$) δ 204.2, 174.8, 138.3, 138.0, 128.7, 128.6, 128.2, 128.1 (2), 127.8, 99.5, 91.7, 80.6, 79.7, 76.3, 74.6, 73.7, 73.1, 70.6, 44.0, 39.8, 34.1, 33.5, 27.1, 25.2, 19.9, 14.6, 14.2, 9.7; MS (ESI+) calculated for [C$_{33}$H$_{44}$O$_6$+Na]$^+$: 559.30. found: 559.30.

The macrolactone 130 (6.0 mg, 0.011 mmol) was dissolved in 1 mL DCM then 2,6-lutidine and TESOTf was added respectively at rt, stirred for 20 min at rt, and then quenched by addition of excess aqueous NH$_4$Cl solution. The organic layer was diluted with 10 mL DCM, separated, and then concentrated under reduced pressure to give the crude product which was purified with flash column chromatography (3% ethyl acetate in hexane) to afford the product 215 as a colorless oil (6.0 mg, 0.0093 mmol, 83% yield): IR $v_{max}$ (neat)/cm$^{-1}$ 2957, 2934, 2875, 1726, 1455, 1370, 1167, 1072; $^1$H NMR (500 MHz, CDCl$_3$) δ 7.43-7.14 (m, 10H), 5.16 (dd, J=6.2, 5.0 Hz, 1H), 5.04-4.90 (m, 1H), 4.60 (q, J=11.0 Hz, 2H), 4.47 (d, J=12.1 Hz, 1H), 4.22 (ddd, J=19.7, 10.9, 5.9 Hz, 1H), 4.12 (d, J=12.0 Hz, 1H), 4.05 (ddd, J=8.3, 6.0, 4.3 Hz, 1H), 3.49-3.35 (m, 1H), 3.15 (dd, J=16.9, 8.4 Hz, 1H), 2.88-2.82 (m, 1H), 2.82-2.75 (m, 1H), 1.91 (dt, J=10.2, 4.7 Hz, 2H), 1.78-1.74 (m, 2H), 1.73-1.63 (m, 2H), 1.39 (s, 3H), 1.35-1.28 (m, 3H), 1.28-1.23 (m, 3H), 1.21 (d, J=7.0 Hz, 3H), 1.07 (d, J=6.7 Hz, 3H), 0.98 (dt, J=6.4, 5.6 Hz, 6H), 0.72-0.60 (m, 6H), 0.57-0.47 (m, 3H). $^{13}$C NMR (101 MHz, CDCl$_3$) δ 212.9, 204.1, 174.1, 139.2, 138.6, 128.4, 128.4, 128.3, 128.0, 127.8, 127.5, 98.9, 92.4, 83.2, 82.4, 77.4, 76.4, 72.9, 70.3, 45.3, 42.7, 41.6, 34.3, 26.9, 25.1, 18.1, 15.7, 13.1, 9.3, 7.5, 7.1; MS (ESI+) calculated for [C$_{39}$H$_{56}$O$_6$Si$^+$ Na]$^+$: 671.3. found: 671.3.

Example 13

Example 14

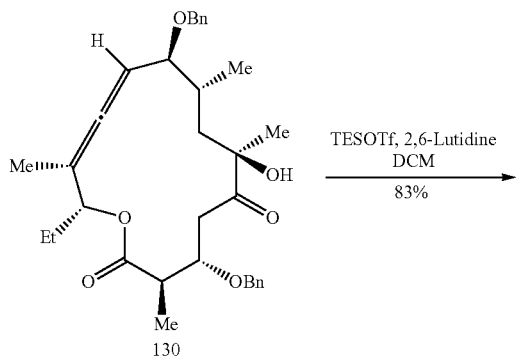

130

TESOTf, 2,6-Lutidine
DCM
83%

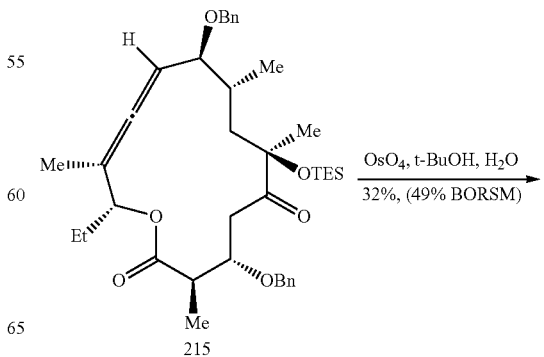

215

OsO$_4$, t-BuOH, H$_2$O
32%, (49% BORSM)

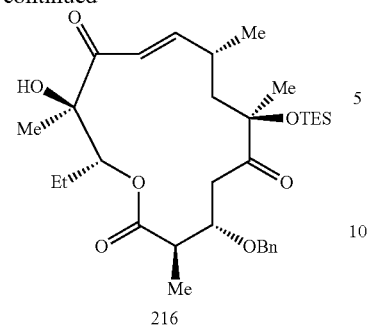

216

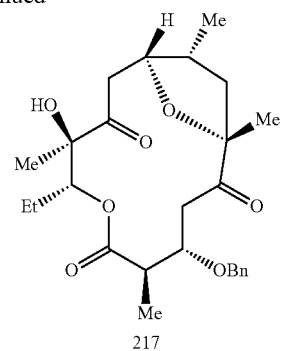

217

The protected ketoalcohol 215 (12.8 mg, 0.0200 mmol) was dissolved in 1 mL t-BuOH followed by the addition of citric acid (8.0 mg, 0.040 mmol) and the osmium tetroxide solution (0.13 mL, 4% wt. in water). The resulting dark purple solution was then stirred at rt for 3 h then the reaction was stopped by adding 10 mL saturated solution of sodium sulfite and extracted with 20 mL ethyl acetate. The organic layer was separated and then concentrated under reduced pressure to give a crude product which was purified by flash column chromatography using 10% ethyl acetate in hexane to afford product 216 as a colorless oil: (3.7 mg, 0.0064 mmol, 32% yield, 4.5 mg starting material recovered, 49% BORSM) IR $v_{max}$ (neat)/cm$^{-1}$ 3479, 2921, 2876, 2850, 1731, 1698, 1623, 1455, 1367; $^1$H NMR (600 MHz, CDCl$_3$) 7.33-7.28 (m, 5H); 6.64 (d, J=15.5 Hz, 1H), 6.60 (dd, J=8.2, 15.5 Hz, 1H), 4.89 (dd, J=2.5, 11.3 Hz, 1H), 4.56 (d, J=11.6 Hz, 1H), 4.49 (d, J=11.6 Hz, 1H), 3.68 (m, 1H), 3.60 (m, 1H), 3.42 (dd, J=4.3, 18.8 Hz, 1H), 2.58 (m, 1H), 2.44 (dd, J=3.4, 18.8 Hz, 1H), 2.29 (dd, J=10.2, 14.3 Hz, 1H), 2.02 (m, 1H), 1.78 (m, 1H), 1.45 (dd, J=2.1, 14.3 Hz, 1H), 1.31 (s, 3H), 1.23 (s, 3H), 1.21 (d, J=7.0 Hz, 3H), 1.02 (d, J=6.6 Hz, 3H), 1.01 (t, J=7.9, 9H), 0.88 (t, J=7.4 Hz, 3H), 0.66 (m, 6H); $^{13}$C NMR (150 MHz, CDCl$_3$) δ 212.5, 202.7, 178.5, 154.9, 138.5, 128.6, 128.3, 128.0, 122.7, 84.4, 82.4, 80.8, 77.1, 73.0 46.3, 43.0, 37.6, 33.3, 28.3, 23.6, 23.0, 22.5, 16.0, 10.9, 7.5, 7.0; MS (ESI+) calculated for [C$_{32}$H$_{50}$O$_7$Si$^+$ Na]$^+$: 597.3. found: 597.3.

The macrolactone 116 (10 mg, 0.02 mmol) was dissolved in a 1:1 mixture solution of t-BuOH and water (1 mL), then 0.28 mL OsO$_4$ solution (4% wt. in water) was added at rt, stirred for 4 h then quenched with 15 mL saturated sodium sulfite solution, and then extracted with diethyl ether (2×20 mL). The organic layers were combined, dried over Na$_2$SO$_4$, filtered, and then concentrated under reduced pressure to give a crude product, which was purified by flash column chromatography using 20% ethyl acetate and hexane to afford macrolactone 217 as a colorless oil: (4.4 mg, 0.0092 mmol, 46% yield) IR $v_{max}$ (neat)/cm$^{-1}$ 3477, 2971, 2934, 2878, 1735, 1711, 1455, 1382; $^1$H NMR (600 MHz, CDCl$_3$) δ 7.35-7.30 (m, 5H), 4.89 (dd, J=9.0, 3.4 Hz, 1H), 4.63 (m, 1H), 4.57 (d, J=11.6 Hz 1H), 4.59 (d, J=11.6 Hz 1H), 3.86 (m, J=11.1, 4.7 Hz, 1H), 3.37 (dd, J=14.5, 6.4 Hz, 1H), 3.08 (dd, J=18.7, 10.2 Hz, 1H), 2.98-2.82 (m, 1H), 2.51-2.36 (m, 1H), 2.29 (dd, J=4.7, 14.5 Hz, 1H), 1.97 (m, 1H), 1.89 (dd, J=12.9, 9.1 Hz, 1H), 1.79 (dd, J=12.9, 7.3 Hz, 1H), 1.55 (m, 1H), 1.38 (s, 3H), 1.27 (s, 3H), 1.21 (d, J=7.3 Hz, 3H), 0.93 (t, J=7.5 Hz, 3H), 0.67 (d, J=7.0 Hz, 3H); $^{13}$C NMR (150 MHz, CDCl$_3$) δ 213.3, 212.6, 173.2, 137.5, 128.8, 128.4, 128.0, 88.5, 78.9, 78.4, 77.8, 76.3, 72.0, 42.1, 40.5, 39.6, 35.4, 34.9, 25.2, 23.1, 17.0, 15.0, 14.2, 11.0; MS (ESI+) calculated for [C$_{26}$H$_{36}$O$_7$+Na]$^+$: 483.3. found: 483.3.

Example 15

Example 16

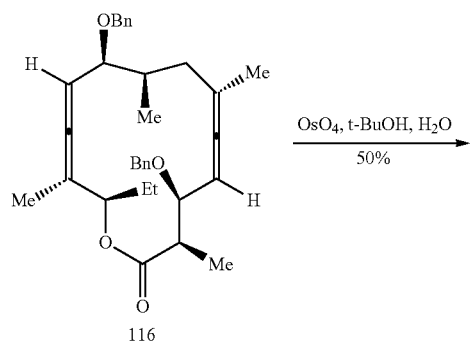

116

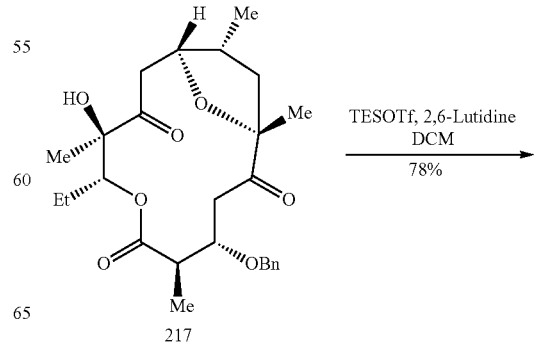

217

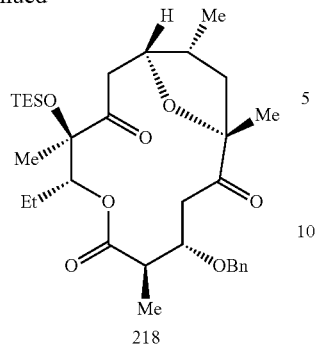

218

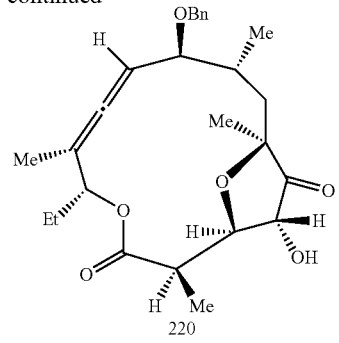

220

The keto-alcohol 217 (4.0 mg, 0.0082 mmol) was dissolved in 1.5 mL DCM then 2,6-lutidine (100 mg) and TESOTf (120 mg) was added respectively at rt, stirred at rt for 30 min then quenched by 10 mL saturated NH$_4$Cl solution. Organic layer was diluted with 10 mL DCM, separated then concentrated under reduced pressure to give the crude product, which was Further purified by flash column chromatography using 10% ethyl acetate in hexane to afford the product 218 as a colorless oil (4.0 mg, 78% yield), which could be converted to a white crystalline by slow evaporation at rt in 1 mL 30% ethyl acetate in hexane: IR ν$_{max}$ (neat)/cm$^{-1}$ 3444, 2954, 2928, 2875, 1738, 1716, 1456, 1378, 1183, 1164; $^1$H NMR (600 MHz, CDCl$_3$) δ 7.33-7.30 (m, 5H), 5.2 (dd, J=2.9, 9.5 Hz, 1H), 4.6 (d, J=10.4 Hz, 1H), 4.48 (m, 1H), 4.44 (d, J=10.4 Hz, 1H), 3.87 (m, 1H), 3.26 (dd, J=9.6, 14.9 Hz, 1H), 2.92 (m, 1H), 2.78 (dd, J=10.5, 19.0 Hz, 1H), 2.35 (dd, J=1.5, 19.0 Hz, 1H), 2.24 (m, 1H), 2.17 (dd, J=3.8, 14.9 Hz, 1H), 1.89 (m, 1H), 1.81 (dd, J=11.4, 12.6 Hz, 1H), 1.73 (dd, J=7.0, 12.6 Hz, 1H), 1.46 (m, 1H), 1.33 (s, 3H), 1.28 (s, 3H), 1.14 (d, J=7.0 Hz, 3H), 0.91 (t, J=7.2 Hz, 3H), 0.89 (dd, J=7.8, 8.2 Hz, 9H), 0.68 (d, J=6.9 Hz, 3H), 0.56-0.54 (m, 6H); $^{13}$C NMR (150 MHz, CDCl$_3$) δ 215.5, 211.4, 172.9, 137.7, 129.1, 128.5, 128.3, 88.6, 79.6 (2), 79.4, 78.1, 72.5, 41.6, 41.2, 39.8, 36.3, 35.0, 25.5, 22.7, 17.0, 14.8, 13.9, 11.1, 7.2, 6.4; MS (ESI+) calculated for [C$_{32}$H$_{50}$O$_7$Si$^+$Na]$^+$: 597.3. found: 597.3.

To a solution of macrolactone 116 (17.7 mg, 0.0340 mmol) in CDCl$_3$ (0.5 mL) was added a solution of DMDO (0.56 mL, 0.21 mmol) dropwise at −40° C., warmed up to −15° C. over 30 min, then lower order methyl cyanocuprate (MeCuCNLi, 0.71 mmol) was added, prepared by addition of MeLi (0.44 mL, 0.71 mmol) to a slurry of CuCN (63 mg, 0.71 mmol) in 2-methyl THF (5.99 mL) at −78° C. and then warming to −15° C. The mixture was warmed to −2° C. over 1.5 h, quenched with saturated aqueous solution of NH$_4$OH and NH$_4$Cl (1:4 ratio) and then extracted with diethyl ether. The combined organic layer was dried over anhydrous Na$_2$SO$_4$, filtered and then concentrated under reduced pressure to give the crude product, which was purified by flash column chromatography using 15% ethyl acetate in hexane to afford 220 (10 mg, 64% yield) as a colorless oil. For detailed NMR analysis, see page S30. IR vmax (neat)/cm$^{-1}$ 3434, 2968, 2925, 1959, 1764, 1725, 1452, 1370, 1155; $^1$H NMR (600 MHz, CDCl$_3$) δ 7.35-7.28 (m, 5H), 5.60 (dd, J=8.1, 6.3 Hz, 1H), 5.07 (m, 2H), 4.62 (d, J=12.1 Hz, 1H), 4.36 (d, J=12.1 Hz, 1H), 3.90 (dd, J=8.7, 4.4 Hz, 1H), 3.83 (dd, J=8.1, 2.6 Hz, 1H), 3.06 (m, 1H), 1.87 (dd, J=15.0, 5.8 Hz, 1H), 1.80 (d, J=2.8 Hz, 3H), 1.70 (m, 2H), 1.65 (m, 2H), 1.35 (d, J=7.4 Hz, 2H), 1.14 (s, 3H), 0.93 (t, J=7.6 Hz, 3H), 0.88 (d, J=7.0 Hz, 3H); $^{13}$C NMR (150 MHz, CDCl$_3$) δ 218.9, 206.6, 171.0, 138.9, 128.2, 127.7, 127.3, 99.0, 90.7, 83.4, 82.3, 79.7, 76.6, 72.5, 70.2, 42.9, 40.2, 34.0, 24.3, 22.8, 14.5, 13.8, 13.6, 10.0; MS (ESI+) calculated for [C$_{26}$H$_{34}$O$_6$+Na]$^+$: 465.2. found: 465.5. [α]$^{25}_D$=5.9° (c=0.005, CHCl$_3$).

Example 17

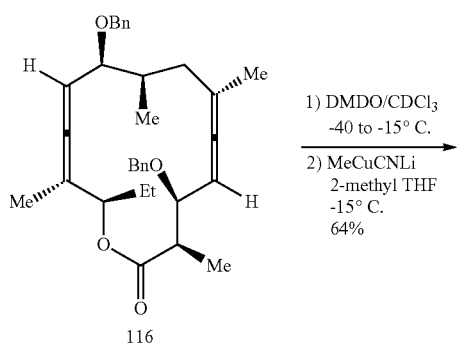

Example 18

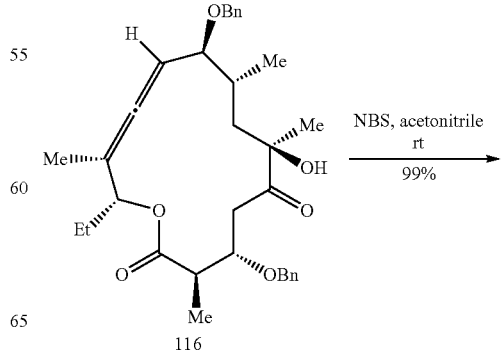

-continued

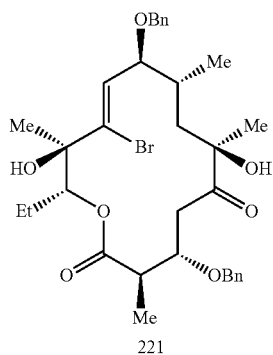

221

To a stirred solution of macrolactone 116 (7.8 mg, 0.015 mmol) in 1.0 mL of acetonitrile was added N-bromosuccinimide (34 mg, 0.19 mmol) at rt then stirred for 5 min. The reaction mixture was quenched with 1 mL of saturated aqueous solution of $Na_2S_2O_3$ and then extracted with diethyl ether (2×5 mL). The organic layer was separated and then concentrated under reduced pressure to give the crude product which was purified by flash column chromatography using 14% ethyl acetate in hexane to afford 221 as colorless oil: (9.1 mg, 99% yield). For detailed NMR analysis, see page S32. IR vmax (neat)/cm$^{-1}$ 3442, 3062, 2956, 2922, 2850, 1728, 1711, 1454, 1376, 1165, 1070; $^1$H NMR (600 MHz, CDCl$_3$) δ 7.37-7.24 (m, 10H), 6.14 (d, J=8.4 Hz, 1H), 4.89 (dd, J=10.9, 2.4 Hz, 1H), 4.64 (d, J=11.1 Hz, 1H), 4.52 (m, 2H), 4.40 (d, J=12.3 Hz, 1H), 4.34 (m, 1H), 4.00 (dd, J=8.3, 6.1 Hz, 1H), 3.11 (dd, J=15.6, 6.4 Hz, 1H), 2.56 (q, J=6.9 Hz, 1H), 2.47 (dd, J=15.6, 5.7 Hz, 1H), 1.85 (m, 1H), 1.82 (m, 1H), 1.79 (dd, J=14.4 Hz, 1H), 1.55 (m, 1H), 1.45 (dd, J=14.4, 5.9 Hz, 1H), 1.44 (s, 3H), 1.23 (s, 3H), 1.20 (d, J=6.9 Hz, 3H), 1.05 (d, J=6.6 Hz, 3H), 0.80 (t, J=7.4 Hz, 3H); $^{13}$C NMR (150 MHz, CDCl$_3$) δ 212.7, 174.6, 138.7, 138.4, 134.2, 131.2, 128.3 (2), 128.1, 127.7 (2), 127.5, 84.0, 79.4, 79.3, 77.1, 76.1, 73.3, 72.2, 44.8, 42.5, 41.3, 35.0, 26.8, 25.1, 24.4, 19.6, 12.6, 11.1; MS (ESI+) calculated for $[C_{33}H_{43}BrO_7+Na]^+$: 653.3, 655.3. found: 653.2, 655.2. $[α]^{25}_D$=7.6° (c=0.005, CHCl$_3$).

Example 19

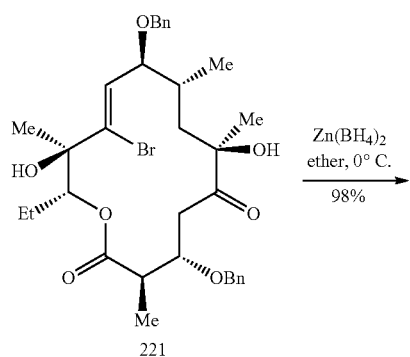

221

-continued

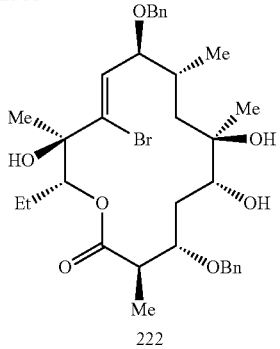

222

To a stirred solution of macrolactone 221 (5.0 mg, 0.0079 μmol) in 1.00 mL of anhydrous diethyl ether was added 0.13 M Zn(BH$_4$)$_2$ solution in anhydrous diethyl ether (0.090 ml, 0.012 mmol) at 0° C. The mixture was stirred for 30 mins at 0° C., quenched with 1 mL of saturated aqueous solution of NH$_4$Cl, then extracted with diethyl ether (2×5 mL). The organic layer was separated, dried over Na$_2$SO$_4$, filtered then concentrated under reduced pressure to give the crude product, which was purified by flash column chromatography 20% ethyl acetate in hexane to afford 222 (4.9 mg, 98% yield) as an oil. For detailed NMR analysis, see page S34. IR vmax (neat)/cm$^{-1}$ 2925, 2851, 1729, 1450, 1375, 1164, 1068; $^1$H NMR (600 MHz, CDCl$_3$) δ 7.39-7.23 (m, 10H) 6.38 (d, J=8.6 Hz, 1H), 4.88 (dd, J=11.0, 2.3 Hz, 1H), 4.58 (m, 2H), 4.51 (d, J=10.7 Hz, 1H), 4.47 (d, J=12.4 Hz, 1H), 4.36 (m, 1H), 4.11 (dd, J=8.6, 6.6 Hz, 1H), 3.51 (dd, J=7.0, 2.4 Hz, 1H), 2.65 (m, 1H), 2.31 (m, 1H), 1.85 (m, 2H), 1.83 (dd, J=15.0, 3.0 Hz, 1H), 1.77 (dd, J=15.0, 3.0 Hz, 1H), 1.61 (dd, J=14.7, 6.1 Hz, 1H), 1.50 (s, 3H), 1.28 (s, 3H), 1.27 (d, J=7.0 Hz, 3H), 1.17 (dd, J=14.9, 7.0 Hz, 1H), 1.12 (d, J=6.7 Hz, 3H), 0.89 (t, J=7.4 Hz, 3H); $^{13}$C NMR (150 MHz, CDCl$_3$) δ 176.8, 139.0, 137.9, 133.0, 131.4, 128.3, 128.1, 128.0, 127.9, 127.6, 126.5, 84.7, 81.3, 78.2, 77.6, 75.2, 73.7, 73.1, 71.9, 44.8, 40.8, 35.9, 34.6, 27.7, 26.0, 24.7, 20.0, 12.4, 11.4; MS (ESI+) calculated for $[C_{33}H_{45}O_7+Na]^+$: 655.2, 657.2. found: 655.2, 657.2. $[α]^{25}_D$=5.8° (c=0.005, CHCl$_3$).

Example 20

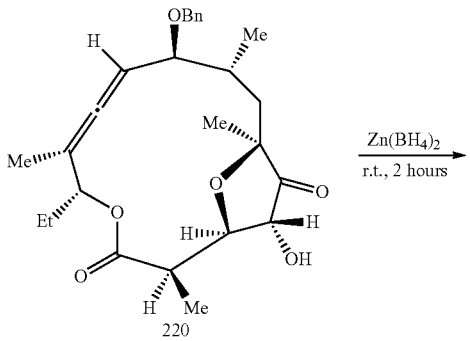

220

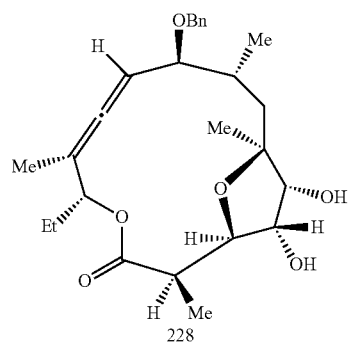

228

To 220 (1.7 mg, 3.18 μmol) in diethyl ether (1 ml) was added a 0.3M solution of Zn(BH₄)₂ (2 eq, 46 μl, 14 μmol) dropwise at −0° C., then 0.3M solution of Zn(BH₄)₂ (5 eq, 115 μl, 35 μmol) twice at rt. After the complete consumption of the starting materials, the reaction was then quenched with aqueous NH₄Cl and extracted with diethyl ether. The combined organic phase was dried over anhydrous Na₂SO₄. Evaporation of solvent and flash column chromatography purification using 15% EtOAc in hexanes gave a mixture of 228 (1.4 mg, 82% yield) as colorless oil. $^1$H NMR (600 MHz, CDCl₃) δ 7.35-7.30 (m, 5H), 4.56 (d, J=9.29 Hz, 1H), 4.50 (d, J=11.0 Hz, 1H), 4.33 (d, J=11.0 Hz, 1H), 4.19-4.10 (m, 1H), 4.09-4.00 (m, 1H), 3.95 (dd, J=9.05, 5.14 Hz, 1H), 3.41 (dd, J=13.7, 9.5 Hz, 1H), 3.29 (dt, J=12.3, 7.2 Hz, 1H), 3.11 (s, 1H), 2.50 (dd, J=13.7, 3.8 Hz, 1H), 2.34 (s, 1H), 1.76-1.73 (m, 1H), 1.69-1.60 (m, 3H), 1.47 (s, 3H), 1.30 (d, J=7.34, 3H), 1.26 (m, 1H), 1.21 (s, 3H), 1.05 (t, J=7.33, 3H), 0.85 (d, J=6.85, 3H); $^{13}$C NMR (150 MHz, CDCl₃) δ 202.53, 171.93, 136.00, 128.65, 128.26, 127.82, 101.34, 99.52, 93.79, 85.06, 79.27, 77.43, 75.77, 71.47, 70.56, 64.04, 55.25, 53.71, 39.24, 34.94, 29.92, 25.64, 19.73, 18.26, 16.97, 12.04, 9.09, 1.25, 0.22; m/z (HRMS) found: 535.30451 (M+H)⁺. calc'd: 535.30542.

Example 21

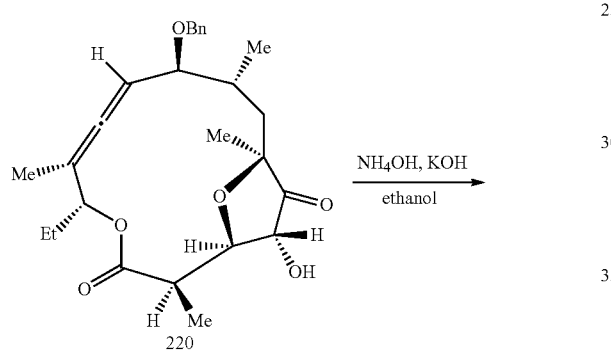

To a solution of 220 (3.4 mg, 7.7 μl) in ethanol (1 ml) was added hydroxylamine hydrochloride (16 mg, 0.23 mmol). The reaction mixture was stirred for 2 hrs, then KOH (12.9 mg, 0.230 mmol) was added at rt. The reaction was diluted with water and extracted with diethyl ether. The combined organic phase was dried over anhydrous Na₂SO₄. Evaporation of solvent and flash column chromatography purification using 15% EtOAc in hexanes gave 229 (2.7 mg, 6.0 μmol) as colorless oil. $^1$H NMR (500 MHz, CDCl₃) δ 7.35-7.31 (m, 5H), 5.83 (d, J=6.60 Hz, 1H), 5.57 (dd, J=8.80, 5.58 Hz, 1H), 5.07-5.03 (m, 1H), 4.61 (d, J=11.74, 1H), 4.34 (d, J=11.99, 1H), 3.93 (dd, J=6.36, 4.40, 1H), 3.79 (dd, J=9.05, 1.46, 1H), 3.09 (s, 1H), 2.98-2.91 (m, 1H), 2.03-1.96 (m, 1H), 1.76 (d, J=2.69, 3H), 1.73-1.60 (m, 4H), 1.31 (d, J=8.56, 3H), 0.93 (d, J=7.33, 3H), 0.91 (s, 3H), 0.90-0.84 (m, 3H).

Example 22

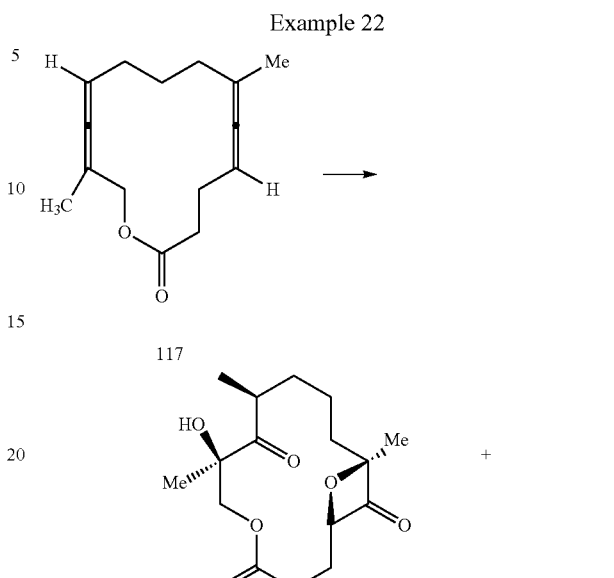

To a solution of freshly prepared dimethyldioxirane (DMDO) in CHCl₃ (12.9 mL, 2.586 mmol) was added bis[allene]macrolactone 117 (120 mg, 0.517 mmol) in CHCl₃ dropwise at −40° C. The reaction was stirred under nitrogen and let to warm to room temperature over 2 hours. Solvent was evaporated and the resulting bis[SDE] was used as such for the next step. Lower order methyl cyanocuprate was prepared by adding MeLi (3.2 mL, 5.12 mmol) to a slurry of CuCN (460 mg, 5.86 mmol) in diethyl ether (50 mL) at −40° C. and then warming to 0° C. The cuprate was cooled back to −40° C. and to that a ether solution (2 ml) of bis[SDE] was added slowly. The reaction was warmed to room temperature over 2 hours. The reaction was quenched with saturated NH₄Cl (10 mL) and extracted with Et₂O (3×20 mL) The combined organic phase was washed with water (10 mL), brine (10 mL) and dried over anhydrous MgSO₄. Evaporation of solvent and flash column chromatography purification using 15% EtOAc in hexanes gave a mixture of 251 and 250 (63 mg) as colorless oil. Based on 1.4:1 ratio of the product mixture by $^1$H NMR, the yield calculated for 251 and 250 are 22% and 16% respectively. 251 (white solid) and 250 (white solid) were then separated by 4 more flash column chromatography purifications. Compound 251: MP 118° C.; IR ν$_{max}$ (neat)/cm⁻¹ 3473, 2938, 1737, 1706, 1457, 1374; δ$_H$ (500 MHz, CDCl₃) 4.37 (1H, d, J=12.0 Hz), 4.28 (1H, s), 4.22 (1H, d, J=12.0 Hz), 4.04 (1H, s), 2.98-2.92 (1H, m), 2.78-2.72 (1H, m), 2.38 (2H, J=6.5 Hz), 2.10-2.02 (1H, m), 1.90-1.82 (1H, m), 1.76-1.66 (2H, m), 1.44 (3H, s), 1.41 (3H, s), 1.38-1.24 (3H, m), 1.15 (3H, d, J=7.0 Hz), 1.12 (3H, d, J=7.0 Hz), 0.88-0.80 (1H, m); δ$_C$ (125 MHz, CDCl₃) 217.8, 214.4, 172.1, 78.9, 77.9, 68.9, 41.1, 39.0, 38.3, 35.7, 31.6, 28.0, 25.6,

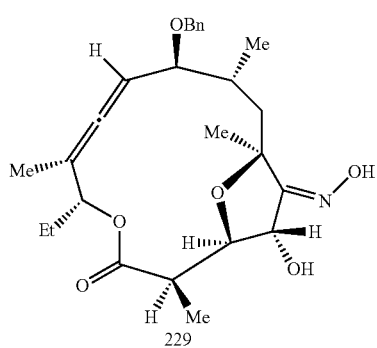

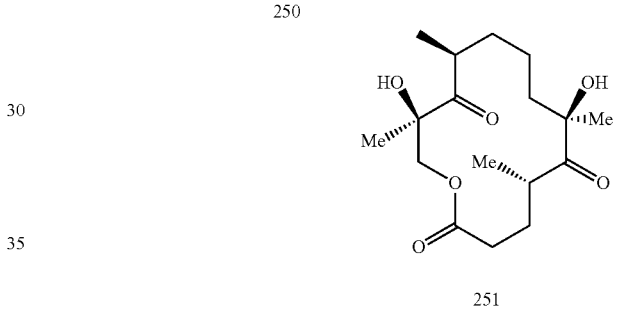

22.0, 20.8, 20.5, 18.6; m/z (ESIMS) found: 351.3. calc'd for C$_{17}$H$_{28}$NaO$_6$ [M+Na]+: 351.2. Slow evaporation of a sample of compound 251 dissolved in 0.2 mL hexanes and minimum amount of DCM gave crystals suitable for single crystal X-ray analysis. Compound 250: MP 151° C.; IR v$_{max}$ (neat)/cm$^{-1}$ 3477, 2928, 1811, 1740, 1709, 1462; 5.42 (1H, dd, J=4.5, 3.0 Hz), 4.35 (1H, d, J=12.0 Hz), 4.25 (1H, s), 4.14 (1H, d, J=12.0 Hz), 3.04-2.96 (1H, m), 2.51 (1H, ddd, J=18.0, 8.0, 3.0 Hz), 2.36 (1H, ddd, J=16.0, 10.0, 3.5 Hz), 2.20-2.08 (2H, m), 2.06-1.98 (1H, m), 1.76-1.68 (1H, m), 1.56-1.50 (1H, m), 1.45 (6H, s), 1.36-1.28 (2H, m), 1.15 (3H, J=6.5 Hz), 0.90-0.86 (1H, m); δ$_C$ (125 MHz, CDCl$_3$) 215.7, 206.8, 172.3, 105.6, 96.0, 77.8, 68.9, 40.1, 36.2, 33.9, 30.6, 24.4, 23.2, 22.2, 21.6, 20.3; m/z (ESIMS) found: 335.2. calc'd for C16H$_{24}$NaO$_6$ [M+Na]+: 335.1. Slow evaporation of a sample of compound 250 dissolved in 0.2 mL hexanes and minimum amount of DCM gave crystals suitable for single crystal X-ray analysis.

Example 23

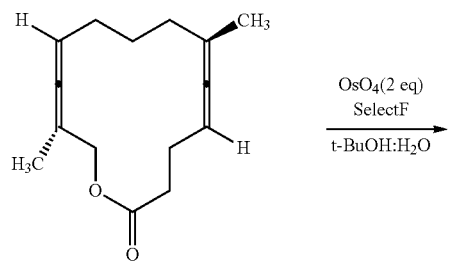

117

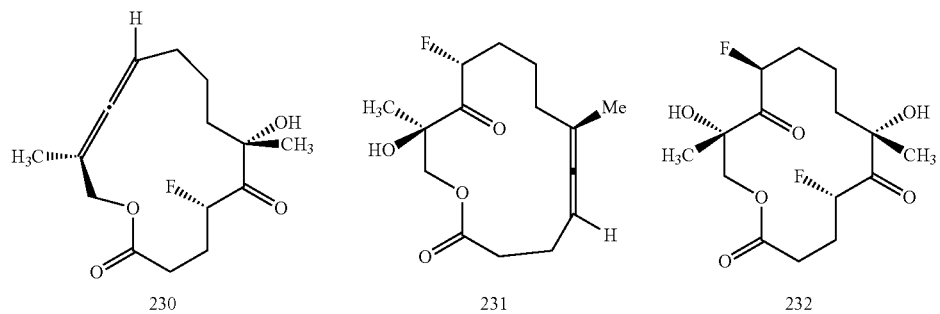

230
9.4% (mixture of 1.2 and 1.3)

231

232
(41.8%)

To the solution of allene (10.4 mg, 45.0 µmol) 117 in t-BuOH (2.0 mL) and water (1.3 mL) was added SelectFluor (109 mg, 448 µmol) at r.t. The mixture was stirred for 7 min, then 4% aq. OsO$_4$ solution (700 µL, 90 µmol) was added slowly. After the complete disappearance of allene on TLC, the reaction mixture was quenched by Sat'd solution of sodium sulfite and the organic layer was extracted in ethyl acetate. The crude was purified by flash column chromatography, yielding the mixture of 230 and 231 (1.2 mg, 9.4% combined yield) and 232 (6.3 mg, 42% yield). Compound 230 IR v$_{max}$ (neat)/cm$^{-1}$ 3433, 2921, 2850, 1736, 1461, 1372, 1241, 1158; m/z (HRMS) found: 307.13 (M+Na)$^+$. calc'd: 307.13. Compound 231; IR v$_{max}$ (neat)/cm$^{-1}$ 13479, 2927, 2833, 1727, 1455, 1372, 1230, 1162; m/z (HRMS) found: 359.13 (M+Na)$^+$. calc'd: 359.13 (M+Na)$^+$.

Example 24

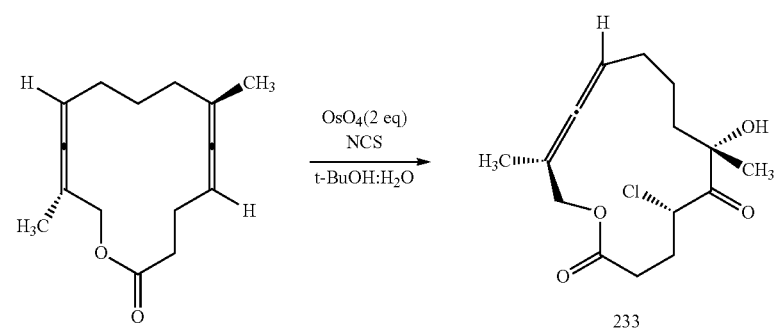

117

233
(7.4%)

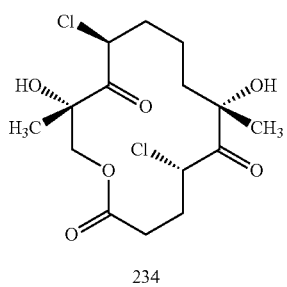

234
(64.7%)

To the solution of allene (10.5 mg, 45 µmol) 117 in t-BuOH (400 µL) and water (50 µL) was added NCS (30 mg, 226 µmol) at rt. The mixture was stirred for 20 min, then 4% aq. OsO$_4$ solution (703 µL, 90 µmol) was added slowly. After the complete disappearance of allene on TLC, the reaction mixture was quenched by Sat'd solution of sodium sulfite and the organic layer was extracted in ethyl acetate. The crude was purified by flash column chromatography, yielding compound 233 (1.0 mg, 7% yield) and compound 234 (10.8 mg, 65% yield). Compound 233: IR $v_{max}$ (neat)/cm$^{-1}$ 3492, 2929, 1723, 1461, 1371, 1211, 1154; m/z (HRMS) found: 323.10 (M+Na)$^+$. calc'd: 323.10. Compound 234; IR $v_{max}$ (neat)/cm$^{-1}$ 3433, 2920, 2850, 1739, 1462, 1375, 1241, 1157; m/z (HRMS) found: 367.07, 369.07, 372.07 (M+H)$^+$. calc'd: 367.07, 369.07, 372.07 (M+H)$^+$.

Example 25

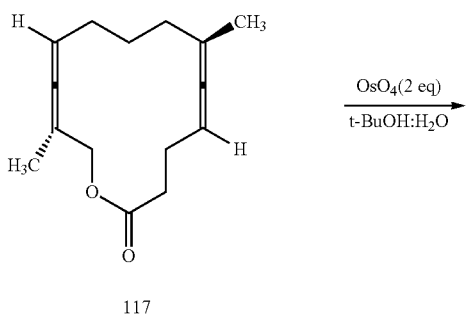

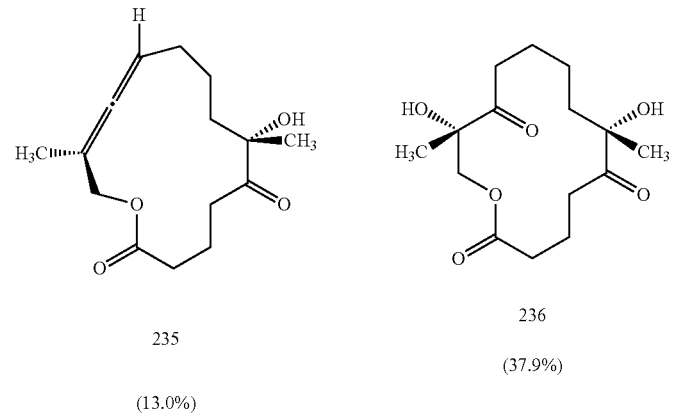

To the solution of allene (9.4 mg, 40 µmol) 117 in t-BuOH (400 µL) and water (50 µL) was added 4% aq. OsO$_4$ solution (635 µL, 81 µmol) was added slowly. After the complete disappearance of allene on TLC, the reaction mixture was quenched by Sat'd solution of sodium sulfite and the organic layer was extracted in ethyl acetate. The crude was purified by flash column chromatography, yielding compound 235 (1.4 mg, 13% yield). And compound 236 (4.6 mg, 38% yield). Compound 235; m/z (HRMS) found: 323.15 (M+Na)$^+$. calc'd: 323.15 (M+Na)$^+$.

Example 26

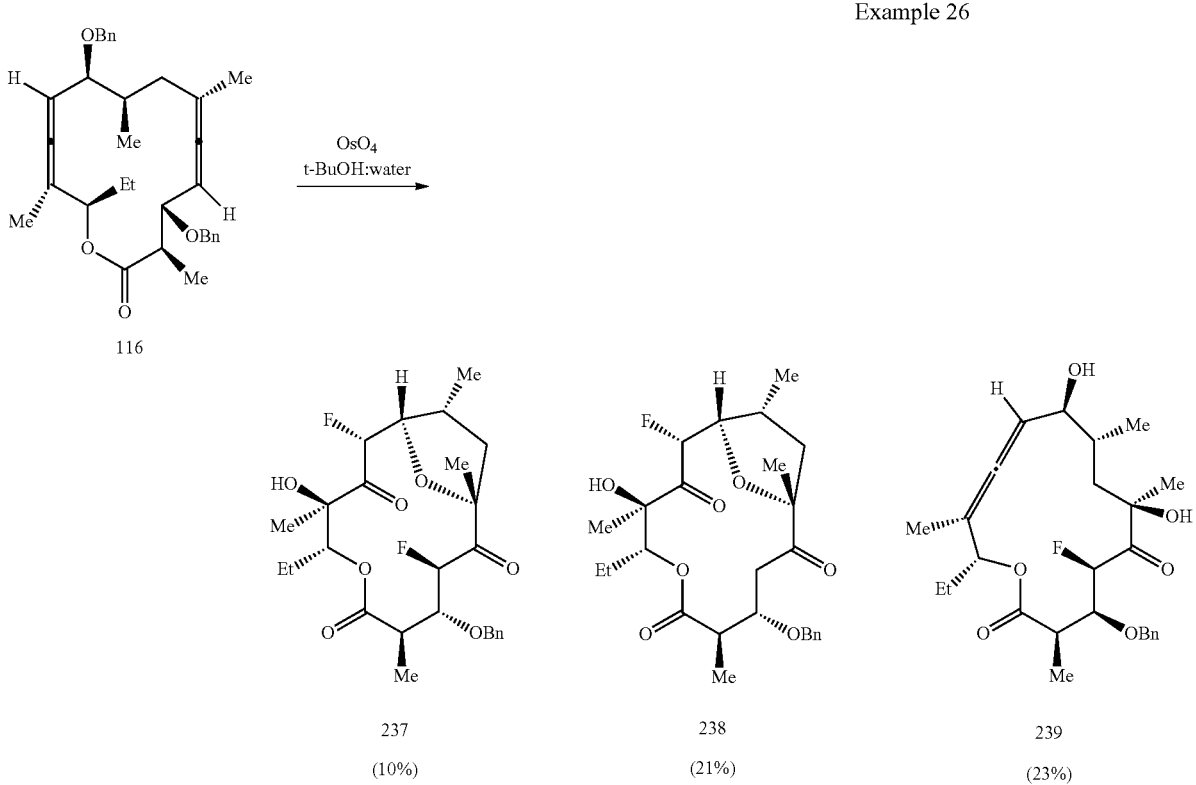

To the solution of allene (25 mg, 45 μmol) 116 in t-BuOH (1.00 mL), water (266 μL), and acetone (2.0 mL) was added SelectFluor (177 mg, 500 μmol) at rt. The mixture was stirred for 5 min, then 4% aq. OsO$_4$ solution (1.2 mL, 90 μmol) was added slowly. After the complete disappearance of allene on TLC, the reaction mixture was quenched by Sat'd solution of sodium sulfite and the organic layer was extracted in ethyl acetate. The crude was purified by flash column chromatography, yielding compound 237 (2.6 mg, 10% yield), compound 238 (5 mg, 21% yield) and compound 239 (5.2 mg, 23% yield). compound 237; IR ν$_{max}$ (neat)/cm$^{-1}$ 3452, 2952, 2922, 2851, 1737, 1456, 1377, 1068; m/z (HRMS) found: 519.22 (M+Na)$^+$. calc'd: 519.22. compound 238; IR ν$_{max}$ (neat)/cm$^{-1}$ 3500, 2918, 2849, 1736, 1455, 1375, 1169, 1011; m/z (HRMS) found: 501.22 (M+Na)$^+$. calc'd: 501.22. compound 239; IR ν$_{max}$ (neat)/cm$^{-1}$ 13434, 2916, 2848, 1734, 1496, 1372, 1184, 1027; m/z (HRMS) found: 485.23 (M+Na)$^+$. calc'd: 485.23 (M+Na)$^+$.

Example 27

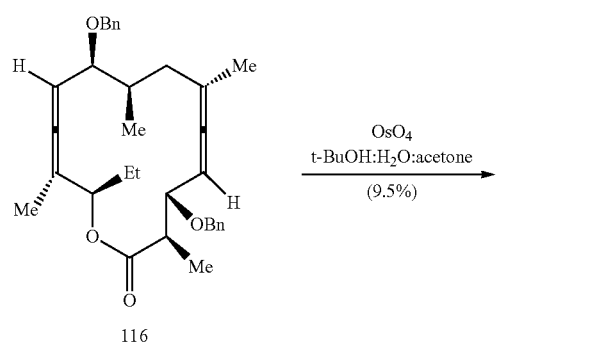

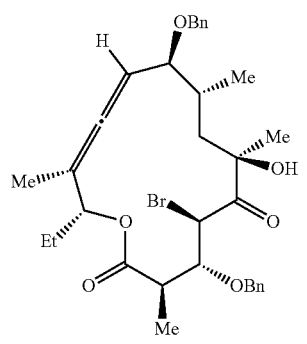

240

To the solution of allene (20.7 mg, 41 μmol) 116 in t-BuOH (1.00 mL), phosphate buffer, pH=4, (286 μL), and acetone (0.50 mL) was added 4% aq. OsO$_4$ solution (714 μL, 91 μmol) slowly. To the mixture was added NBS, dissolved in t-BuOH (0.50 mL), phosphate buffer, pH=4, (0.50 mL), and acetone (0.50 mL). After the complete disappearance of allene on TLC, the reaction mixture was quenched by Sat'd solution of sodium sulfite and the organic layer was extracted in ethyl acetate. The crude was purified by flash column chromatography, yielding compound 240 (2.5 mg, 9.5% yield). Compound 240: m/z (HRMS) found: 635.19, 637.19 (M+Na)$^+$. calc'd: 635.19, 637.19 (M+Na)$^+$.

Example 28

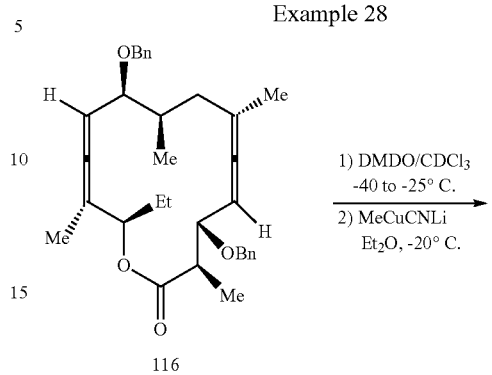

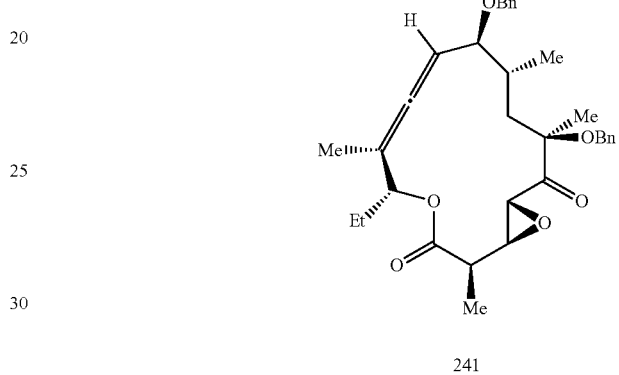

241

To bis[allene]macrolactone 116 (21.4 mg, 0.04 mmol) in CDCl$_3$ was added a solution of DMDO (850 μL, 0.12 mmol) dropwise at −40° C. The temperature was increased to −20° C. over 1 hr. Excess DMDO was removed under reduced pressure −20° C. Lower order methyl cyanocuprate was prepared by addition MeLi (0.27 mL, 0.43 mmol) to a slurry of CuCN (38 mg, 0.43 mmol) in Et$_2$O (4.27 mL) at −78° C. and then warming to −15° C. To the solution of SDE was added a solution of cuprate (200 μL, 0.02 mmol) at −20° C. After the consumption of SDE, the reaction was then quenched with Sat'd NH$_4$Cl and extracted with Et$_2$O. The combined organic phase was dried over anhydrous Na$_2$SO$_4$. Evaporation of solvent and flash column chromatography purification using 15% EtOAc in hexane gave compound 241 (6.8 mg, 30% yield) as colorless oil. Compound 241; IR ν$_{max}$ (neat)/cm$^{-1}$ 3436, 3063, 3031, 2969, 2933, 2876, 1966, 1785, 1729, 1454, 1376, 1270, 1179, 1065; m/z (HRMS) found: 555.27 (M+Na)$^+$. calc'd: 555.28. [α]25$^D$=11.1° (c=0.005, CHCl$_3$).

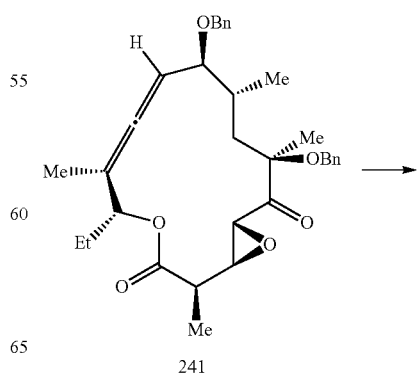

241

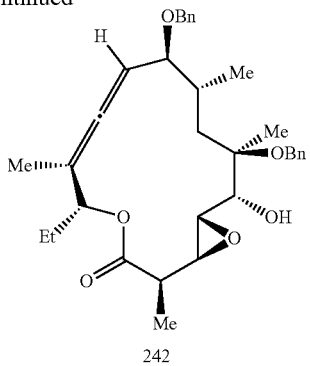

242

To epoxy ketone 241 (1.7 mg, 3.2 μmol) in diethyl ether (1.00 mL) was added a 0.3M solution of Zn(BH$_4$)$_2$ (2 equiv, 46 μl, 14 μmol) dropwise at −0° C., then 0.3M solution of Zn(BH$_4$)$_2$ (5 equiv, 115 μl, 35 μmol) twice at rt. After the complete consumption of the starting materials, the reaction was then quenched with aqueous NH$_4$Cl and extracted with diethyl ether. The combined organic phase was dried over anhydrous Na$_2$SO$_4$. Evaporation of solvent and flash column chromatography purification using 15% EtOAc in hexanes gave compound 242 (1.4 mg, 82% yield) as colorless oil. $^1$H NMR (600 MHz, CDCl$_3$) δ 7.35-7.30 (m, 5H), 4.56 (d, J=9.29 Hz, 1H), 4.50 (d, J=11.0 Hz, 1H), 4.33 (d, J=11.0 Hz, 1H), 4.19-4.10 (m, 1H), 4.09-4.00 (m, 1H), 3.95 (dd, J=9.05, 5.14 Hz, 1H), 3.41 (dd, J=13.7, 9.5 Hz, 1H), 3.29 (dt, J=12.3, 7.2 Hz, 1H), 3.11 (s, 1H), 2.50 (dd, J=13.7, 3.8 Hz, 1H), 2.34 (s, 1H), 1.76-1.73 (m, 1H), 1.69-1.60 (m, 3H), 1.47 (s, 3H), 1.30 (d, J=7.34, 3H), 1.26 (m, 1H), 1.21 (s, 3H), 1.05 (t, J=7.33, 3H), 0.85 (d, J=6.85, 3H); $^{13}$C NMR (150 MHz, CDCl$_3$) δ202.53, 171.93, 136.00, 128.65, 128.26, 127.82, 101.34, 99.52, 93.79, 85.06, 79.27, 77.43, 75.77, 71.47, 70.56, 64.04, 55.25, 53.71, 39.24, 34.94, 29.92, 25.64, 19.73, 18.26, 16.97, 12.04, 9.09, 1.25, 0.22; m/z (HRMS) found: 535.30451 (M+H)$^+$. calc'd: 535.30542.

Example 30

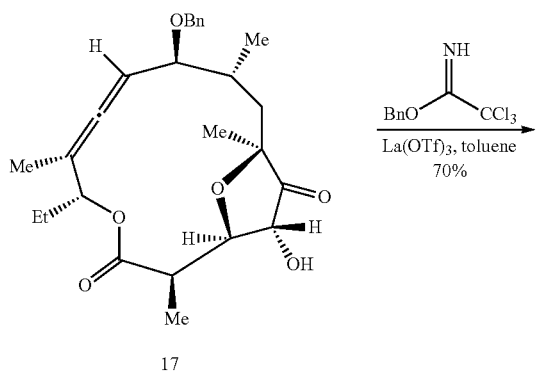

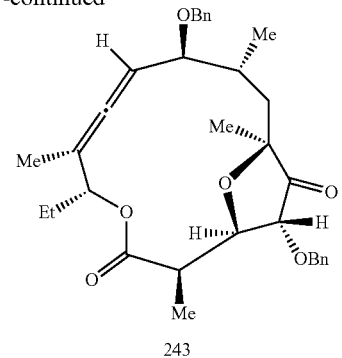

243

To a stirred solution of macrolactone 17 (10 mg, 23 μmol) in 155 uL of toluene (148 mM) were added benzyl trichloroacetimidate (8 mg, 32 μmol) and Lanthanium triflate (0.7 mg, 1 μmol). Then the mixture was stirred at r.t. for 30 min. The reaction mixture was concentrated under vacuum and the residue was subjected to purification by flash column chromatography, yielding compound 243 (8.4 mg, 70%). Compound 243: IR ν$_{max}$ (neat)/cm$^{-1}$ 3400, 2965, 2923, 2877, 2851, 1900, 1759, 1725, 1453, 1374, 1186, 1046; m/z (HRMS) found: 555.27 (M+Na)$^+$. calc'd: 557.27 (M+Na)$^+$.

Example 31

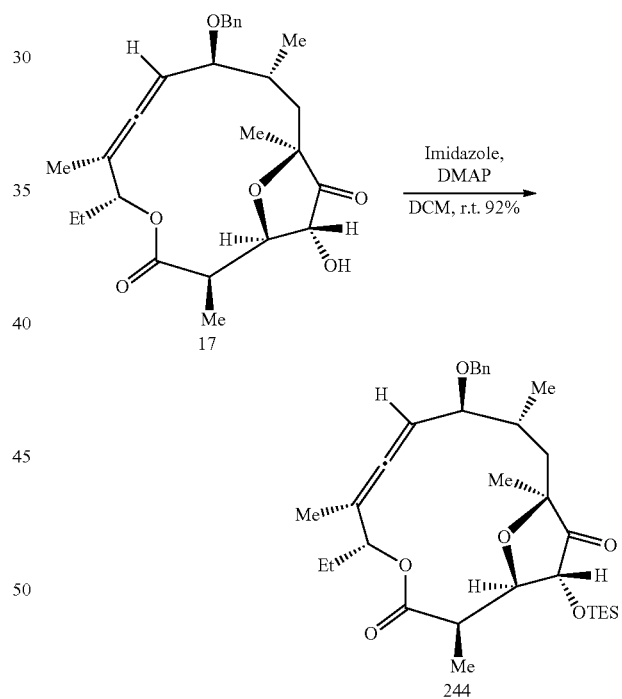

To the solution of compound 17 (6.2 mg, 14 μmol) in 1.0 mL of anhydrous DCM was added imidazole (2.9 mg, 0.04 mmol) and DMAP (0.5 mg, 4.2 μmol). After stirring for 5 min at rt, triethylsilyl chloride (TESCl) was added to the mixture at rt. Upon the completion of the reaction, the mixture was quenched with Sat'd NH$_4$Cl and the organic layer was extracted with DCM, dried over sodium sulfate. The crude was chromatographed with 3% ethyl acetate in hexane through silica gel and the product 244 was obtained in 92% yield (7.2 mg, 13 μmol). Compound 244: IR ν$_{max}$ (neat)/cm$^{-1}$ 3439, 2957, 2931, 2987, 2858, 1723, 1471, 1376, 1195, 1103, 837; m/z (HRMS) found: 557.33 (M+H)$^+$. calc'd: 557.33 (M+H)$^+$.

Example 32

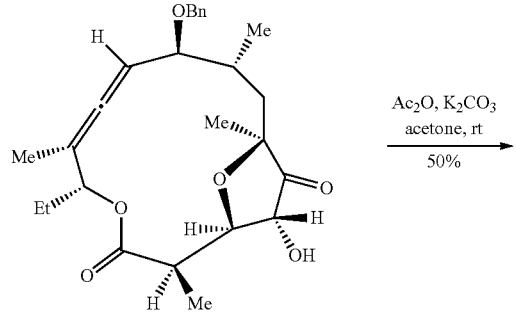

17

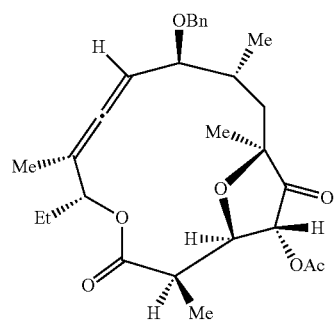

245

To a solution of alcohol 17 (3.1 mg, 7.0 μmol) in acetone (500 μl) was added a grinded K$_2$CO$_3$ (9.6 mg, 70 μmol) and stirred for 30 min at room temperature. To the mixture was added acetic anhydride (6 μl, 70 μmol) at room temperature and stirred for overnight. The reaction mixture was diluted in DCM and the organic layer was washed with water. The combined organic phase was dried over anhydrous Na$_2$SO$_4$. Evaporation of solvent and flash column chromatography purification using 7% EtOAc in hexanes gave compound 245 (1.7 mg, 50% yield) as colorless oil. Compound 245: m/z (HRMS) found: 507.24 (M+Na)$^+$. calc'd: 507.24 (M+Na)$^+$.

Example 33

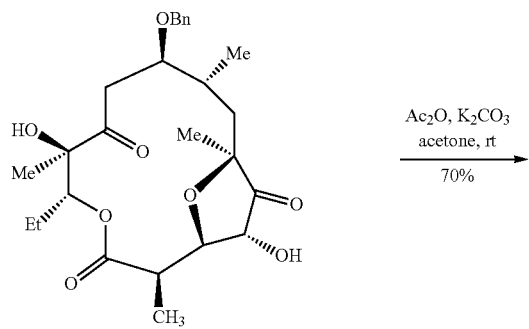

252

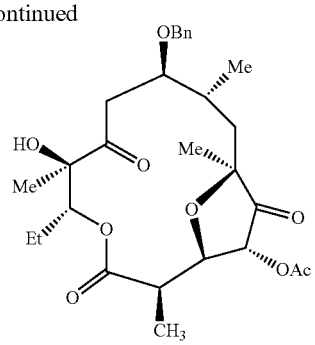

246

To a solution of alcohol 1.19 (7.4 mg, 16 μmol) in acetone (500 μl) was added powdered K$_2$CO$_3$ (4.3 mg, 31 μmol) and stirred for 30 min at room temperature. To the mixture was added acetic anhydride (6 μl, 70 μmol) at room temperature and stirred for overnight. The reaction mixture was diluted in DCM and the organic layer was washed with water. The combined organic phase was dried over anhydrous Na$_2$SO$_4$. Evaporation of solvent and flash column chromatography purification using 7% EtOAc in hexanes gave compound 246 (5.6 mg, 70% yield) as colorless oil. Compound 246: m/z (HRMS) found: 541.24 (M+Na)$^+$. calc'd: 541.24 (M+Na)$^+$.

Example 34

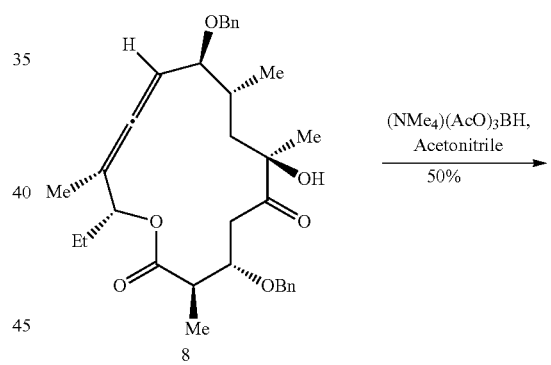

8

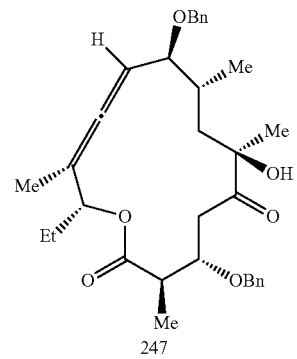

247

The hydroxyl ketone 8 (4.0 mg, 0.0075 mmol) was dissolved in 1 mL acetonitrile, then tetramethylammoniumtriacetoxyborohydride powder was added in one portion followed by the addition of 20 mg acetic acid, stirred for 48 hours at room temperature then quenched with saturated NH$_4$Cl aqueous solution and extracted with ethyl acetate. The organic layer was dried over Na$_2$SO$_4$, filtered and then concentrated under reduced pressure to give a crude product which was purified by flash column chromatography using 20% ethyl acetate in hexane to afford compound 247 as a colorless oil (2.0 mg, 0.0037 mmol, 50% yield) as product: MS (ESI+) calculated for [C$_{33}$H$_{44}$O$_6$+Na]$^+$: 559.30. found: 559.30. (Same product could be obtained by using sodium borohydride as reductant instead of tetramethylammoniumtriacetoxyborohydride to give a 1:1 mixture of diastereomers instead of single isomer.)

Example 35

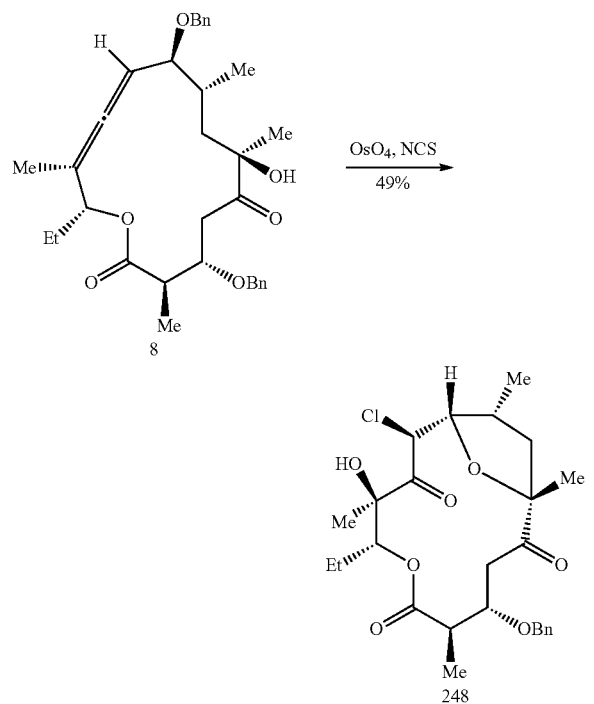

8

248

The hydroxyl ketone 8 (7.0 mg, 0.013 mmol) was dissolved in 0.5 mL t-butanol and 0.2 mL water. To this solution was added OsO$_4$ (0.165 mL, 4% wt. solution in water, 0.026 mmol). Then a solution of NCS (5.0 mg, 0.040 mmol) in 0.6 mL 1:1:1 mixture of t-butanol, water and acetone was delivered by syringe pump over 3 hours into the reaction mixture, stirred for another 5 hours, quenched with excess sodium sulfite and then extracted with ethyl acetate. The organic layer was dried over Na$_2$SO$_4$, filtered and then concentrated under reduced pressure to give a crude product which was purified by flash column chromatography using 10% ethyl acetate in hexane to afford compound 248 as a colorless oil (3.2 mg, 0.0062 mmol, 49% yield) as product: MS (ESI+) calculated for [C$_{26}$H$_{35}$Cl$_7$+Na]$^+$: 517.20. found: 517.20. $^1$H NMR (500 MHz, CDCl$_3$) δ 7.39-7.29 (m, 5H), 4.93 (d, J=11.6 Hz, 1H), 4.68 (dd, J=8.1, 4.0 Hz, 1H), 4.51 (dd, J=10.3, 4.0 Hz, 1H), 4.48 (d, J=10.3, Hz, 1H), 4.46 (d, J=11.6 Hz, 1H), 3.77 (m, 1H), 3.68 (s, 1H), 3.29 (dd, J=1.7 Hz, 1H), 2.65 (dd, J=13.8, 6.4 Hz, 1H), 2.54 (dd, J=0.8 Hz, 1H), 2.50 (m, 1H), 2.49 (dq, J=10.7, 7.3 Hz 1H), 1.92-1.99 (m, 1H), 1.82 (dd, J=13.8, 7.7 Hz, 1H), 1.68 (s, 3H), 1.52-1.60 (m, 1H), 1.30 (d, J=7.3 Hz, 3H), 1.28 (s, 3H), 0.93 (t, J=7.5 Hz, 3H), 0.89 (d, J=7.1 Hz, 3H); $^{13}$C NMR (125 MHz, CDCl$_3$) δ 206.8, 205.8, 173.7, 130.0, 128.6, 128.3, 127.7, 90.1, 79.5, 79.1, 78.3, 76.3, 70.9, 51.7, 43.9, 38.9, 34.7, 34.6, 24.8, 23.2, 17.0, 16.2, 14.2, 11.0.

Example 36

Preparation of Compound 252

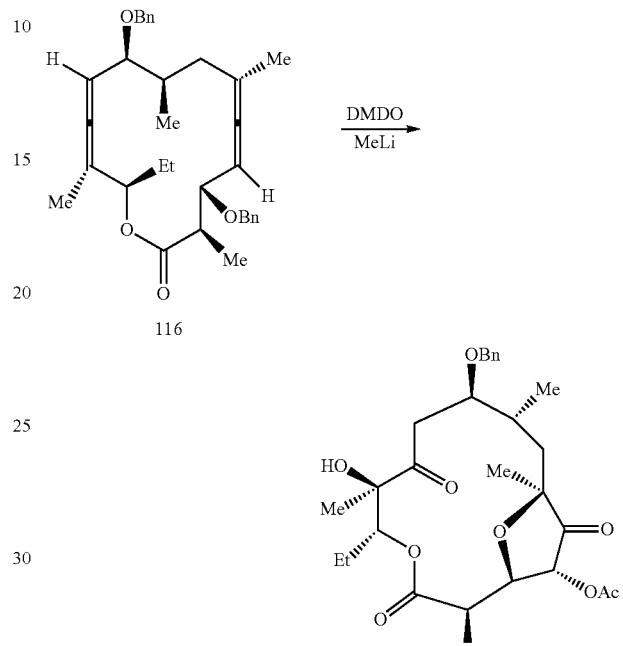

116

252

To the neat bis[allene]macrolactone 116 (19.6 mg, 0.0392 mmol) was added a solution of DMDO (4.60 ml, 0.783 mmol) dropwise at −40° C. The temperature was increased to −24° C. over 36 minutes. Excess DMDO was removed under reduced pressure at −20° C. To the crude product was added a solution of MeLi (146 μl, 0.234 mmol) at −63° C. After the complete consumption of spirodiepoxide, the reaction was then quenched with water and extracted with Et2O. The combined organic phase was dried over anhydrous Na2SO4. Evaporation of solvent and FCC purification using 15% EtOAc in hexanes gave 27 (2.0 mg, 10.7% yield) as colorless oil: $^1$H NMR (500 MHz, CDCl$_3$) δ 7.36-7.28 (m, 5H), 4.58 (d, J=9.1 Hz, 1H), 4.49 (d, J=10.9 Hz, 1H), 4.32 (d, J=10.9 Hz, 1H), 4.14 (m, 1H), 4.04 (dd, J=10.4, 2.1 Hz, 1H), 3.96 (dd, J=9.1, 5.1 Hz, 1H), 3.41 (d, J=9.5 Hz, 1H), 3.29 (m, 1H), 2.51 (d, J=3.8 Hz, 1H), 1.75 (dd, J=15.0, 9.4 Hz, 1H), 1.65 (dd, J=15.0, 2.8 Hz, 1H), 1.64 (m 1H), 1.63 (dd, J=15.0, 2.8 Hz, 1H), 1.47 (s, 3H), 1.30 (d, J=7.3 Hz, 3H), 1.26 (m, 1H), 1.20 (s, 3H), 1.05 (t, J=7.4 Hz, 3H), 0.86 (d, J=6.9 Hz, 1H); $^{13}$C NMR (125 MHz, CDCl$_3$) δ 217.1, 208.1, 174.5, 137.9, 129.0, 128.3, 93.2, 83.9, 79.8, 78.1, 76.2, 73.2, 73.1, 42.6, 42.0, 41.2, 35.9, 24.9, 23.5, 21.0, 17.6, 13.1, 11.3.

Compound 252 can also be prepared as follows.

To a solution of macrolactone 116 (17.7 mg, 0.0340 mmol) in CDCl$_3$ (0.5 mL) was added a solution of DMDO (0.56 mL, 0.21 mmol) dropwise at −40° C., warmed up to −15° C. over 30 minutes, then lower order methyl cyanocuprate (MeCuCNLi, 0.71 mmol) was added, prepared by addition of MeLi (0.44 mL, 0.71 mmol) to a slurry of CuCN (63 mg, 0.71 mmol) in 2-methyl THF (5.99 mL) at −78° C. and then warming to −15° C. The mixture was warmed to −2° C. over 1.5 h, quenched with saturated aqueous solution of NH$_4$OH and NH$_4$Cl (1:4 ratio) and then extracted with diethyl ether. The combined organic layer was dried over anhydrous Na$_2$SO$_4$, filtered and then concentrated under reduced pressure to give the crude product, which was purified by FCC using 15% ethyl acetate in hexane to afford compound 252 (10 mg, 64% yield) as a colorless oil. For detailed NMR analysis, see page S30. IR vmax (neat)/cm$^{-1}$ 3434, 2968, 2925, 1959, 1764, 1725, 1452, 1370, 1155; $^1$H NMR (600 MHz, CDCl$_3$) δ 7.35-7.28 (m, 5H), 5.60 (dd, J=8.1, 6.3 Hz, 1H), 5.07 (m, 2H), 4.62 (d, J=12.1 Hz, 1H), 4.36 (d, J=12.1 Hz, 1H), 3.90 (dd, J=8.7, 4.4 Hz, 1H), 3.83 (dd, J=8.1, 2.6 Hz, 1H), 3.06 (m, 1H), 1.87 (dd, J=15.0, 5.8 Hz, 1H), 1.80 (d, J=2.8 Hz, 3H), 1.70 (m, 2H), 1.65 (m, 2H), 1.35 (d, J=7.4 Hz, 2H), 1.14 (s, 3H), 0.93 (t, J=7.6 Hz, 3H), 0.88 (d, J=7.0 Hz, 3H); $^{13}$C NMR (150 MHz, CDCl$_3$) δ 218.9, 206.6, 171.0, 138.9, 128.2, 127.7, 127.3, 99.0, 90.7, 83.4, 82.3, 79.7, 76.6, 72.5, 70.2, 42.9, 40.2, 34.0, 24.3, 22.8, 14.5, 13.8, 13.6, 10.0; MS (ESI+) calculated for [C$_{26}$H$_{34}$O$_6$+Na]$^+$: 465.2. found: 465.5. [α]$^{25}_D$=5.9° (c=0.005, CHCl$_3$).

Example 37

The following illustrate representative pharmaceutical dosage forms, containing a compound of formula I ('Compound X'), for therapeutic or prophylactic use in humans.

| (i) Tablet 1 | mg/tablet |
|---|---|
| Compound X = | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| Compound X = | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| Compound X = | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/ml) | mg/ml |
|---|---|
| Compound X = (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/ml) | mg/ml |
|---|---|
| Compound X = (free acid form) | 10.0 |
| Monobasic sodium phosphate | 0.3 |
| Dibasic sodium phosphate | 1.1 |

| | |
|---|---|
| Polyethylene glycol 400 | 200.0 |
| 01N Sodium hydroxide solution (pH adjustment to 7.0-7.5) | q.s. |
| Water for injection | q.s. ad 1 mL |

| (vi) Aerosol | mg/can |
|---|---|
| Compound X = | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound of formula 239a:

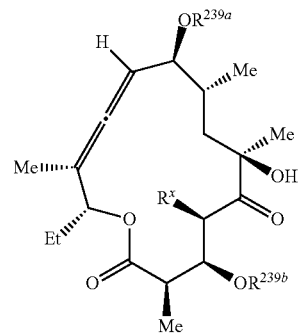

wherein:

R$^{239a}$ is H or a hydroxy protecting group;

R$^{239b}$ is H or a hydroxy protecting group; and

R$^x$ is H, halo, amino, or cyano.

2. A compound of formula 239a:

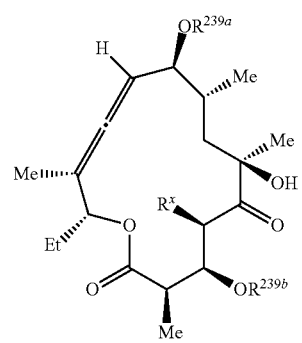

wherein:
R²³⁹ᵇ is H or benzyl;
R²³⁹ᵇ is H or benzyl; and
Rˣ is fluoro, chloro, or bromo.
3. A compound of formula 239:
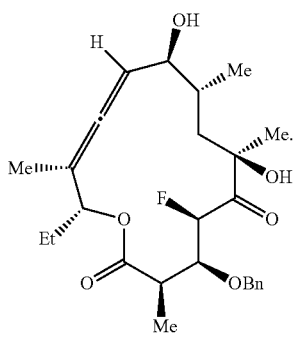
239
4. A compound of formula 239a:
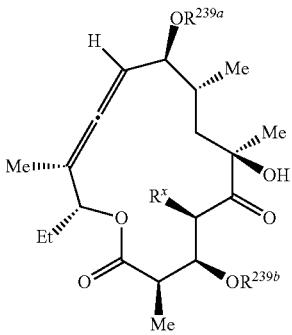
239a
wherein:
R²³⁹ᵃ is H or a hydroxy protecting group;
R²³⁹ᵇ is H or a hydroxy protecting group; and
Rˣ is H.
* * * * *

UNITED STATES PATENT AND TRADEMARK OFFICE
CERTIFICATE OF CORRECTION

PATENT NO. : 8,796,474 B1  
APPLICATION NO. : 13/215986  
DATED : August 5, 2014  
INVENTOR(S) : Williams et al.

Page 1 of 1

It is certified that error appears in the above-identified patent and that said Letters Patent is hereby corrected as shown below:

On the Title Page, Item (73) Assignee:

Replace:

Rutgers, the State University of New Jersey, New Brunswick, NJ (US)

With:

Rutgers, The State University of New Jersey, New Brunswick, NJ (US)

In the Specification

In Column 1, Lines 5-10 Under Statement of Government Support:

Replace:

The invention described herein was made with United States Government support under Grant Number R01GM078145 awarded by The National Institutes of Health. The United States Government has certain rights in the invention.

With the following revised paragraph:

This invention was made with government support under RO1GM078145 awarded by the National Institutes of Health. The government has certain rights in the invention.

Signed and Sealed this  
Twenty-seventh Day of October, 2015

Michelle K. Lee  
*Director of the United States Patent and Trademark Office*